US012773485B2

(12) United States Patent
Hobro et al.

(10) Patent No.: US 12,773,485 B2
(45) Date of Patent: Oct. 27, 2026

(54) DIALYSIS MACHINE AND METHOD

(71) Applicant: GAMBRO LUNDIA AB, Lund (SE)

(72) Inventors: Sture Hobro, Lund (SE); Roger Nilsson, Höör (SE); Olof Jansson, Vellinge (SE); Björn Ericson, Lund (SE)

(73) Assignee: Gambro Lundia AB, Lund (SE)

( * ) Notice: Subject to any disclaimer, the term of this patent is extended or adjusted under 35 U.S.C. 154(b) by 324 days.

(21) Appl. No.: 18/439,187

(22) Filed: Feb. 12, 2024

(65) Prior Publication Data

US 2024/0181147 A1 Jun. 6, 2024

Related U.S. Application Data

(63) Continuation of application No. 16/757,961, filed as application No. PCT/EP2018/079243 on Oct. 25, 2018, now Pat. No. 11,896,752.

(30) Foreign Application Priority Data

Oct. 27, 2017 (EP) .................................... 17198737

(51) Int. Cl.
*A61M 1/36* (2006.01)
*A61M 60/279* (2021.01)

(52) U.S. Cl.
CPC ........ *A61M 1/3646* (2014.02); *A61M 1/3627* (2013.01); *A61M 1/365* (2014.02); *A61M 1/3652* (2014.02); *A61M 60/279* (2021.01); *A61M 1/3649* (2014.02)

(58) Field of Classification Search
CPC .............. A61M 1/3627; A61M 1/3646; A61M 1/3649; A61M 1/365; A61M 1/3652; A61M 60/279
See application file for complete search history.

(56) References Cited

U.S. PATENT DOCUMENTS

| | | | |
|---|---|---|---|
| 5,336,165 | A | 8/1994 | Twardowski |
| 5,409,612 | A | 4/1995 | Maltais et al. |
| 5,529,685 | A | 6/1996 | Irie et al. |
| 5,591,344 | A | 1/1997 | Kenley et al. |
| 5,690,831 | A | 11/1997 | Kenley et al. |
| 6,153,102 | A | 11/2000 | Kenley et al. |

(Continued)

FOREIGN PATENT DOCUMENTS

| | | |
|---|---|---|
| DE | 3442744 | 11/1984 |
| DE | 69321 403 | 3/1999 |

(Continued)

OTHER PUBLICATIONS

Operating Manual DBB-EXA No. 1019de-B4 Nikkiso Co., LTD., 10 pages.

(Continued)

*Primary Examiner* — Dirk R Bass
(74) *Attorney, Agent, or Firm* — K&L Gates LLP

(57) ABSTRACT

A method and a dialysis machine for draining an extracorporeal fluid circuit are disclosed herein. The dialysis machine is connected to a dialyzer and the extracorporeal fluid circuit, which includes an arterial line connectable to a patient for drawing blood from the patient and a venous line connectable to the patient for returning blood to the patient. The method includes, after treatment termination, draining remaining fluid from the extracorporeal fluid circuit through the dialyzer.

19 Claims, 18 Drawing Sheets

(56) References Cited

U.S. PATENT DOCUMENTS

| | | | |
|---|---|---|---|
| 7,488,301 | B2 | 2/2009 | Beden et al. |
| 8,409,127 | B2 | 4/2013 | Gronau et al. |
| 2010/0168640 | A1 | 7/2010 | Kopperschmidt et al. |
| 2010/0329910 | A1 | 12/2010 | Baumann et al. |
| 2014/0158589 | A1 | 6/2014 | Furuhashi et al. |
| 2017/0296733 | A1 | 10/2017 | Riemenschneider |

FOREIGN PATENT DOCUMENTS

| | | |
|---|---|---|
| DE | 102016107026 | 10/2017 |
| EP | 0 458 041 | 11/1991 |
| EP | 0 578 175 | 1/1994 |
| EP | 0 846 470 | 10/1998 |
| EP | 1 025 427 | 8/2000 |
| EP | 1 295 617 | 3/2003 |
| EP | 1 457 218 | 9/2004 |
| EP | 2 059 279 | 5/2009 |
| EP | 2 535 065 | 12/2012 |
| EP | 2 583 701 | 4/2013 |
| EP | 2 583702 | 4/2013 |
| EP | 2 708 249 | 3/2014 |
| EP | 2 745860 | 6/2014 |
| ES | 2 554 639 | 12/2015 |
| JP | 2001259024 | 9/2001 |
| WO | 96 040313 | 12/1996 |
| WO | 01 021233 | 3/2001 |
| WO | 01/051106 | 7/2001 |
| WO | 2004033001 | 4/2004 |
| WO | 2005061026 | 7/2005 |
| WO | 2007104447 | 9/2007 |
| WO | 2008 028579 | 3/2008 |
| WO | 2009 006261 | 1/2009 |
| WO | 2009 061608 | 5/2009 |
| WO | 2010091841 | 8/2010 |
| WO | 2013017240 | 2/2013 |
| WO | 20140110004 | 7/2014 |
| WO | 2014121157 | 8/2014 |
| WO | 2016/001217 | 1/2016 |
| WO | 2024039713 | 2/2024 |

OTHER PUBLICATIONS

Hans-Dietrich olaschegg and Nathan W. Levin, Drukker, Parsons and Maher, “Replacement of Renal Function by Dialysis”, 5th Edition. 4 pages. pp 354-356.

Gunther Meyer, Hemodialysis: Technology and Application; a compendium for physicians, nursing staff, and technicians, Fresenius Medical Care Reference Library—8 pages.

Gunther SchonweiB, “Dialysis Primer 3: Individuality, Flexibility, and Quality in Dialysis,” vol. 2, pp. 630-658 with translation 28 pages.

International Search Report; International Application No. PCT/EP2018/079243; mailed Apr. 3, 2019; 7 Pages.

Written Opinion of the International Searching Authority; International Application No. PCT/EP2018/079243; mailed Apr. 3, 2019; 13 Pages.

Extended European Search Report issued in related EP Application No. 17198737.3 mailed May 2, 2018—13 Pages.

DIALYSIS MACHINE AND METHOD

PRIORITY CLAIM

The present application is a continuation application of U.S. application Ser. No. 16/757,961, filed Apr. 21, 2020, now U.S. Pat. No. 11,896,752, which is a National Phase of International Application No. PCT/EP2018/079243, filed Oct. 25, 2018, which claims priority to EP Application No. 17198737.3, filed Oct. 27, 2017, the entire contents of each of which are incorporated herein by reference and relied upon.

TECHNICAL FIELD

The present technology relates to a method for draining an extracorporeal fluid circuit utilizing a dialysis machine and a dialysis machine configured to perform said method. The present technology further relates to a method for filling an extracorporeal fluid circuit with rinse-back fluid and a dialysis machine configured to perform said method.

BACKGROUND

Returning of blood to the patient in the end of a dialysis treatment usually requires rinse-back fluid for pushing the blood into the patient through the extracorporeal fluid circuit i.e. the blood line. This is due to it not being a good manner even with air and blood sensors as security measures, to introduce air in the extracorporeal fluid circuit when a patient is connected, since air infused to the patient could lead to air embolism. Accordingly, rinse-back fluid which can be injected into the patient without potential negative health effects is preferable for pushing back the blood.

When the rinse-back fluid is introduced it may potentially become contaminated with bacteria or virus in the blood of the patient which is present in the line set. Accordingly, the line is filled with a mixture of rinse-back fluid and blood at the end of the treatment and needs to be handled in a safe manner.

Handling of a contaminated and filled line set is performed after a treatment is conducted. The line set and dialyzer is at that point filled with a mixture of blood which has to be disposed. Today, this may be manually performed by the nurse by either emptying the line set in a sink or by disposal of the entire line set without emptying it first.

Emptying of the line set requires pouring of the contained liquid through a manual process which is time consuming, dangerous and somewhat dirty due to the handling of the potentially contaminated liquid. After the content has been discharged, the line set can be disposed.

To avoid spillage and achieve a cleaner handling method, the line set is often disposed without emptying of the line set first. Instead, the nurse clamp the ends of the line set with a set of clamps constituting a part of said line set. After the ends have been sealed off with said clamps the entire line set is removed from the dialysis machine and is disposed. However, this of course increases the weight of the waste to be treated, which leads to an increased cost for the clinic due to the waste handling fees for contaminated material which can be quite considerable since a clinic often performs numerous of dialysis treatments each day.

During priming, i.e. preparation of the line set before the treatment is conducted, a similar handling is often used which implements pumping a priming fluid into the line set to fill and flush the blood line and the dialyzer. Traditionally this has been performed by pumping of saline from a saline bag connected to the line set, but more and more systems begin to provide priming fluid directly from the machine, so called "on-line priming".

Several newer dialysis machines utilizes on-line priming and include a Waste Handling Option (WHO) for handling the priming fluid. In such a dialysis machine the used priming fluid is sucked into the drain side of the machine. So far, the WHO port has only been used to the removal of priming fluid due to a possible increase in the risk of cross-contamination between patients.

For example, there is a risk for blood to be sucked into the machine during treatment through the WHO port. Therefore possible contamination of the WHO would create a risk of the contamination being pushed back into the line set.

Hence, there is a need for a method for draining a line set in a safe, cost-efficient and simple manner. There is also a need for a method for draining a line set which reduces the risk for cross-contamination between patients.

SUMMARY

Accordingly, the present technology preferably seeks to mitigate, alleviate or eliminate one or more of the above-identified deficiencies in the art and disadvantages singly or in an any combination and solves at least the above mentioned problems by providing a method for draining an extracorporeal fluid circuit utilizing a dialysis machine, wherein the dialysis machine is connected to a dialyzer and said extracorporeal fluid circuit; said extracorporeal fluid circuit comprising an arterial line connectable to a patient, for drawing blood from the patient and a venous line connectable to the patient for returning blood to the patient, the method comprising after treatment termination from said extracorporeal fluid circuit draining remaining fluid from said extracorporeal fluid circuit through the dialyzer.

Treatment termination refers to a state where the dialysis treatment has been interrupted or completed.

Present technology may further relate to a dialysis machine connected to an extracorporeal fluid circuit and a dialyzer, wherein said extracorporeal fluid circuit comprises an arterial line connectable to a patient for drawing blood form the patient and a venous line connectable to the patient for returning blood to the patient, said dialysis system being configured to perform the method for draining.

According to one aspect of the invention a method for filling an extracorporeal fluid circuit is provided. Said method may be included in said method for draining. Thus, present technology further relates to a method for filling an extracorporeal fluid circuit with rinse-back fluid after treatment termination, using a dialysis machine, wherein the dialysis machine is connected to a dialyzer, said extracorporeal fluid circuit and a pumping device connected to the extracorporeal fluid circuit; said extracorporeal fluid circuit comprising an arterial line having a first port connectable to a patient, for drawing blood form the patient and a venous line having a second port, connectable to the patient, for returning blood to the patient; the method comprising pumping rinse-back fluid into the extracorporeal fluid circuit, thereby filling the extracorporeal fluid circuit by activating the pumping device to generate a flow of rinse-back fluid in the direction of the second port through the dialyzer.

Treatment termination refers to a state where the dialysis treatment has been interrupted or completed.

Present technology may further relate to a dialysis machine connected to a dialyzer and a pumping device connected to the extracorporeal fluid circuit; said extracorporeal fluid circuit comprising an arterial line having a first port connectable to a patient, for drawing blood from the patient, a venous line having a second port, connectable to the patient, for returning blood to the patient, the dialysis machine being configured to perform the method of filling.

Further advantageous embodiments are disclosed in the appended and dependent patent claims.

BRIEF DESCRIPTION OF DRAWINGS

The above, as well as additional objects, features and advantages of the present technology, will be better understood through the following illustrative and non-limiting detailed description of preferred embodiments of the present technology, with reference to the appended drawings.

DETAILED DESCRIPTION

Figure 1:
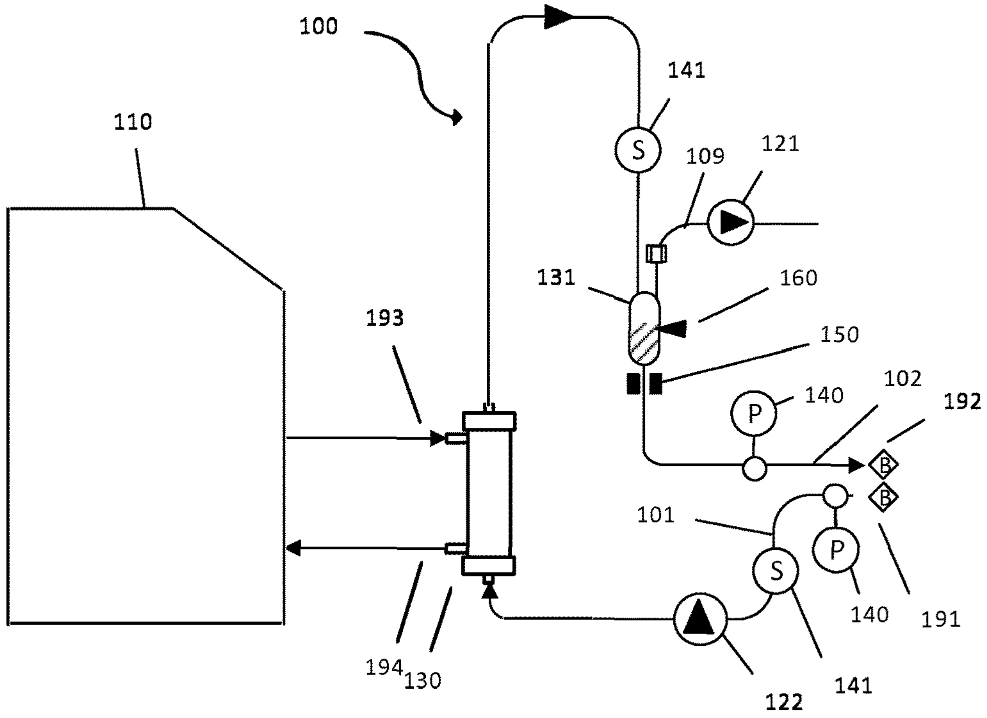
FIG. 1 schematically illustrates a dialysis system of one embodiment in a first state.

The present technology relates to a method for draining an extracorporeal fluid circuit utilizing a dialysis machine of a dialysis system. With the present invention the remaining fluid of the extracorporeal fluid circuit may be drained through the dialyzer.

Accordingly, present technology relates to a method for draining an extracorporeal fluid circuit utilizing a dialysis machine, wherein the dialysis machine is connected to a dialyzer and said extracorporeal fluid circuit. Said extracorporeal fluid circuit comprises an arterial line connectable to a patient, for drawing blood from the patient and a venous line connectable to the patient for returning blood to the patient. The method comprises to after treatment termination from said extracorporeal fluid circuit draining remaining fluid from said extracorporeal fluid circuit through the dialyzer.

The present technology also relates to a method for filling an extracorporeal fluid circuit with rinse-back fluid.

Accordingly, present technology relates to a method for filling an extracorporeal fluid circuit with rinse-back fluid after treatment termination, using a dialysis machine. The dialysis machine is connected to a dialyzer and said extracorporeal fluid circuit, whereby a pumping device is connected to the extracorporeal fluid circuit, said extracorporeal fluid circuit comprising an arterial line having a first port connectable to a patient, for drawing blood form the patient and a venous line having a second port, connectable to the patient, for returning blood to the patient. The method comprises to pump rinse-back fluid into the extracorporeal fluid circuit, thereby filling the extracorporeal fluid circuit by activating the pumping device to generate a flow of rinse-back fluid in the direction of the second port through the dialyzer.

After treatment termination may refer to the state where no blood is drawn from the patient.

Referring to FIG. 1-4, an embodiment of a dialysis system in different states during the method of draining is shown. The dialysis system comprises a dialysis machine 110 connected to an extracorporeal fluid circuit 100 and a dialyzer 130, wherein said extracorporeal fluid circuit 100 comprises an arterial line 101 connectable to a patient for drawing blood form the patient and a venous line 102 connectable to the patient for returning blood to the patient, said dialysis machine of the dialysis system being configured to perform the method for draining.

Connected to the extracorporeal fluid circuit is a peristaltic blood pump 122. The blood pump may be arranged to generate a flow both in the direction of the first port 191 i.e. the arterial line 101 as well as the second port 192 i.e. the venous line 102. Further, the peristaltic pump disallows, i.e.

substantially prevents, flow through the pump when the pump is not activated as is conventional within the field of peristaltic pumps.

With reference to FIG. 1, a dialysis system immediately after treatment termination, i.e. after efforts to return patient's blood has been terminated, i.e. when dialysis treatment has been interrupted or completed, is shown. The extracorporeal fluid circuit may thus be filled with blood which may be drained in order to reduce the weight of the disposed material of the clinic. Thereby, the cost for handling the disposed material is severely reduced. The rinse-back fluid may for example be saline, gas or dialysis fluid.

The patient is connected with the arterial line 101 and venous line 102 via the ports 191 and 192, i.e. the ports 191 and 192 are connected to the bloodstream of the patient. The dialysis machine 110 is connected to the dialyzer 130 via a first dialyzer line 193 and a second dialyzer line 194 forming a dialyzer fluid circuit. The dialyzer 130 in turn is connected to the extracorporeal fluid circuit 100.

In order to provide the distribution of substitution fluid to and from the dialyzer required for HD-dialysis the dialyzer is connected to a pump arrangement via the dialyzer fluid circuit 193, 194. Said pump arrangement is arranged to control the distribution of dialysis fluid into and from the extracorporeal fluid circuit via the dialyzer 130 and will be more closely described with reference to FIG. 20.

The fluid circuit 100 is connected to an air pump 121 via an inlet 109 connected to the fluid circuit 100, for example via a venous drip chamber 131 situated between the dialyzer 130 and the second port 192. Hence, the air pump 121 may be connected to the venous line 102.

Due to the risk for air embolism the extracorporeal fluid circuit 100 may be provided with an air sensor 150 configured to detect air in the fluid passing through the section of the fluid circuit provided with the air sensor 150. The air sensor 150 may for example be configured to generate a signal when air is detected which prompts an alarm to the operator or be received by a controller directly stopping the dialysis treatment.

Further, the venous drip chamber 131 may be provided with a level sensor 160 configured to monitor the level of fluid inside the chamber of said drip chamber 131.

As is well-known for the skilled person, the extracorporeal fluid circuit 100 may comprise a pressure sensor 140 for monitoring the pressure in the extracorporeal fluid circuit.

Further, the extracorporeal fluid circuit may comprise a sample port 141 for extracting blood samples or dialysis fluid samples.

Figure 2:
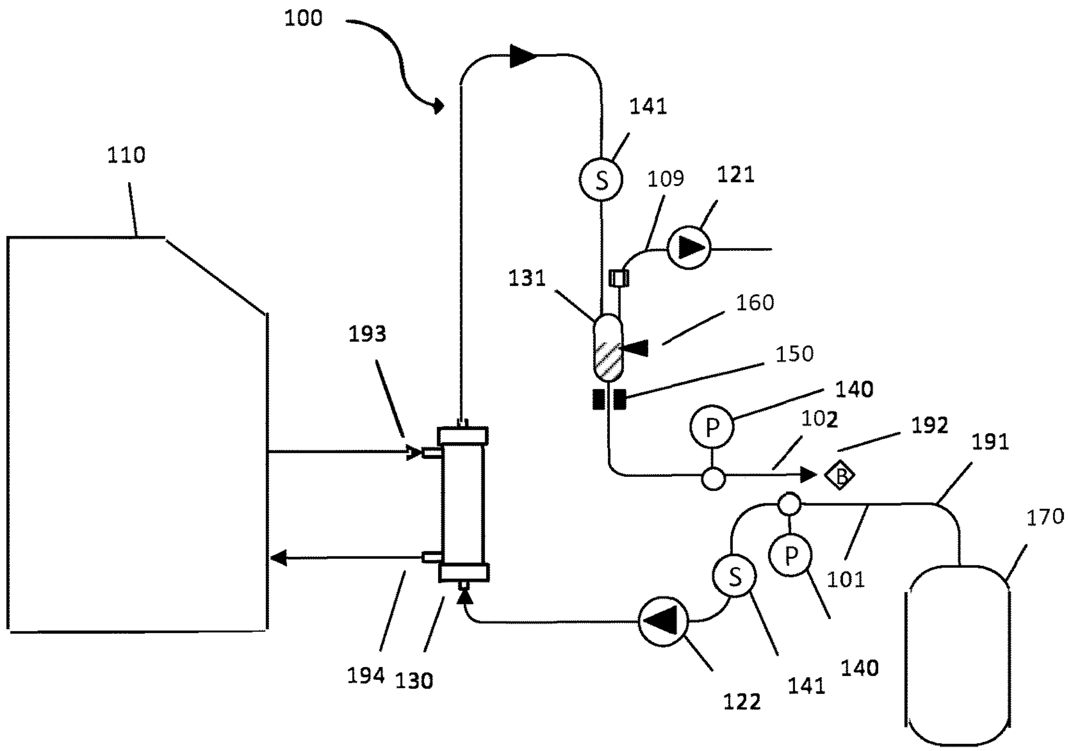
FIG. 2 schematically illustrates a dialysis system of one embodiment in a second state.

Referring to FIG. 2, a rinse-back fluid is introduced into the extracorporeal fluid circuit 100 for rinse-back of blood to the patient prior to the draining of remaining fluid. The arterial line 101 has been disconnected from the blood stream of the patient through disconnection of the first port 101. Instead, the arterial line 101 is connected to a rinse-back fluid container 170 prior to rinse-back being introduced into the fluid circuit 100. The rinse-back fluid may be Saline or dialysis fluid, whereby the rinse-back container 170 may for example be a Saline bag or a substitution fluid bag i.e. dialysis fluid bag. Alternatively, the rinse-back container 170 may be a supply of gas, saline or substitution fluid i.e. dialysis fluid.

In order to reduce potential waste of blood by draining fluid with a relatively high concentration of blood, the second port 192 may remain in connection with the blood stream of the patient thus allowing for continuous filling of the extracorporeal fluid circuit 100 until the blood concentration is sufficiently low, i.e. when only small residuals of blood are left in the extracorporeal fluid circuit 100.

The dialysis machine 110 is connected to the peristaltic blood pump 122, said blood pump being connected to the arterial line 101. The introduction of rinse-back fluid is thus achieved by activation of the peristaltic blood pump 122. Thereafter, the rinse-back fluid flows from the container 170 through the dialyzer 130 towards the venous line 102. Thereby, remaining fluid from the treatment in the extracorporeal fluid circuit 100 is pushed by the rinse-back fluid towards the venous line 192 through the dialyzer 130. Hence, the remaining fluid from the treatment is pushed through the dialyzer blood line (not shown) of the dialyzer 130 towards the venous line, the dialyzer blood line will be described in further detail with reference to FIG. 20.

Figure 3:
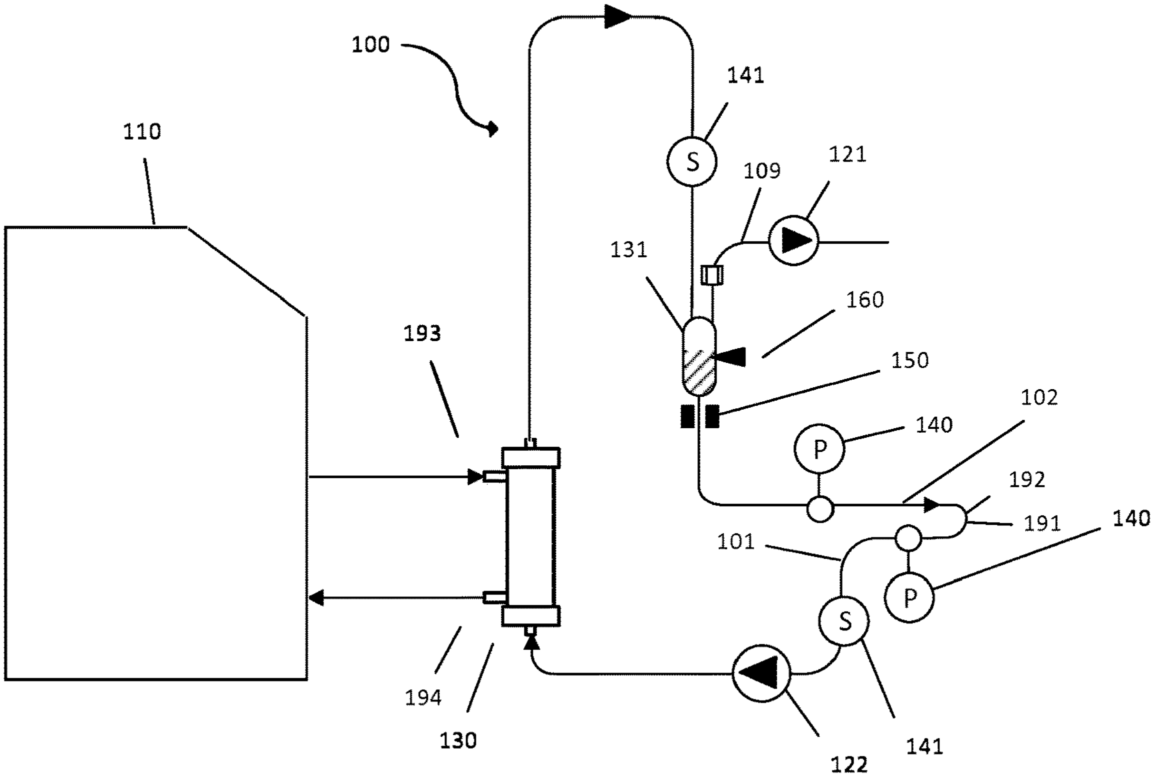
FIG. 3 schematically illustrates a dialysis system of one embodiment in a third state.

Referring to FIG. 3, the first port 191 and the second port 192 may be connected, e.g. the arterial line 101 and the venous line 102 may be connected, when the extracorporeal fluid circuit 100 is substantially filled with rinse-back fluid. Notably, at this point there may still be a certain concentration of blood inside the fluid of the extracorporeal fluid circuit 100. At this point neither of said first port 191 and second port 192 is connected to the bloodstream of the patient.

The extracorporeal fluid circuit thus becomes a closed-off circuit, allowing for initiation of the removal of the remaining fluid, which at this point may be a mixture of blood residuals from the patient and rinse-back fluid.

Figure 4:
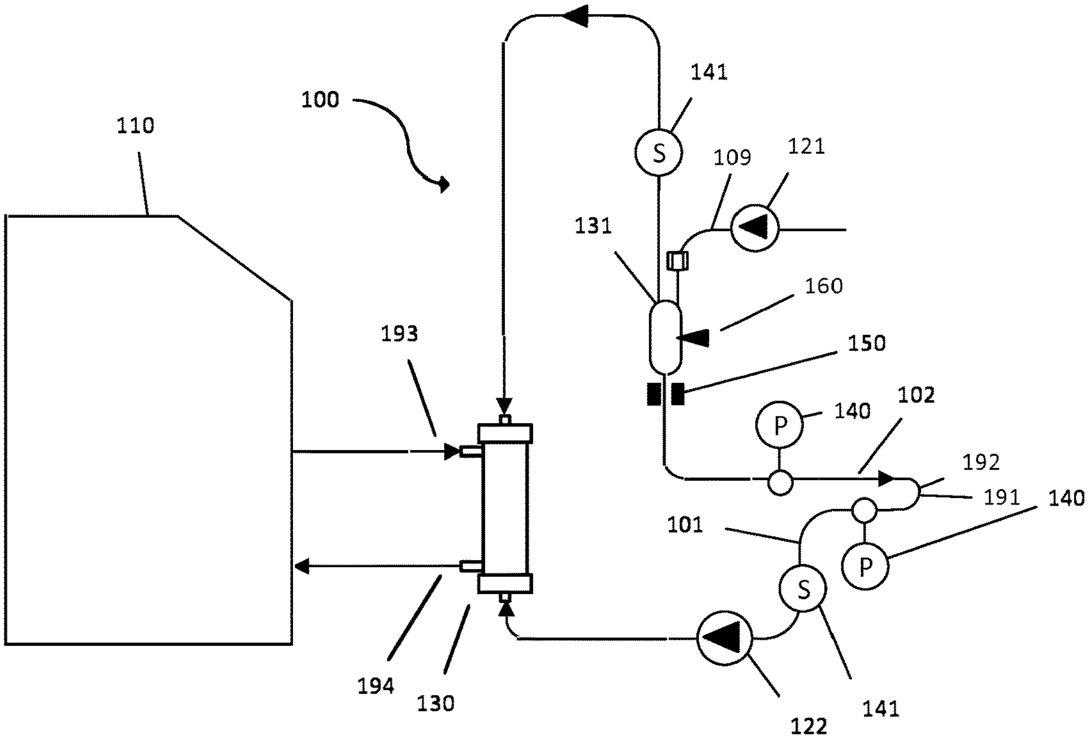
FIG. 4 schematically illustrates a dialysis system of one embodiment in a fourth state.

The extracorporeal fluid circuit is thereafter emptied of remaining fluid, which is schematically depicted in FIG. 4. The emptying is initiated by applying a negative pressure on the dialyzer fluid circuit 193, 194 for distribution to and from the dialyzer 130 relative the extracorporeal fluid circuit 100, the dialysis machine 110 being connected to the dialyzer 130 via said dialyzer fluid circuit 193, 194. Said negative pressure forces the rinse-back fluid towards the dialyzer 130 from the venous line 102 and allows for a net removal of fluid from the dialyzer 130 to the dialysis machine 130 where it may be led to a drain (not shown).

The negative pressure applied on the dialyzer fluid circuit relative the extracorporeal fluid circuit may in other words be considered as inducing a pressure difference between the extracorporeal fluid circuit 100 and the dialyzer fluid circuit 193, 194 to create suction, e.g. flow, of fluid into the dialyzer fluid circuit 193, 194 from the extracorporeal fluid circuit.

The suction and consequential flow of rinse-back flow may be achieved in a number of ways. For example, by selective clamping of the fluid circuit 100 through clamps and suction and flow control or control of the pressure through valve arrangements. Alternatively, the negative pressure may be applied through introducing of a gas into the extracorporeal fluid circuit 100 via the inlet 109, whereby the remaining fluid is pushed towards the dialyzer 130 for draining through the dialysis machine. As further shown in FIG. 5-18, the negative pressure may be applied in several ways.

According to present embodiment, this may be performed with a pumping device 121, such as the air pump 121, connected to the extracorporeal fluid circuit 100 via the inlet 109, as depicted by air pump being activated so as to pump in a direction into the extracorporeal fluid circuit 100 in FIG. 4. Thus, the air pump 121 introduces gas into the extracorporeal fluid 100 so as to ensure the pressure difference between the dialyzer fluid circuit and the extracorporeal fluid circuit 100, thereby forcing the fluid towards the dialyzer.

To remove the remaining fluid, i.e. the rinse-back fluid filling the extracorporeal fluid circuit 100 together with potential residues from the treatment, a net removal of the remaining fluid has to be achieved. Accordingly, the remaining fluid This may for example be achieved by the pump arrangement, whereby the pump arrangement is controlled so as to achieve said net removal of remaining fluid from the dialyzer 130 and the extracorporeal fluid circuit 100 during the applying of negative pressure. In other words, the negative pressure is a negative driving pressure over the dialyzer membrane from the extracorporeal fluid circuit 100 to dialyzer fluid circuit which may situated inside the dialysis machine. Said pump arrangement will be further described with reference to FIG. 20.

Furthermore, there is no possibility for the gas flowing through the extracorporeal fluid circuit 100 on each side of the dialyzer 130 to pass through the dialyzer 130 and thereby hinder the pushing of the remaining fluid towards the dialyzer 130 on the opposite side of said dialyzer 130.

If air is present in the dialyzer and there is no fluid (only a wet membrane), the passage through the dialyzer is closed. That means that if there is any fluid elsewhere in the extracorporeal circuit that fluid cannot be removed. However, as long as there is fluid in the dialyzer that fluid can be removed. Detection of when the dialyzer is "closed" can be done by means of pressure sensors on either side of the dialyzer depending on which side the pressure gradient is created. For example, if the suction is achieved by means of the air pump 121 the pressure may be measured on the extracorporeal side.

Due to the peristaltic blood pump preferably not allowing for flow through it when not activated, said pump 122 may be activated so as to generate a flow of gas i.e. air in the direction of the dialyzer 130. If the blood pump is positioned between the dialyzer 130 and the arterial line 101, said peristaltic blood pump may accordingly generate a flow from the arterial line 101 of the now closed extracorporeal fluid circuit 100 into the dialyzer 130. Thus, the air pump 121 introduces the gas into the closed extracorporeal fluid circuit 100 towards the dialyzer 130 both via the venous line 102 and the arterial line 101, whereby the pumping peristaltic blood pump 122 enables the gas i.e. air passing through the arterial line towards the dialyzer 130. The flow of air thus pushes the fluid inside the circuit into the dialyzer 130 according to a similar flow pattern.

The speed of the filling of gas i.e. the speed of the emptying of the extracorporeal fluid circuit 100 may thus be controlled through controlling of the pump arrangement connected to the dialyzer fluid circuit 193, 194, the peristaltic blood pump 122 and the air pump 121.

Accordingly, the entire fluid circuit 100 becomes filled with gas thus being empty of fluid due to the net removal of fluid taking place in the dialyzer 130, whereby the extracorporeal fluid circuit 100 may be disposed of without significant spillage or the circuit containing remaining fluid causing an increased waste disposal cost for the clinic.

In order to decrease spillage of further fluid due to disposing of a rinse-back container still containing rinse-back fluid, potentially remaining rinse-back fluid may be drained through the dialyzer 130 after treatment termination as well. This may be performed while controlling the pump arrangement so as to achieve a net removal of fluid from the extracorporeal fluid circuit, whereby the container 170 may become substantially emptied of fluid due to the net removal of fluid from the extracorporeal fluid circuit 100. The remaining fluid may be drained via the dialyzer fluid circuit 193, 194. Said dialyzer fluid circuit may be connected to a drain, whereby the remaining fluid may be drained through the dialyzer 130 by draining through the dialyzer fluid circuit 193, 194 to the drain.

Figure 23:
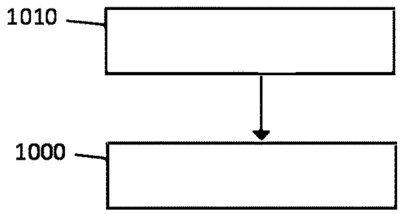
FIG. 23 shows a method for draining an extracorporeal fluid circuit of one embodiment.

Referring to FIG. 23, a method for draining the extracorporeal fluid circuit 100 after treatment termination utilizing a dialysis machine 110 described above is disclosed. The dialysis machine 110 is connected to a dialyzer 130 and said extracorporeal fluid circuit 100, said extracorporeal fluid circuit 100 comprising an arterial line 101 connectable to a patient, for drawing blood from the patient and a venous line 102 connectable to the patient for returning blood to the patient. The method comprising the step of:

after treatment termination from said extracorporeal fluid circuit 110 draining 1000 remaining fluid from said extracorporeal fluid circuit through the dialyzer 130.

Without the risk for cross-contamination the remaining fluid may be handled by the waste handling system of the dialysis machine, i.e. be disposed via the drain of said dialysis machine.

Thereby the operator is not subjected to contaminated fluid in the process of emptying the extracorporeal fluid circuit, since said fluid circuit does not have to be emptied by hand into a sink or a bucket. Thus, a safer and more user-friendly draining process is achieved.

To avoid subjection to contaminated fluid for the operator in a traditional draining method, the entire fluid circuit is typically sealed by clamps and disposed of. However this increases the weight of the disposed material considerably, leading to higher costs for the clinic. Accordingly, the draining through the dialyzer thus enables draining without subjecting the operator to contaminated fluid in a cost-efficient manner since the fluid circuit can be drained of fluid before disposal. The fluid circuit may be emptied completely or only to a level which has been deemed sufficient by the operator.

Treatment termination refers to a state where the dialysis treatment has been interrupted or completed. In other words, the method of draining is performed after said dialysis treatment has been interrupted or completed.

The method may comprise to after treatment termination from said extracorporeal fluid circuit 110 draining 1000 remaining fluid from said extracorporeal fluid circuit through the dialyzer fluid circuit 193, 194 of dialyzer 130.

The extracorporeal fluid circuit 110 may be drained through the dialyzer 130 by applying a negative pressure on the dialyzer fluid circuit 193, 194 relative the extracorporeal fluid circuit 100. Thereby, the remaining fluid is forced towards and through the dialyzer in a stable and robust manner.

The negative pressure may be applied when the patient is disconnected. Accordingly, substantially no blood is drawn from the patient when the remaining fluid is drained through the dialyzer.

Said negative pressure applied on the dialyzer fluid circuit relative the extracorporeal fluid circuit may be applied by introducing of gas into the extracorporeal fluid circuit 100, for example via the inlet 109 whereby the remaining fluid is pushed towards the dialyzer 130 for draining through the dialysis machine 110.

The gas may be pumped into the extracorporeal fluid circuit 100 by the pumping device 121 connected to the extracorporeal fluid circuit 100 via the inlet 109. Hence, the method can be performed by an existing conventional dialysis system with an air pump without requiring additional components increasing the complexity of the dialysis system.

The method may further comprise introducing a rinse-back fluid 1010 into the extracorporeal fluid circuit 100 prior to the draining 1000 for filling the extracorporeal fluid circuit 100.

The introduction of the rinse-back fluid enables blood still in the extracorporeal fluid circuit to be returned. Thereby, the draining method may be performed without blood still in the circuit going to waste.

Figure 24:
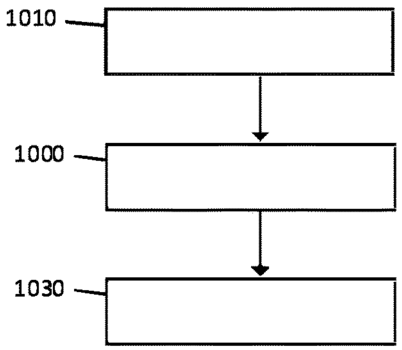
FIG. 24 shows a method for draining an extracorporeal fluid circuit of one embodiment.

Turning to FIG. 24, the method may further comprise controlling 1030 the pump arrangement 63, 64 to achieve a net removal of remaining fluid from the dialyzer 130 and the extracorporeal fluid circuit 100 during the applying of negative pressure. Said net removal consequently causes the extracorporeal fluid circuit to gradually empty so as to enable the disposal of said extracorporeal fluid circuit 100 at a later stage.

The method may accordingly further comprise connecting 1004 the arterial line 101 to the rinse-back fluid container 170 prior to introducing the rinse-back fluid into the fluid circuit 100.

Hence, the method for draining does not require a separate dialysis fluid pump, whereby a draining method with the aforementioned advantages is enabled also for less complex dialysis machine and system without a separate dialysis fluid pump.

In order not to produce additional waste said rinse-back fluid container 170 may be drained until it has been substantially emptied, whereby remaining rinse-back fluid in the rinse-back fluid container 170 may be drained through the dialyzer 130 after treatment termination. However, it should be noted that the rinse-back fluid container may also be only partially emptied, i.e. emptied to a desirable level.

To generate a flow of the rinse-back fluid in the direction of the dialyzer 130, the method may further comprise activating 1005 the peristaltic blood pump 122 to generate a flow of the rinse-back fluid in the direction of the dialyzer 130 after the rinse-back fluid has been introduced 1010.

Before removal of the remaining fluid through the dialyzer 130, the extracorporeal fluid circuit 100 is closed. Accordingly, the method may further comprise connecting 1015 the first port 191 to the second port 192 prior to introducing the gas into the extracorporeal fluid circuit 100.

Consequently, the rinse-back fluid container 170 may be disconnected prior to the connecting of the first port 191 and the second port 192. As an alternative the rinse-back container may be connected to the extracorporeal fluid circuit by means of a separate inlet, whereby the rinse-back container does not have to be disconnected prior to the connecting of the first and second port.

The closing of the fluid circuit effectively reduces the risk for significant spillage of fluid from the fluid circuit during draining, whereby the risk for cross-contamination is reduced greatly.

After draining 1000 the remaining fluid through the dialyzer 130, the remaining fluid may be led out through a drain 68 (which will be further described with reference to FIG. 20). Accordingly, the method may further comprise conveying 1060 the remaining fluid removed from the extracorporeal fluid circuit 100 to a drain 68 of the dialysis machine 110. The drain 68 may be connected to the dialyzer fluid circuit 193, 194

The method may further comprise conveying 1060 the remaining fluid removed from the extracorporeal fluid circuit to the drain 68 of the dialysis machine 110 via the dialyzer fluid circuit 193, 194.

This may be performed immediately after the controlling 1030 of the pump arrangement 63, 64 to achieve the net removal of remaining fluid from the dialyzer 130.

FIG. 5-10 shows a dialysis system according to another embodiment. The dialysis system comprises a dialysis machine 210 connected to an extracorporeal fluid circuit 200 and a dialyzer 230, wherein said extracorporeal fluid circuit 200 comprises an arterial line 201 connectable to a patient for drawing blood form the patient and a venous line 202 connectable to the patient for returning blood to the patient, said dialysis machine of the dialysis system being configured to perform the method for draining.

Connected to the extracorporeal fluid circuit is a peristaltic blood pump 222. The blood pump may be arranged to generate a flow both in the direction of the first port 291 i.e. the arterial line 201 as well as the second port 292 i.e. the venous line 202. Further, the peristaltic pump disallows flow or at least substantially prevent flow when the pump is not activated as is conventional within the field of peristaltic pumps.

Figure 5:
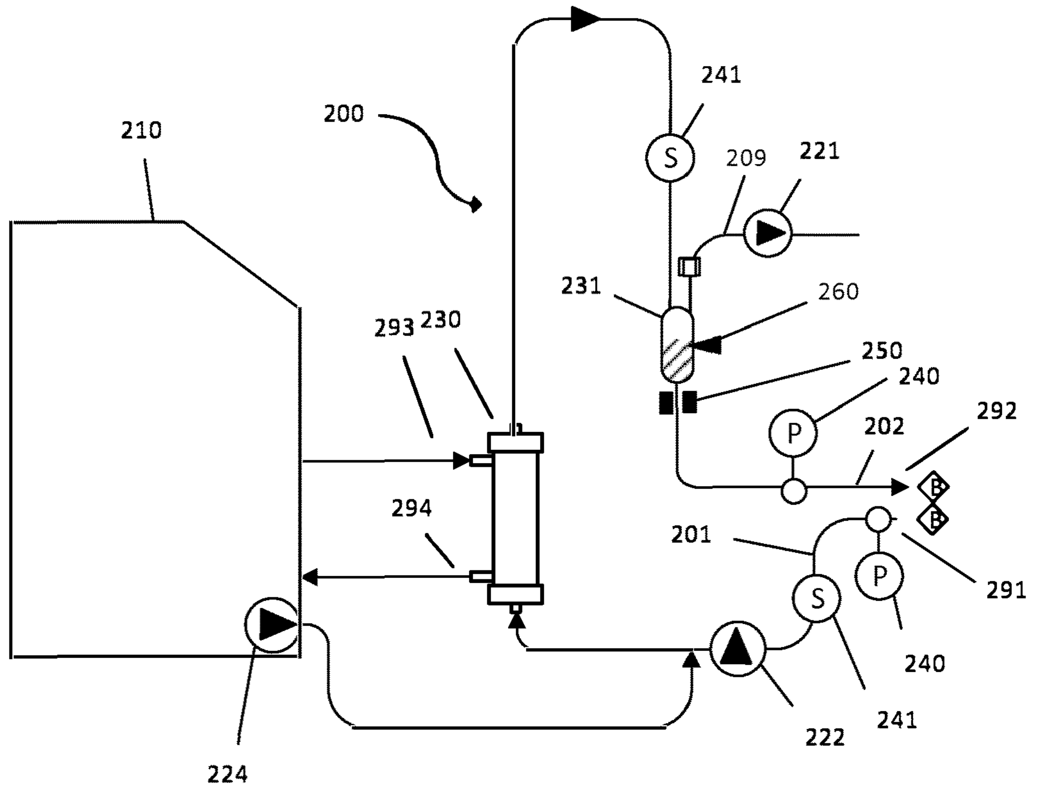
FIG. 5 schematically illustrates a dialysis system of one embodiment in a first state.

With reference to FIG. 5, a dialysis system immediately after treatment termination, i.e. after pumping of a patient's blood into the extracorporeal fluid circuit connected to the dialysis machine has been terminated, is shown. The extracorporeal fluid circuit is thus filled with blood which may be drained in order to reduce the weight of the disposed material of the clinic. Thereby, the cost for handling the disposed material is severely reduced. The rinse-back fluid may for example be saline, gas or dialysis fluid.

The patient is hence connected with the arterial line 101 and venous line 102 via the ports 291 and 292, i.e. the ports 291 and 292 are connected to the bloodstream of the patient. The dialysis machine 210 is connected to the dialyzer 230 via a first dialyzer line 293 and a second dialyzer line 294 forming a dialyzer fluid circuit. The dialyzer 230 in turn is connected to the extracorporeal fluid circuit 200.

In order to provide the distribution of dialysis fluid to and from the dialyzer required for HD-dialysis the dialyzer may be connected to a pump arrangement via the dialyzer fluid circuit 293, 294. Said pump arrangement is arranged to control the distribution of dialysis fluid into and from the extracorporeal fluid circuit via the dialyzer 230 and will be more closely described with reference to FIG. 20.

Further, the pump arrangement may be accompanied by a dialysis fluid pump 224. Hence, the dialysis machine 210 is connected to the dialysis fluid pump 224, which in turn is connected to the extracorporeal fluid circuit 200. The dialysis fluid pump 224 may be connected to the extracorporeal circuit 200 at a position between the peristaltic blood pump 222 and the dialyzer 230. However as the skilled person realizes, the dialysis fluid pump 224 may be connected at several positions in the extracorporeal fluid circuit 200.

The fluid circuit 200 is connected to an air pump 221 via an inlet 209 connected to the fluid circuit 200, for example via a venous drip chamber 231 situated between the dialyzer 230 and the second port 292. Hence, the air pump 221 may be connected to the venous line 202.

Due to the risk for air embolism the extracorporeal fluid circuit 200 may be provided with an air sensor 250 configured to measure the air content in the fluid passing through the section of the fluid circuit provided with the air sensor 250. The air sensor 250 may for example be configured to generate a signal when air is detected which prompts an alarm to the operator or be received by a controller directly stopping the dialysis treatment.

Further, the venous drip chamber 231 may be provided with a level sensor 260 configured to monitor the level of fluid inside the chamber of said drip chamber 231.

As is well-known for the skilled person, the extracorporeal fluid circuit 200 may comprise a pressure sensor 240 for monitoring the pressure inside the extracorporeal fluid circuit.

Further, the extracorporeal fluid circuit may comprise a sample port 241 for extracting blood samples or dialysis fluid samples.

Figure 6:
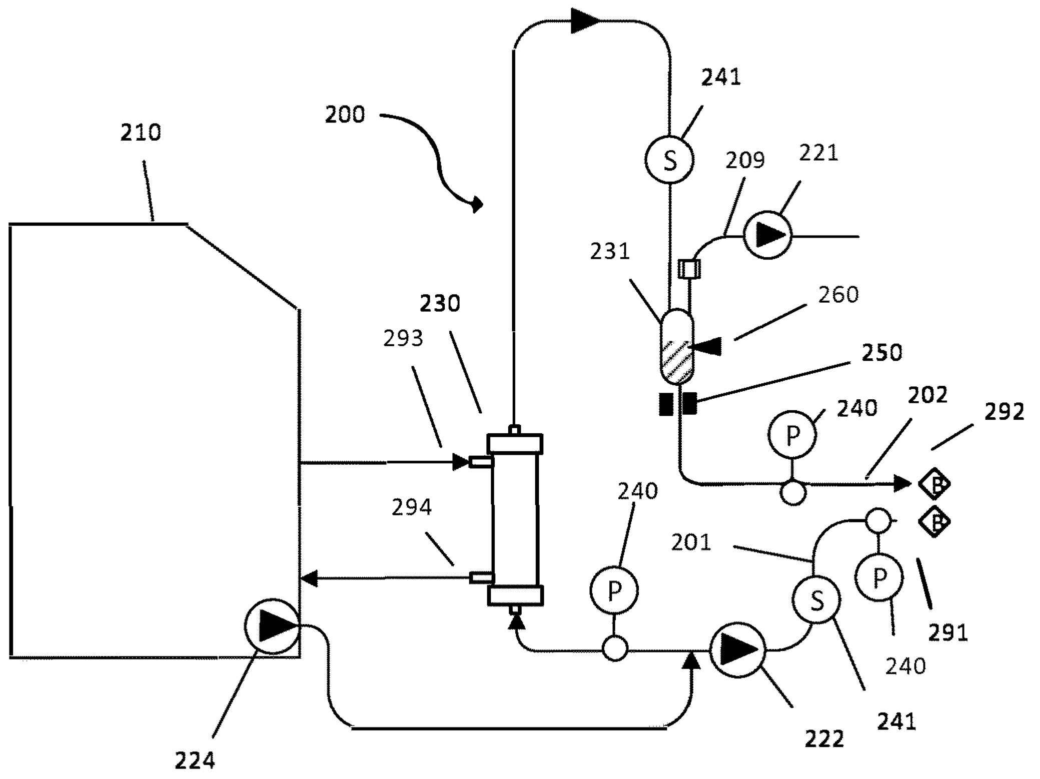
FIG. 6 schematically illustrates a dialysis system of one embodiment in a second state.

Referring to FIG. 6, the arterial line 201 is emptied of fluid immediately after treatment termination. Immediately after treatment termination said arterial line 201 may be substantially filled with blood. Thus, a pushback flow of blood in the direction of the arterial line 201 for emptying of said arterial line 201 may be generated. This pushback flow of blood may be generated by activation of the peristaltic blood pump 222.

Also, rinse-back fluid may be introduced during this state. Thus, rinse-back fluid is introduced into the extracorporeal fluid circuit 200 for filling the fluid circuit 200 prior to the draining of remaining fluid. The rinse-back fluid may be Saline or dialysis fluid.

The dialysis fluid pump may be set to pump approximately 150 ml/min whereby the blood pump may be set to pump so as to achieve a lesser flow i.e. approximately 50 ml/min in order to not create a large pressure inside the arterial line.

This may be performed by activating the dialysis fluid pump 224 so as to generate a flow of the rinse-back fluid in the direction of the venous line 202 through the dialyzer 230. Hence, the rinse-back fluid is pushed through the dialyzer blood line (not shown) of the dialyzer 230 towards the venous line 202, the dialyzer blood line will be described in further detail with reference to FIG. 20. Since the pump 222 generates a pushback flow in the direction of the arterial line 201, said arterial line will be filled with rinse-back fluid. The pushback flow may be in the form of a rinse-back flow.

Figure 7:
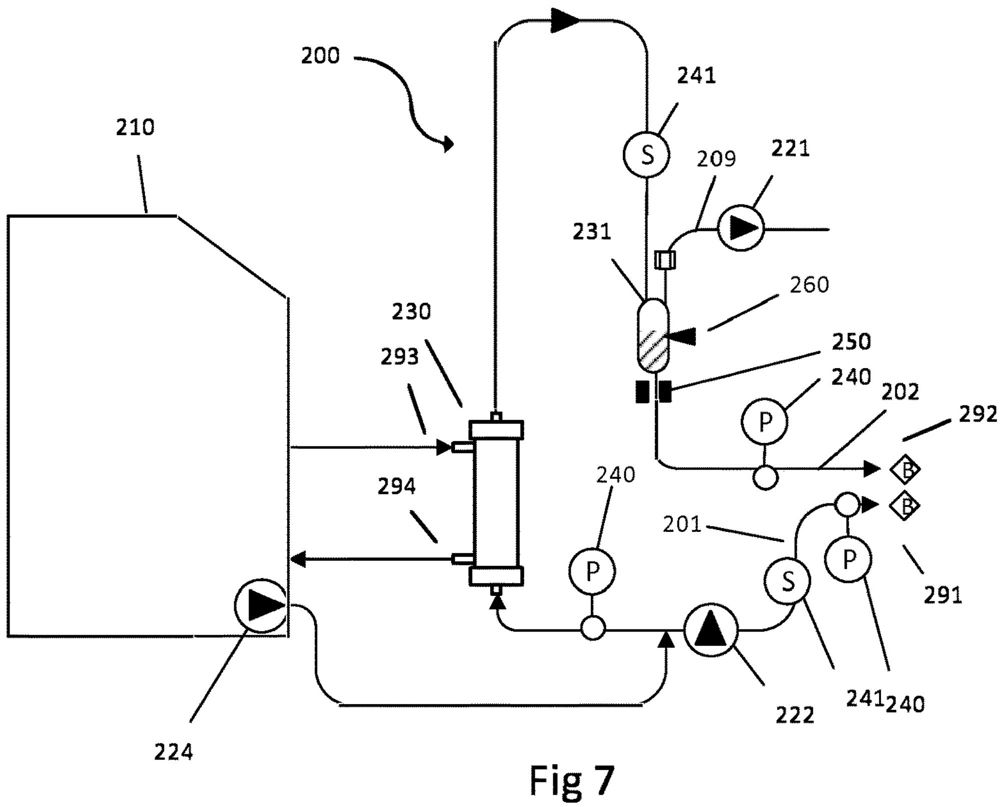
FIG. 7 schematically illustrates a dialysis system of one embodiment in a third state.

As shown in FIG. 7, said peristaltic blood pump 222 may be stopped so as to stop said generating of pushback flow when the arterial line 201 is substantially emptied of blood and instead filled with rinse-back fluid. Due to the design of a conventional peristaltic blood pump 222 this disallows or at least partially prevents fluid communication with the arterial line 201. Instead it is allowed for the rinse-back fluid to flow in the direction of the dialyzer 230 and the venous line 202 and thereby fill the entire fluid circuit 200.

In order to reduce potential waste of blood by draining fluid with a relatively high concentration of blood, the second port 292 may remain in connection with the blood stream of the patient at this point of time in the draining process thus allowing for continuous filling of the extracorporeal fluid circuit 200 until the blood concentration is sufficiently low, i.e. when only small residuals of blood are left in the extracorporeal fluid circuit.

Figure 8:
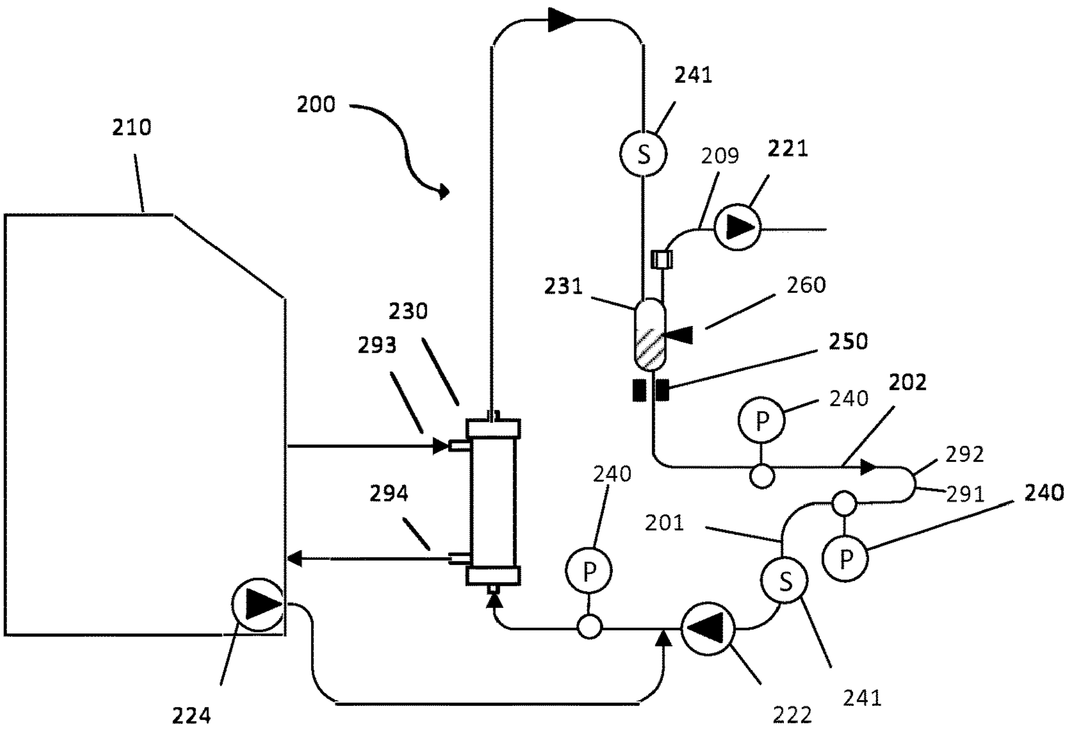
FIG. 8 schematically illustrates a dialysis system of one embodiment in a fourth state.

Referring to FIG. 8, the introduction of rinse-back fluid is achieved by activation of the peristaltic blood pump 222. This process may be performed until the rinse-back fluid substantially fills the extracorporeal fluid circuit 200. During this process, the remaining fluid in the extracorporeal fluid circuit 200 is disallowed to enter the dialyzer fluid circuit 293, 294 either through a balance of flow between the extracorporeal fluid circuit 200 and the dialyzer fluid circuit 293, 294 or through controllable valves substantially disallowing fluid communication between the extracorporeal fluid circuit 200 and the dialyzer fluid circuit 293, 294. Thereby, remaining fluid from the treatment in the extracorporeal fluid circuit 200 is pushed by the rinse-back fluid towards the venous line 292 through the dialyzer 230. Accordingly, remaining fluid from the treatment is pushed by the rinse-back fluid towards the venous line 292 through the dialyzer blood line of the dialyzer 230.

When the extracorporeal fluid circuit 200 is substantially filled with rinse-back fluid the first port 291 and the second port 292 may be connected, e.g. the arterial line 101 and the venous line 102 may be connected, when the extracorporeal fluid circuit 100 is substantially filled with rinse-back fluid. Thus, the extracorporeal fluid circuit becomes a closed-off circuit, allowing for initiation of the removal of the remaining fluid, which at this point may be a mixture of blood from the patient and rinse-back fluid. Notably, at this point there may still be a certain concentration of blood inside the fluid of the extracorporeal fluid circuit 200.

Figure 9:
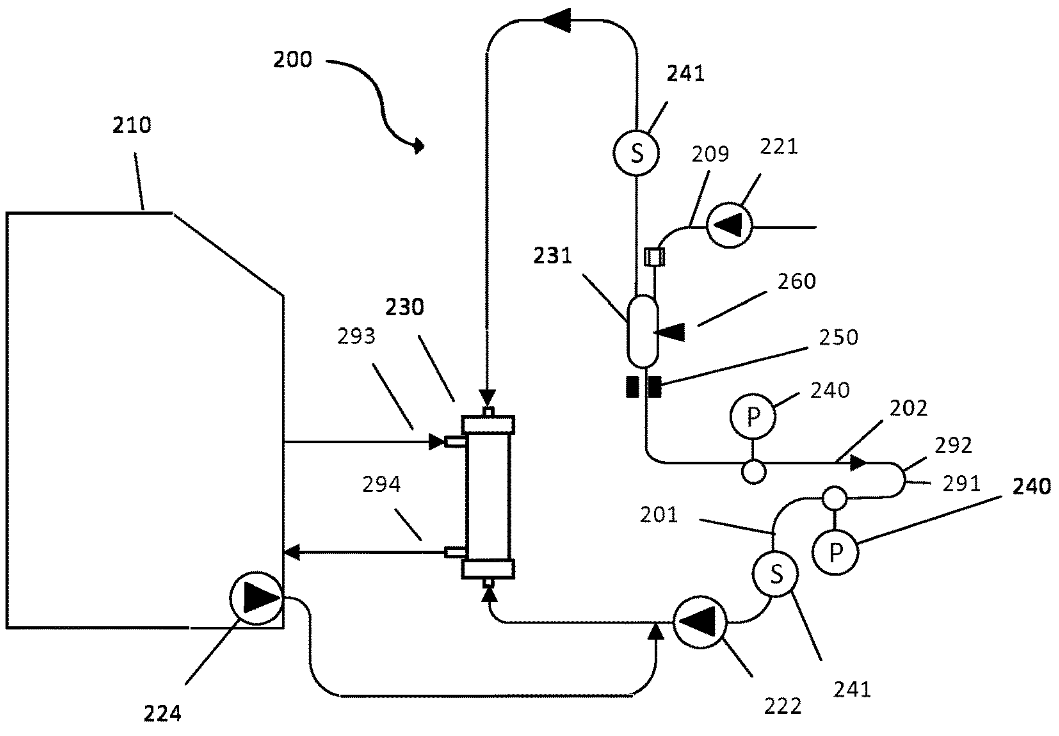
FIG. 9 schematically illustrates a dialysis system of one embodiment in a fifth state.

The extracorporeal fluid circuit is thereafter emptied of remaining fluid, which is schematically depicted in FIG. 9. The draining is initiated by applying a negative pressure on a dialyzer fluid circuit 293, 294 for distribution to and from the dialyzer 230 relative the extracorporeal fluid circuit 200, the dialysis machine 210 being connected to the dialyzer 230 via said dialyzer fluid circuit 293, 294. Said negative pressure forces the rinse-back fluid towards the dialyzer 230 from the venous line 202.

The negative pressure applied on the dialyzer fluid circuit relative the extracorporeal fluid circuit may in other words be considered as inducing a pressure difference between the extracorporeal fluid circuit 200 and the dialyzer fluid circuit 293, 294 to create suction, e.g. flow, of fluid into the dialyzer fluid circuit 293, 294 from the extracorporeal fluid circuit.

The suction and consequential flow of rinse-back flow may be achieved in a number of ways. For example, by selective clamping of the fluid circuit 200 with clamps and flow and suction control or control of the pressure through valve arrangements.

Alternatively, the negative pressure applied on the dialyzer fluid circuit relative the extracorporeal fluid circuit may be applied through introducing of a gas into the extracorporeal fluid circuit 200 via the inlet 209, whereby the remaining fluid is pushed towards the dialyzer 230 for draining through said dialyzer 230.

According to present embodiment, this may be performed with a pumping device 221, such as the air pump 221, connected to the extracorporeal fluid circuit 200 via the inlet 209. Thus, the air pump 221 introduces gas into the extracorporeal fluid 200 so as to ensure the pressure difference between the dialyzer fluid circuit and the extracorporeal fluid circuit 200, thereby forcing the fluid towards the dialyzer.

To remove the remaining fluid, i.e. the rinse-back fluid filling the extracorporeal fluid circuit 200 together with potential residues from the treatment, a net removal of said remaining fluid has to be achieved. This may for example be achieved with the pump arrangement which may be integrated into the dialysis machine, whereby the pump arrangement is controlled so as to achieve said net removal of remaining fluid from the dialyzer 230 and the extracorporeal fluid circuit 200 during the applying of negative pressure. In other words, the negative pressure is a negative driving pressure over the dialyzer membrane from the extracorporeal fluid circuit 200 to dialyzer fluid circuit which may be situated inside the dialysis machine. Said pump arrangement will be further described with reference to FIG. 20.

As is conventional for dialyzers, or dialyzers with wet dialyzer membranes, the membrane of the dialyzer is impermeable for air unless subjected to a very high pressure over the membrane of said dialyzer. Such a high pressure is not achievable with the components commonly used in this field, accordingly there is no risk for the air to enter through the dialyzer 230 and enter the dialysis machine 210.

Furthermore, there is no possibility for the gas flowing through the extracorporeal fluid circuit 200 on each side of the dialyzer 230 to pass through the dialyzer 230 and thereby hinder the pushing of the remaining fluid towards the dialyzer 230 on the opposite side of said dialyzer 230.

If air is present in the dialyzer and there is no fluid (only a wet membrane), the passage through the dialyzer may be closed. That means that if there is any fluid elsewhere in the extracorporeal circuit that fluid cannot be removed. However, as long as there is fluid in the dialyzer that fluid can be removed. Detection of when the dialyzer is "closed" can be done by means of pressure sensors on either side of the dialyzer depending on which side the pressure gradient is created. For example, if the suction is achieved by means of the air pump 221 the pressure may be measured on the extracorporeal side.

Due to the peristaltic blood pump preferably not allowing for flow through it when not activated, said pump 222 may be activated so as to generate a flow of gas i.e. air in the direction of the dialyzer 230. If the blood pump is positioned between the dialyzer 230 and the arterial line 201, said peristaltic blood pump may accordingly generate a flow from the arterial line 201 of the now closed extracorporeal fluid circuit 200 into the dialyzer 230. Thus, the air pump 221 introduces the gas into the closed extracorporeal fluid circuit 200 towards the dialyzer 230 both via the venous line 202 and the arterial line 201, whereby the pumping of the peristaltic blood pump 222 enables the gas i.e. air passing through the arterial line towards the dialyzer 230. The flow of air thus pushes the fluid inside the circuit into the dialyzer 230 according to a similar flow pattern.

The speed of the filling of gas i.e. the speed of the emptying of the extracorporeal fluid circuit 200 may thus be controlled through controlling of the pump arrangement connected to the dialyzer fluid circuit 293, 294, the peristaltic blood pump 222 and the air pump 221.

Accordingly, when the emptying phase has been concluded the entire fluid circuit 200 is filled with gas. Thus the circuit is emptied of fluid due to the net removal of fluid taking place in the dialyzer 230, whereby the extracorporeal fluid circuit 200 may be disposed of without significant spillage or the circuit still containing fluid causing an increased waste disposal cost for the clinic.

Figure 10:
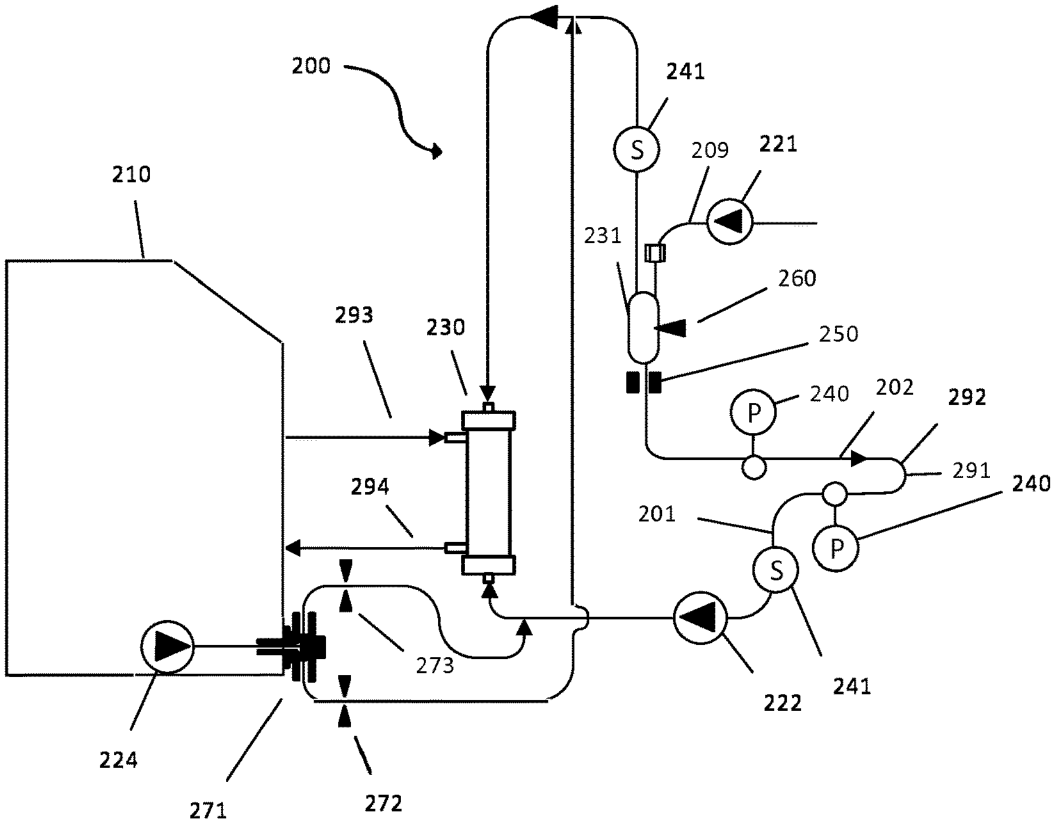
FIG. 10 schematically illustrates a dialysis system of one embodiment.

FIG. 10 depicts an example of a dialysis system. The dialysis system may comprise a check valve 271. The dialysis fluid pump 224 is connected to the extracorporeal fluid circuit 200 via said check valve 271. The check valve 271 serves to allow fluid to flow from the dialysis fluid pump 224 to the extracorporeal fluid circuit 200 while substantially preventing flow back towards the dialysis fluid pump 224. This is particularly important due to the potential risk of cross-contamination of said dialysis fluid pump 224 due to contaminated fluid inside the extracorporeal fluid circuit 200 being sucked back into the pump 224. The check valve will be explained in further detail with reference to FIG. 22.

To further mitigate this risk of contaminating the dialysis fluid pump 224, the check valve 271 may be a disposable check valve, whereby the check valve 271 may be disposed after the fluid circuit 200 has been drained.

To increase the flexibility of the method of draining, usage of the method may be enabled in a dialysis system in a both pre- and post-dilution configuration through a clamp arrangement and additional fluid connections. As depicted in FIG. 10, the dialysis fluid pump 224 is connected to the extracorporeal fluid circuit 200 both downstream and upstream of the dialyzer 230 via a clamp arrangement 272, 273. Thus, both a pre- and post-dilution configuration is enabled by closing and opening of the clamp arrangement 272, 273.

Furthermore, the combination of the check valve 271 and the clamp arrangement 272 and 273 allows for draining of the line connecting the dialysis fluid pump 224 and the extracorporeal fluid circuit 200 without risk for contamination of said dialysis fluid pump 224. By individual control of the clamps of the clamp arrangement 272, 273 selective allowing for gas or fluid to enter the line connected to the dialysis fluid pump 224 can be achieved.

Figure 25:
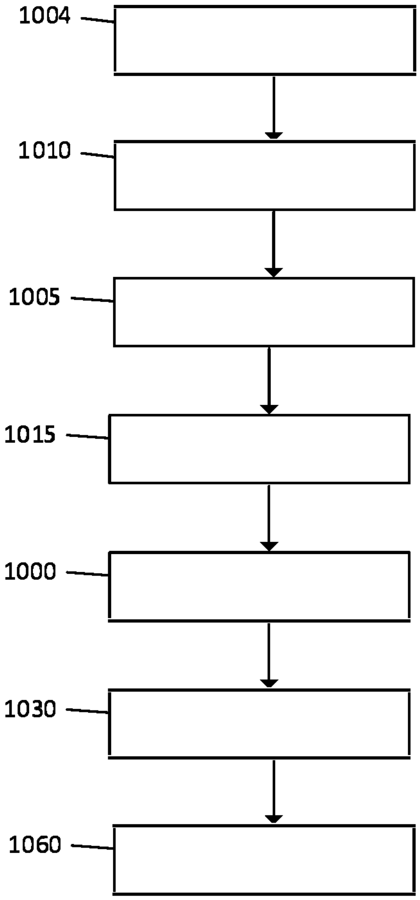
FIG. 25 shows a method for draining an extracorporeal fluid circuit of one embodiment.

FIG. 25 schematically depicts a method for filling an extracorporeal fluid circuit 200 with rinse-back fluid after treatment termination using a dialysis machine 210. The dialysis machine 210 is connected to a dialyzer 230, said extracorporeal fluid circuit 200 and a pumping device 224 connected to the extracorporeal fluid circuit 200. The extracorporeal fluid circuit 200 comprising an arterial line 201 having a first port 291 connectable to a patient, for drawing blood form the patient and a venous line 202 having a second port 292, connectable to the patient, for returning blood to the patient. The method comprising:

pumping rinse-back fluid 2002 into the extracorporeal fluid circuit 200, thereby filling the extracorporeal fluid circuit 200 by activating the pumping device 224 to generate a flow of rinse-back fluid in the direction of the second port 292 through the dialyzer 230.

This allows for a subsequent draining method wherein less of the blood of the patient goes to waste without an increased risk for cross-contamination, due to the rinse-back fluid passing through the dialyzer while the patient still may be connected.

Hence, the method may comprise generating said flow of rinse-back fluid in the direction of the second port through the dialyzer blood line of the dialyzer 230.

The method for filling may further comprise pumping 2001 so as to generate a pushback flow of blood in the direction of the first port 291 so as to substantially empty the arterial line 201 of blood.

Hence, the arterial line is emptied of blood leading to less blood going to waste in the draining process. Furthermore, it allows for an efficient filling of the arterial line 201 with rinse-back fluid.

Figure 26:
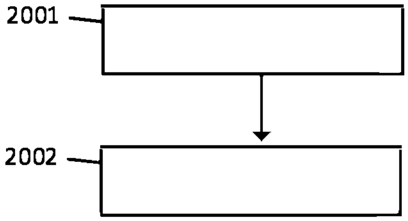
FIG. 26 shows a method for filling an extracorporeal fluid circuit of one embodiment.

Turning to FIG. 26, the dialysis machine 210 is connected to the peristaltic blood pump 222 via the extracorporeal fluid circuit 200, the method may thus further comprising activating 2003 the peristaltic blood pump 222 connected to the extracorporeal fluid circuit 200 to further generate flow of rinse-back fluid in the direction of the second port 292.

The push back flow may be generated by the peristaltic blood pump 222. Consequentially, the generating 2003, i.e. the step of generating, of the pushback flow comprises activating the peristaltic blood pump 222 so as to generate the pushback flow and stopping 2004 said peristaltic blood pump 222 so as to stop said pumping of pushback flow when the arterial line 201 is substantially emptied of blood.

The pumping device 224 may be connected to the extracorporeal fluid circuit 200 via the clamp arrangement 272, 273 both downstream and upstream of the dialyzer 230. Further, the dialysis fluid pump 224 may be connected to the extracorporeal fluid circuit 200 via the check valve 271.

Thus, the risk for cross-contamination is significantly reduced since no potentially contaminated fluid is allowed to be sucked in by the dialysis fluid pump and cause a contamination of the extracorporeal fluid circuit during later treatments.

Figure 27:
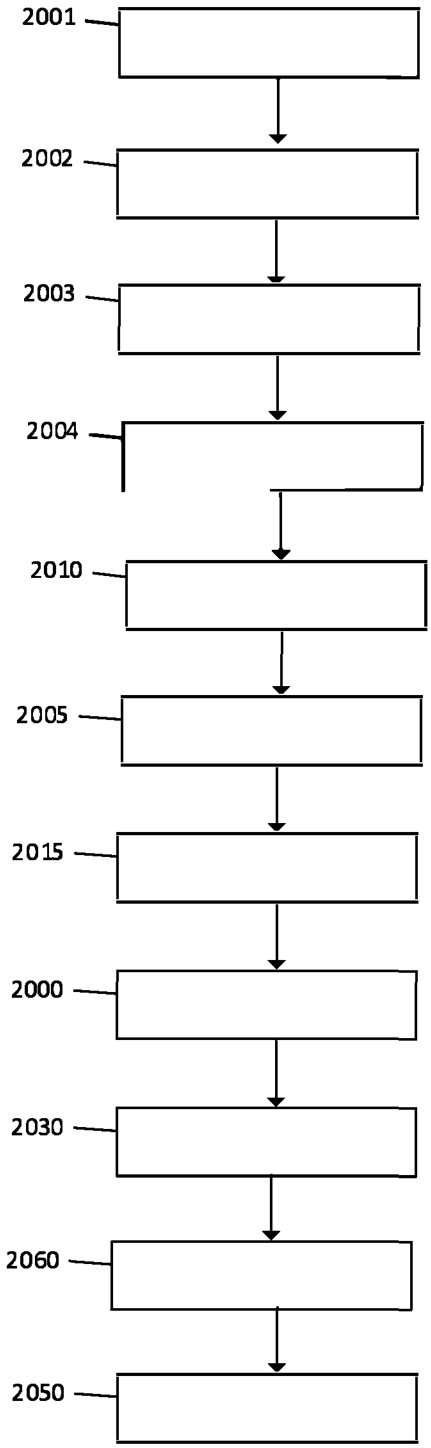
FIG. 27 shows a method for draining an extracorporeal fluid circuit of one embodiment.

Referring to FIG. 27, the method for filling may further comprise releasing 2002 said clamp arrangement 272, 273 forming fluid communication between the pumping device 224 and the extracorporeal fluid circuit 200 prior to the pumping of the rinse-back fluid into said extracorporeal fluid circuit 200.

Thereby a more flexible filling method may be achieved since the method is made suitable both for a dialysis system with a post-dilution configuration as well as a dialysis system with a pre-dilution configuration.

The method may further comprise preventing fluid flow back to the pumping device 224 with the check valve 271.

Thus, the risk for cross-contamination is significantly reduced since no potentially contaminated fluid is allowed to be sucked in by the dialysis fluid pump and cause a contamination of the extracorporeal fluid circuit during later treatments.

The rinse-back fluid may for example be Saline or dialysis fluid, whereby the pumping device 224 may be arranged to provide saline or dialysis fluid to the extracorporeal fluid circuit 200 through being connected to a saline or dialysis fluid supply.

The pumping device 224 may be a dialysis fluid pump, the dialysis fluid pump being arranged to provide dialysis fluid to the extracorporeal fluid circuit 200. Accordingly, the rinse-back fluid may be dialysis fluid. Thereby, the method for filling may be performed by a conventional dialysis system with a dialysis fluid pump for providing dialysis fluid to the extracorporeal fluid circuit. Hence, a method for filling which may be performed by a conventional dialysis system without requiring additional components is achieved.

Further, this allows for rinsing and emptying of the fluid line connecting the dialysis fluid pump 224 and the extracorporeal fluid circuit 200 since the rinse-back fluid in the form of dialysis fluid may be sucked through the dialyzer 230. Thereby, the fluid line connecting the dialysis fluid pump 224 may be emptied by simply stopping the provision of rinse-back fluid while a net removal of rinse-back is performed in the dialyzer 230. Hence, said fluid line may be disposed if in a manner similar to the disposing of the extracorporeal fluid circuit 200. The net removal may be performed by means of conveying the rinse-back fluid towards the drain of the dialysis machine via the dialyzer fluid circuit.

The aforementioned steps of filling may constitute a part of the method for draining the extracorporeal fluid circuit utilizing the dialysis machine 210, which is schematically depicted in FIG. 27.

The dialysis machine 210 is connected to the dialyzer 230 and said extracorporeal fluid circuit 200, said extracorporeal fluid circuit 200 comprising an arterial line 201 connectable to a patient, for drawing blood from the patient and a venous line 202 connectable to the patient for returning blood to the patient. The method comprising the step of:

after treatment termination from said extracorporeal fluid circuit 210 draining 2000 remaining fluid from said extracorporeal fluid circuit through the dialyzer 230.

The draining through the dialyzer allows for the dialysis machine, i.e. the drain and pump arrangement, to handle the remaining fluid in the extracorporeal fluid circuit.

Thereby the operator is not subjected to contaminated fluid in the process of emptying the extracorporeal fluid circuit, since said fluid circuit does not have to be emptied by hand into a sink or a bucket. Thus, a safer and more user-friendly draining process is achieved.

To avoid subjection to contaminated fluid for the operator the entire fluid circuit may also be sealed by clamps and disposed of. However this increases the weight of the disposed material considerably leading to higher costs for the clinic. Accordingly, the draining through the dialyzer thus enables draining without subjecting the operator to contaminated fluid in a cost-efficient manner since the fluid circuit can be substantially drained of fluid before disposal.

Treatment termination refers to a state where the dialysis treatment has been interrupted or completed. In other words, the method of draining is performed after said dialysis treatment has been interrupted or completed.

The method may comprise to after treatment termination from said extracorporeal fluid circuit 210 drain 2000 remaining fluid from said extracorporeal fluid circuit through the dialyzer fluid circuit 293, 294 of dialyzer 230.

To drain the remaining fluid through the dialyzer a pressure difference between the dialyzer fluid circuit 293, 294 and the extracorporeal fluid circuit 200 may be applied. The dialyzer 230 is connected to the dialysis machine 210 via a dialyzer fluid circuit 293, 294 for distribution of dialysis fluid to and from the dialyzer 230, whereby the extracorporeal fluid circuit 210 is drained through the dialyzer 230 by applying a negative pressure on the dialyzer fluid circuit 293, 294 relative the extracorporeal fluid circuit. Thereby, the remaining fluid is forced towards and through the dialyzer in a stable and robust manner.

The negative pressure may be applied when the patient is disconnected. Accordingly, substantially no blood is drawn from the patient when the remaining fluid is drained through the dialyzer.

The negative pressure may be applied by introducing of gas into the extracorporeal fluid circuit 200. the introducing of the gas is performed by pumping of gas into the extracorporeal fluid circuit 200 via the inlet 209, wherein the remaining fluid is pushed towards the dialyzer 230 for draining through the dialysis machine.

The gas may be pumped into the extracorporeal fluid circuit 200 with a pumping device 221 connected to the extracorporeal fluid circuit 200 via the inlet 209. Hence, the method can be performed by an existing conventional dialysis system with an air pump without requiring additional components increasing the complexity of the dialysis system.

The method may further comprise introducing a rinse-back fluid 2010 into the extracorporeal fluid circuit 200 prior to the draining 2000 for filling the extracorporeal fluid circuit 200.

The introduction of the rinse-back fluid enables blood still in the extracorporeal fluid circuit to be returned. Thereby, the draining method may be performed without blood still in the circuit going to waste.

This may be performed by the dialysis fluid pump 224. The dialysis machine 210 is thus connected to a dialysis fluid pump 224 connected to the extracorporeal fluid circuit 200, wherein introducing of the rinse-back fluid into the extracorporeal fluid circuit 200 to fill said extracorporeal fluid circuit 200 is performed by activating a dialysis fluid pump 224 so as to generate a flow of the rinse-back fluid in the direction of the venous line 202 through the dialyzer 230. Accordingly, the rinse-back fluid is led via the dialyzer blood line of the dialyzer towards the venous line.

Thereby, a method for draining with the aforementioned advantages which may be executed by a dialysis system provided with a dialysis fluid pump is achieved. Furthermore, a method for draining which enables draining of the fluid line connecting the dialysis fluid pump 224 and the extracorporeal fluid circuit 200 is achieved, which may increase the efficiency of the draining.

The dialyzer 230 is connected to the pump arrangement 63, 64 for distribution of dialysis fluid to and from the dialyzer 230. The method may thus further comprise controlling 2030 the pump arrangement 63, 64 to achieve a net removal of remaining fluid from the dialyzer 230 and the extracorporeal fluid circuit 200 during the applying of negative pressure. Said net removal consequently causes the extracorporeal fluid circuit to gradually empty so as to enable the disposal of said extracorporeal fluid circuit 200 at a later stage.

To generate a flow of the rinse-back fluid in the direction of the dialyzer 230, the method may further comprise activating 2005 the peristaltic blood pump 222 to generate a flow of the rinse-back fluid in the direction of the dialyzer 230 after the rinse-back fluid has been introduced 2010.

Before removal of the remaining fluid through the dialyzer 230, the extracorporeal fluid circuit 200 is closed. Accordingly, the method may further comprise connecting 2015 the first port 291 to the second port 292 prior to introducing the gas into the extracorporeal fluid circuit 200.

The closing of the fluid circuit effectively reduces the risk for spillage of fluid from the fluid circuit during draining, whereby the risk for infection due to contamination is reduced greatly. Further, the mitigated risk for spillage allows for a more user-friendly draining process.

After draining 2000 the remaining fluid through the dialyzer 130, the remaining fluid may be led out through a drain 68 (which will be further described with reference to FIG. 20). Accordingly, the method may further comprise conveying 2060 the remaining fluid removed from the extracorporeal fluid circuit 200 to a drain 68 of the dialysis machine 210. The drain 68 may be connected to the dialyzer fluid circuit 293, 294.

The method may further comprise conveying 2060 the remaining fluid removed from the extracorporeal fluid circuit to the drain 68 of the dialysis machine 110 via the dialyzer fluid circuit 293, 294.

This may be performed immediately after the controlling 2030 of the pump arrangement 63, 64 to achieve the net removal of remaining fluid from the dialyzer 230.

As partly previously described, the method may further comprise generating 2003 the pushback flow of blood in the direction of the arterial line 201 for emptying of the arterial line 201 of blood prior to the generating the flow of the rinse-back fluid in the direction of the dialyzer 230. The arterial line is thus emptied of blood leading to less blood going to waste in the draining process. Furthermore, it allows for an efficient filling of the arterial line 201 with rinse-back fluid.

Hence, the method may further comprise activating the peristaltic blood pump 222 so as to generate the pushback flow and stopping 2004 said peristaltic blood pump 222 so as to stop said generating of pushback flow when the arterial line 201 is substantially emptied of blood. The method may thus be performed by a conventional dialysis system without requiring additional components.

As depicted in FIG. 10, the dialysis fluid pump 224 may be connected to the fluid circuit via the check valve 271, the method may accordingly further comprise preventing fluid flow back to the dialysis fluid pump 224 with the check valve 271. Thus, the risk for cross-contamination is significantly reduced since no potentially contaminated fluid is allowed to be sucked in by the dialysis fluid pump and thereby cause a contamination of the extracorporeal fluid circuit during later treatments.

Further, the method may comprise disposing 2050 said check valve 271 after the extracorporeal fluid 200 is filled with gas, whereby the risk for cross-contamination is substantially reduced or even eliminated.

The method may also comprise releasing 2002 the clamp arrangement 272, 273 forming fluid communication between the dialysis fluid pump 224 and the extracorporeal fluid circuit 200 prior to the introduction of the rinse-back fluid into said extracorporeal fluid circuit 200.

Thereby a more flexible draining method may be achieved since the method is made suitable both for a dialysis system with a post-dilution configuration as well as a dialysis system with a pre-dilution configuration. Furthermore, the provision and selective releasing of said clamps allows for controlling the gas flow or the fluid flow in the fluid line connecting the dialysis fluid pump 224 and the extracorporeal circuit 200, whereby said fluid line may be drained as well. Alternatively, the clamps allows for controlling the gas flow as well as the fluid flow in said fluid line.

Figure 11:
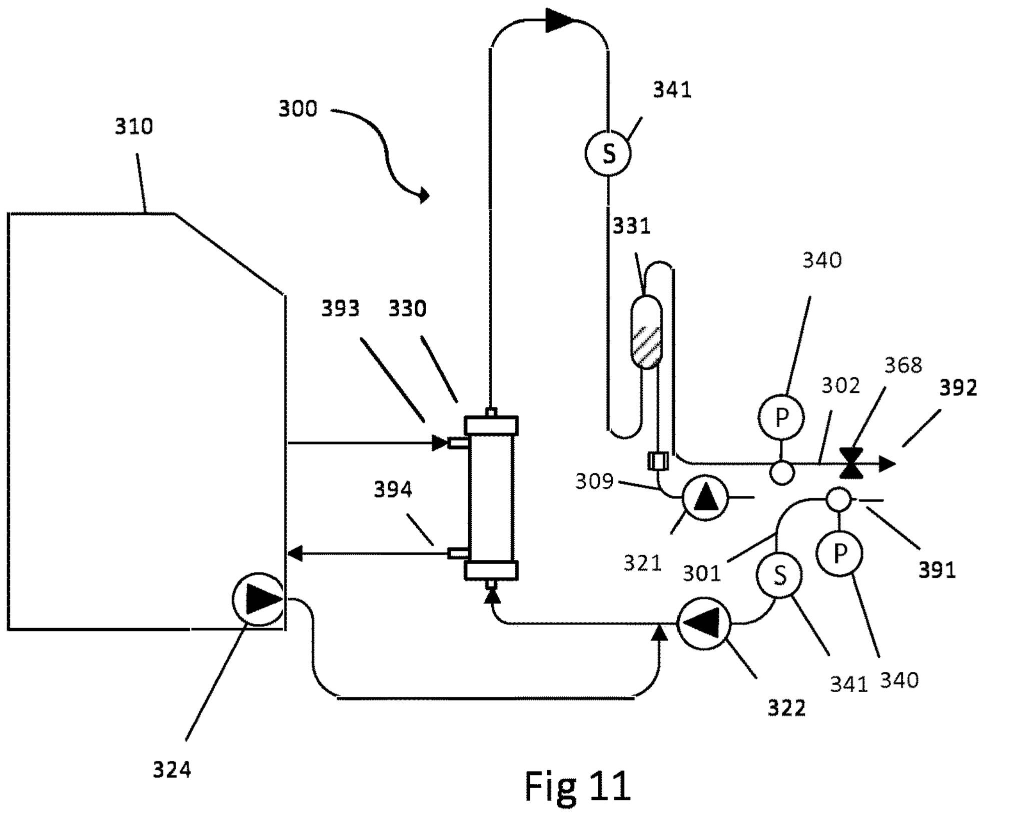
FIG. 11 schematically illustrates a dialysis system of one embodiment in a first state.
Figure 12:
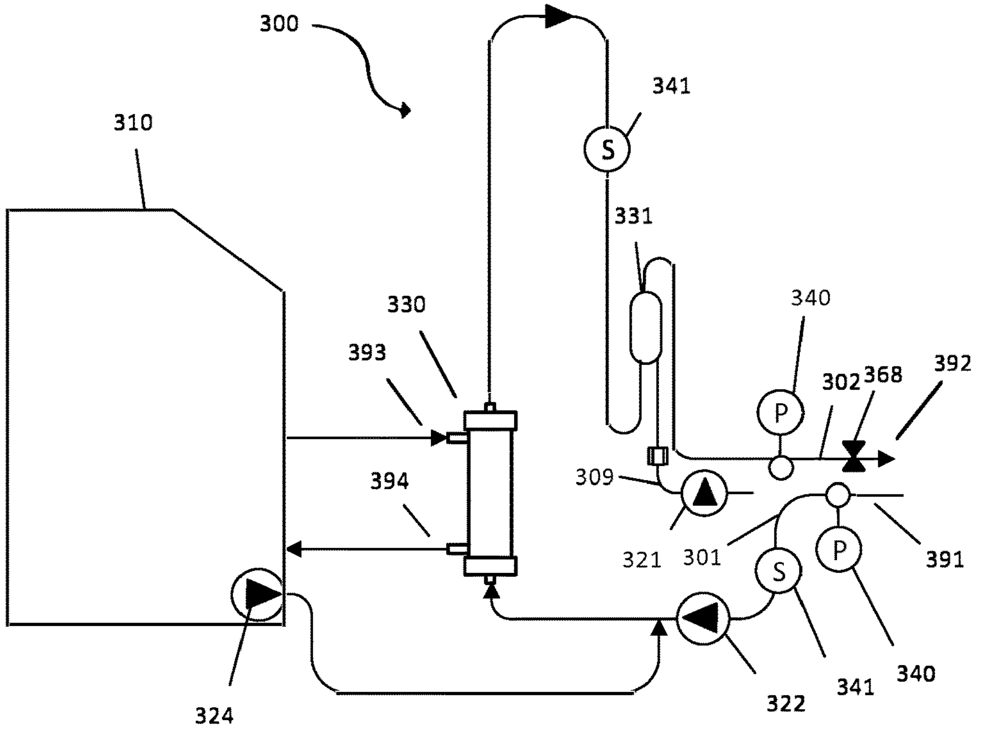
FIG. 12 schematically illustrates a dialysis system of one embodiment in a second state.
Figure 13:
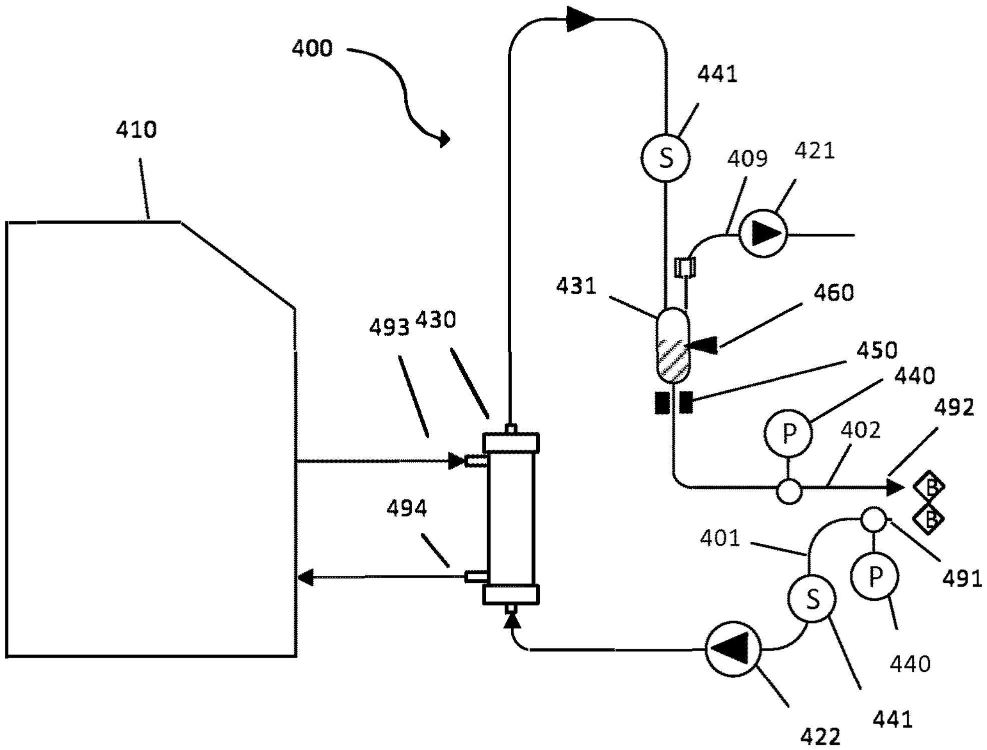
FIG. 13 schematically illustrates a dialysis system of one embodiment in a first state.

FIG. 11-12 schematically illustrates a dialysis system sharing all of the structural features of the embodiment shown in FIG. 5-10. However, the dialysis system utilizer a free-end draining process, whereby the arterial line and venous line remains disconnected throughout the draining.

Referring to FIG. 11, the dialysis system comprises a dialysis machine 310 connected to an extracorporeal fluid circuit 300 and a dialyzer 330, wherein said extracorporeal fluid circuit 300 comprises an arterial line 301 connectable to a patient for drawing blood form the patient and a venous line 302 connectable to the patient for returning blood to the patient, said dialysis system being configured to perform the method for draining.

Connected to the extracorporeal fluid circuit is a peristaltic blood pump 322. The blood pump may be arranged to generate a flow both in the direction of the first port 391 i.e. the arterial line 301 as well as the second port 392 i.e. the venous line 302. Further, the peristaltic pump disallows flow or at least substantially prevent flow when the pump is not activated.

The dialysis machine 310 is connected to the dialyzer 330 via a first dialyzer line 393 and a second dialyzer line 394 forming a dialyzer fluid circuit. The dialyzer in turn is connected to the extracorporeal fluid circuit 300.

In order to provide the distribution of dialysis fluid to and from the dialyzer required for HDF-dialysis or HD-dialysis the dialyzer may be connected to a pump arrangement via the dialyzer fluid circuit 393, 394. Said pump arrangement is arranged to control the distribution of dialysis fluid into and from the extracorporeal fluid circuit via the dialyzer 330 and will be more closely described with reference to FIG. 20.

Further, the pump arrangement may be accompanied by a dialysis fluid pump 324. Hence, the dialysis machine 310 is connected to the dialysis fluid pump 324, which in turn is connected to the extracorporeal fluid circuit 300. The dialysis fluid pump 324 may be connected to the extracorporeal circuit 300 at a position between the peristaltic blood pump 322 and the dialyzer 330. However as the skilled person realizes, the dialysis fluid pump 324 may be connected at several positions in the extracorporeal fluid circuit 300.

The fluid circuit 300 is connected to an air pump 321 via an inlet 309 connected to the fluid circuit 300, for example via a venous drip chamber 331 situated between the dialyzer 330 and the second port 392. Hence, the air pump 321 may be connected to the venous line 302.

As is well-known for the skilled person, the extracorporeal fluid circuit 300 may comprise a pressure sensor 340 for monitoring the pressure inside the extracorporeal fluid circuit.

Further, the extracorporeal fluid circuit may comprise a sample port 341 for extracting blood samples or dialysis fluid samples.

Referring to FIG. 11, the dialysis system is depicted in a state where the patient is disconnected from the first port 391 and the second port 392, whereby said ports are free ends of the extracorporeal fluid circuit. At this point the method for draining differs from the previously described in that the ports are not connected in order to empty the extracorporeal fluid circuit. To this point however, each state and action depicted and described with reference to FIG. 5-7 has been undergone and performed.

The draining is initiated by applying a negative pressure on a dialyzer fluid circuit 393, 394 for distribution to and from the dialyzer 330 relative the extracorporeal fluid circuit 300, the dialysis machine 310 being connected to the dialyzer 330 via said dialyzer fluid circuit 393, 394. Said negative pressure forces the rinse-back fluid towards the dialyzer 330 from the venous line 302.

The negative pressure applied on the dialyzer fluid circuit relative the extracorporeal fluid circuit may in other words be considered as inducing a pressure difference between the extracorporeal fluid circuit 300 and the dialyzer fluid circuit 393, 394 to create suction, e.g. flow, of fluid into the dialyzer fluid circuit 393, 394 from the extracorporeal fluid circuit.

The suction and consequential flow of rinse-back flow may be achieved in a number of ways. For example, by selective clamping of the fluid circuit 300 with clamps and flow and suction control or control of the pressure through valve arrangements.

Alternatively, the negative pressure applied on the dialyzer fluid circuit relative the extracorporeal fluid circuit may be applied through introducing of a gas into the extracorporeal fluid circuit 300 via an inlet, whereby the remaining fluid is pushed towards the dialyzer 330 for draining through said dialyzer 330.

According to this embodiment, the inlet for the gas may be any or both of the free ends of the fluid circuit 300 i.e. any or both of the first port 391 and the second port 392.

To allow for the remaining fluid to be drained through the dialyzer 330 and flow towards said dialyzer, the venous drip chamber 331 is turned around, i.e. turned upside down, for emptying of said venous drip chamber of remaining fluid and thereby introduce gas into the extracorporeal fluid circuit 300. Thus, the remaining fluid is forced from the venous line 302 towards the dialyzer, whereby the venous line 302 instead is filled with air via the second port 392.

In order to introduce the gas into the extracorporeal fluid circuit 300 the peristaltic blood pump 322 may be activated. By activating said blood pump 322 to create a flow the direction of the dialyzer 330 gas is sucked through the first port 391. Optionally, the gas comprises air from the surrounding room.

As is conventional for dialyzers, or dialyzers with wet dialyzer membranes, the membrane of the dialyzer is impermeable for air unless subjected to a very high pressure over the membrane of said dialyzer. Such a high pressure is not achievable with the components commonly used in this field, accordingly there is no risk for the air to enter through the dialyzer 330 and enter the dialysis machine 310.

Furthermore, there is no possibility for the gas flowing through the extracorporeal fluid circuit 300 on each side of the dialyzer 330 to pass through the dialyzer 330 and thereby hinder the pushing of the remaining fluid towards the dialyzer 330 on the opposite side of said dialyzer 330.

If air is present in the dialyzer and there is no fluid (only a wet membrane), the passage through the dialyzer may be closed. That means that if there is any fluid elsewhere in the extracorporeal circuit that fluid cannot be removed. However, as long as there is fluid in the dialyzer that fluid can be removed. Detection of when the dialyzer is "closed" can be done by means of pressure sensors on either side of the dialyzer depending on which side the pressure gradient is created. For example, if the suction is achieved by means of the air pump 321 the pressure may be measured on the extracorporeal side.

The risk for spillage of the remaining fluid may be greatly reduced by locking of a clamp 368 to the second port 392 after the rinse-back fluid has been introduced into the extracorporeal fluid circuit 300. However, said clamp 368 has to be released prior to sucking in the gas via the first port 391.

After the turning of the venous drip chamber 331, all of the remaining fluid in the venous line 302 is forced to flow towards the dialyzer 330 and exit through a drain (not shown) of the dialysis machine 310. This in conjunction with the pumping of air through the arterial line 301 fills the entire fluid circuit with air, thereby draining all of the remaining fluid through the dialyzer 330, this state is shown in FIG. 12 where the venous drip chamber 331 is substantially filled with air. Thereafter, the empty extracorporeal fluid circuit may be disposed of.

This may be achieved by means of conveying the rinse-back fluid towards the drain of the dialysis machine via the dialyzer fluid circuit.

Figure 28:
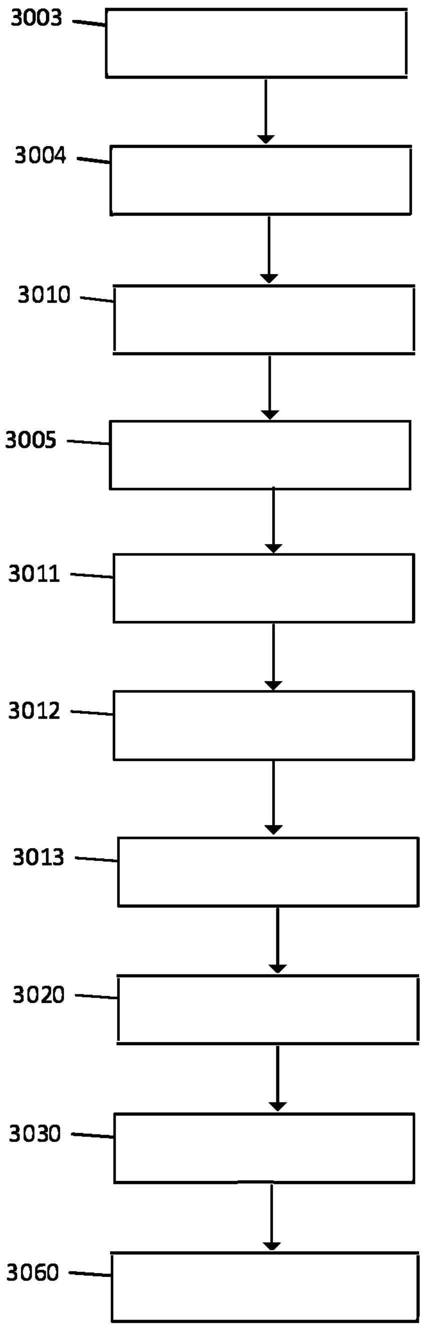
FIG. 28 shows a method for draining an extracorporeal fluid circuit of one embodiment.

FIG. 28 shows a schematic view of a method of draining the extracorporeal fluid circuit 300 utilizing a dialysis machine 310. The dialysis machine 310 is connected to the dialyzer 330 and said extracorporeal fluid circuit 300, said extracorporeal fluid circuit 300 comprising an arterial line 301 connectable to a patient, for drawing blood from the patient and a venous line 302 connectable to the patient for returning blood to the patient. The method comprising the step of:

after treatment termination from said extracorporeal fluid circuit 310 draining 3000 remaining fluid from said extracorporeal fluid circuit through the dialyzer 330.

The draining through the dialyzer allows for the dialysis machine, i.e. the drain and pump, to handle the remaining fluid in the extracorporeal fluid circuit.

Thereby the operator does not have to be subjected to contaminated fluid in the process of emptying the extracorporeal fluid circuit, since said fluid circuit does not have to be emptied by hand into a sink or a bucket. Thus, a safer and more user-friendly draining process is achieved.

To avoid subjection to contaminated fluid for the operator the entire fluid circuit may also be sealed by clamps and disposed of. However this increases the weight of the disposed material considerably leading to higher costs for the clinic. Accordingly, the draining through the dialyzer thus enables draining without subjecting the operator to contaminated fluid in a cost-efficient manner since the fluid circuit can be substantially drained of fluid before disposal.

Treatment termination refers to a state where the dialysis treatment has been interrupted or completed. In other words, the method of draining is performed after said dialysis treatment has been interrupted or completed.

The method may comprise to after treatment termination from said extracorporeal fluid circuit 310 draining 3000 remaining fluid from said extracorporeal fluid circuit through the dialyzer fluid circuit 393, 394 of dialyzer 330.

To drain the remaining fluid through the dialyzer 330 a pressure difference between the dialyzer fluid circuit 393, 394 and the extracorporeal fluid circuit 300 may be applied. The dialyzer 330 is connected to the dialysis machine 310 via a dialyzer fluid circuit 393, 394 for distribution of dialysis fluid to and from the dialyzer 330, whereby the extracorporeal fluid circuit 310 is drained through the dialyzer 330 by applying a negative pressure on the dialyzer fluid circuit 393, 394 relative the extracorporeal fluid circuit. Thereby, the remaining fluid is forced towards and through the dialyzer in a stable and robust manner.

The negative pressure may be applied when the patient is disconnected. Accordingly, substantially no blood is drawn from the patient when the remaining fluid is drained through the dialyzer. The negative pressure may be applied by introducing of gas into the extracorporeal fluid circuit 300. the introducing of the gas is performed by pumping of gas into the extracorporeal fluid circuit 300 via the inlet 309, wherein the remaining fluid is pushed towards the dialyzer 330 for draining through the dialysis machine.

The gas may be pumped into the extracorporeal fluid circuit 300 with a pumping device 321 connected to the extracorporeal fluid circuit 300 via the inlet 309 or the first port forming the inlet 391.

The method may further comprise introducing a rinse-back fluid 3010 into the extracorporeal fluid circuit 300 prior to the draining 3000 for filling the extracorporeal fluid circuit 300. Hence, the method can be performed by an existing conventional dialysis system without requiring additional components increasing the complexity of the dialysis system.

The introduction of the rinse-back fluid enables blood still in the extracorporeal fluid circuit to be returned. Thereby, the draining method may be performed without blood still in the circuit going to waste by not being returned to the patient.

This may be performed by the dialysis fluid pump 324. The dialysis machine 310 is thus connected to a dialysis fluid pump 324 connected to the extracorporeal fluid circuit 300, wherein introducing of the rinse-back fluid into the extracorporeal fluid circuit 300 to fill said extracorporeal fluid circuit 300 is performed by activating a dialysis fluid pump 324 so as to generate a flow of the rinse-back fluid in the direction of the venous line 302 through the dialyzer 330. Accordingly, the rinse-back fluid is led via the dialyzer blood line of the dialyzer towards the venous line. Thereby, a method for draining with the aforementioned advantages which may be executed by a dialysis system provided with a dialysis fluid pump is achieved. Furthermore, a method for draining which enables draining of the fluid line connecting the dialysis fluid pump 324 and the extracorporeal fluid circuit is achieved, which may increase the efficiency of the draining.

The dialyzer 330 is connected to the pump arrangement 63, 64 for distribution of dialysis fluid to and from the dialyzer 330. The method may thus further comprise controlling 3030 the pump arrangement 63, 64 to achieve a net removal of remaining fluid from the dialyzer 330 and the extracorporeal fluid circuit 300 during the applying of negative pressure. Said net removal consequently causes the extracorporeal fluid circuit to gradually empty so as to enable the disposal of said extracorporeal fluid circuit 300 at a later stage.

To generate a flow of the rinse-back fluid in the direction the dialyzer 330, the method may further comprise activating 3005 the peristaltic blood pump 322 to generate a flow of the rinse-back fluid in the direction of the dialyzer 330 after the rinse-back fluid has been introduced 3010. The dialysis machine 310 being connected to the peristaltic blood pump 322.

After draining 3000 the remaining fluid through the dialyzer 330, the remaining fluid may be led out through a drain 68 (which will be further described with reference to FIG. 20). Accordingly, the method may further comprise conveying 3060 the remaining fluid removed from the extracorporeal fluid circuit 300 to a drain 68 of the dialysis machine 310. The drain 68 may be connected to the dialyzer fluid circuit 393, 394.

The method may further comprise conveying 3060 the remaining fluid removed from the extracorporeal fluid circuit to the drain 68 of the dialysis machine 110 via the dialyzer fluid circuit 393, 394.

This may be performed immediately after the controlling 3030 of the pump arrangement 63, 64 to achieve the net removal of remaining fluid from the dialyzer 330.

To empty the extracorporeal fluid circuit 300, the method may further comprise turning 3013 the venous drip chamber 331 connected to the venous line 302 for emptying said venous drip chamber 331 of remaining fluid so as to introduce gas into the extracorporeal fluid circuit 300.

The gas may also be introduced into the extracorporeal fluid circuit 300 by activation of the peristaltic blood pump 322 to suck gas into the extracorporeal fluid circuit 300 via the first port 391.

Thereby both the venous line 302 and the arterial line 301 may be filled with gas effectively forcing all of the remaining fluid into the dialyzer 330. In comparison to the connecting of the ports required in the previously described embodiments for filling the extracorporeal fluid circuit with gas this does not pose any demanding requirements on the design of the ports. With some ports additional components such as adapters may be required in order to achieve the connection in a proper manner. Instead, the gas may be introduced directly into the fluid circuit without the additional step of connecting the ports, whereby a more user-friendly draining method is achieved. Furthermore it may be performed using almost any type of conventional dialysis system since it does not require specific ports suitable for connecting.

The risk for spillage may be reduced by the method further comprising locking 3011 a clamp 368 to the second port 392 after introducing 3010 the extracorporeal fluid circuit 300 with said rinse-back fluid and releasing 3012 said clamp 368 prior to sucking the gas into the fluid circuit via the first port 391.

The method may further comprise generating 3003 the pushback flow of blood in the direction of the arterial line 301 for emptying of the arterial line 301 of blood prior to the generating the flow of the rinse-back fluid in the direction of the dialyzer 330. The arterial line is thus emptied of blood leading to less blood going to waste in the draining process. Furthermore, it allows for an efficient filling of the arterial line 201 with rinse-back fluid.

Hence, the method may further comprise activating the peristaltic blood pump 322 so as to generate the pushback flow and stopping 3004 said peristaltic blood pump 322 so as to stop said generating of pushback flow when the arterial line 301 is substantially emptied of blood.

Similar to the embodiment depicted in FIG. 10, the dialysis fluid pump 324 may be connected to the fluid circuit via a check valve, the method may accordingly further comprise preventing fluid flow back to the dialysis fluid pump 324 with the check valve. Further, the method may comprise disposing 3050 said check valve after the extracorporeal fluid 300 is filled with gas.

The extracorporeal fluid circuit 300 disclosed in FIG. 11-12 may also be filled with rinse-back fluid after treatment termination by utilizing the dialysis machine 310 according to the previously described filling method depicted in FIG. 26-27.

Accordingly, the dialysis machine 310 is connected to the dialyzer 330, said extracorporeal fluid circuit 300 and the pumping device 324 connected to the extracorporeal fluid circuit 300. The extracorporeal fluid circuit 300 comprises an arterial line 301 having a first port 391 connectable to a patient, for drawing blood from the patient and a venous line 302 having a second port 392, connectable to the patient, for returning blood to the patient. The method comprising:

pumping rinse-back fluid 2002 into the extracorporeal fluid circuit 300, thereby filling the extracorporeal fluid circuit 300 by activating the pumping device 324 to generate a flow of rinse-back fluid in the direction of the second port 392 through the dialyzer 330.

This allows for a subsequent draining method wherein less of the blood of the patient goes to waste without an increased risk for cross-contamination, due to the rinse-back fluid passing through the dialyzer while the patient still may be connected.

Hence, the method may comprise generating said flow of rinse-back fluid in the direction of the second port through the dialyzer blood line of the dialyzer 330. The flow of rinse-back fluid may hence be generated through the dialyzer blood line to the venous line.

The method for filling may further comprise pumping 2001 so as to generate a pushback flow of blood in the direction of the first port 391 so as to substantially empty the arterial line 301 of blood.

Hence, the arterial line is emptied of blood leading to less blood going to waste in the draining process. Furthermore, it allows for an efficient filling of the arterial line 201 with rinse-back fluid.

The dialysis machine 310 is connected to the peristaltic blood pump 322 via the extracorporeal fluid circuit 300, the method may thus further comprising activating 2003 the peristaltic blood pump 322 connected to the extracorporeal fluid circuit 300 to further generate flow of rinse-back fluid in the direction of the second port 392.

The pushback flow may be generated by the peristaltic blood pump 322. Consequentially, the generating 2003, i.e. the step of generating, of the pushback flow comprises activating the peristaltic blood pump 322 so as to generate the pushback flow and stopping 3004 said peristaltic blood pump 322 so as to stop said pumping of pushback flow when the arterial line 301 is substantially emptied of blood.

Hence, the arterial line is emptied of blood leading to less blood going to waste in the draining process. Furthermore, it allows for an efficient filling of the arterial line 301 with rinse-back fluid.

The rinse-back fluid may for example be Saline or dialysis fluid, whereby the pumping device 324 may be arranged to provide saline or dialysis fluid to the extracorporeal fluid circuit 300 through being connected to a saline or dialysis fluid supply.

The pumping device 324 may be a dialysis fluid pump, the dialysis fluid pump being arranged to provide dialysis fluid to the extracorporeal fluid circuit 300. Accordingly, the rinse-back fluid may be dialysis fluid. Thereby, the method for filling may be performed by a conventional dialysis system with a dialysis fluid pump for providing dialysis fluid to the extracorporeal fluid circuit. Hence, a method for filling which may be performed by a conventional dialysis system without requiring additional components is achieved.

Further, this allows for rinsing and emptying of the fluid line connecting the dialysis fluid pump 324 and the extracorporeal fluid circuit 300 since the rinse-back fluid in the form of dialysis fluid may be sucked through the dialyzer 330. Thereby, the fluid line connecting the dialysis fluid pump 324 may be emptied by simply stopping the provision of rinse-back fluid while a net removal of rinse-back is performed in the dialyzer 330. Hence, said fluid line may be disposed in a manner similar to the disposing of the extracorporeal fluid circuit 300. The net removal may be performed by means of conveying the rinse-back fluid towards the drain of the dialysis machine via the dialyzer fluid circuit.

Now referring to FIG. 13-16, a dialysis system where rinse-back fluid is provided with the pump arrangement connected to the dialyzer is disclosed. The system is identical with the system depicted in FIG. 5-9 with the potential exception of the dialysis fluid pump which may not be required for the draining method to be performed.

The dialysis system comprises a dialysis machine 410 connected to an extracorporeal fluid circuit 400 and a dialyzer 430, wherein said extracorporeal fluid circuit 400 comprises an arterial line 401 connectable to a patient for drawing blood form the patient and a venous line 402 connectable to the patient for returning blood to the patient, said dialysis system being configured to perform the method for draining.

Connected to the extracorporeal fluid circuit is a peristaltic blood pump 422. The blood pump may be arranged to generate a flow both in the direction of the first port 491 i.e. the arterial line 401 as well as the second port 492 i.e. the venous line 402. Further, the peristaltic pump disallows flow or at least substantially prevent when the pump is not activated.

Figure 18:
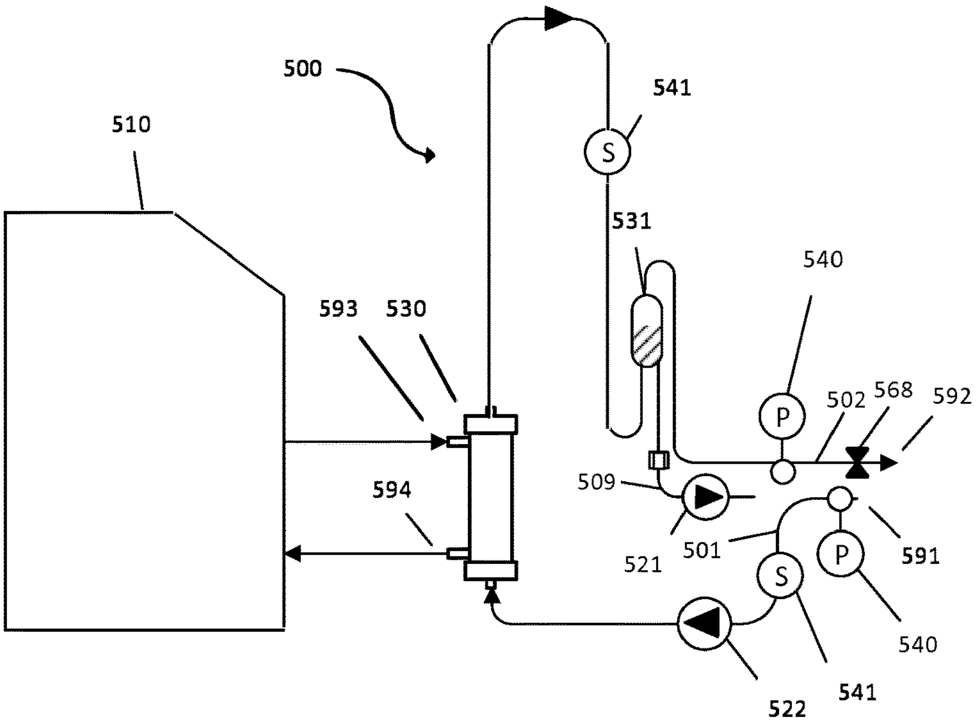
FIG. 18 schematically illustrates a dialysis system of one embodiment in a first state.

With reference to FIG. 18, a dialysis system immediately after treatment termination, i.e. right after any pumping of a patient's blood into the extracorporeal circuit connected to the dialysis machine has been terminated, i.e. when dialysis treatment has been interrupted or completed, is shown. The extracorporeal fluid circuit is thus filled with blood which may be drained in order to reduce the weight of the disposed material of the clinic. Thereby, the cost for handling the disposed material is severely reduced.

The patient is hence connected with the arterial line 401 and venous line 402 via the ports 491 and 492, i.e. the ports 491 and 492 are connected to the bloodstream of the patient. The dialysis machine 410 is connected to the dialyzer 430 via a first dialyzer line 493 and a second dialyzer line 494 forming a dialyzer fluid circuit. The dialyzer in turn is connected to the extracorporeal fluid circuit 400.

In order to provide the distribution of dialysis fluid to and from the dialyzer required for HDF-dialysis or HD-dialysis the dialyzer may be connected to a pump arrangement via the dialyzer fluid circuit 293, 294. Said pump arrangement is arranged to control the distribution of dialysis fluid into and from the extracorporeal fluid circuit via the dialyzer 230 and will be more closely described with reference to FIG. 20.

In this embodiment, the rinse-back fluid is introduced through controlling of the pump arrangement 63, 64. Accordingly, the rinse-back fluid may be dialysis fluid.

The fluid circuit 400 is connected to an air pump 421 via an inlet 409 connected to the fluid circuit 400, for example via a venous drip chamber 431 situated between the dialyzer 430 and the second port 492. Hence, the air pump 421 may be connected to the venous line 402.

Due to the risk for air embolism the extracorporeal fluid circuit 400 may be provided with an air sensor 450 configured to measure the air content in the fluid passing through the section of the fluid circuit provided with the air sensor 450. The air sensor 450 may for example be configured to generate a signal when air is detected which prompts an alarm to the operator or be received by a controller directly stopping the dialysis treatment.

Further, the venous drip chamber 431 may be provided with a level sensor 460 configured to monitor the level of fluid inside the chamber of said drip chamber 431.

As is well-known for the skilled person, the extracorporeal fluid circuit 200 may comprise a pressure sensor 440 for monitoring the pressure inside the extracorporeal fluid circuit.

Further, the extracorporeal fluid circuit may comprise a sample port 441 for extracting blood samples or dialysis fluid samples.

Figure 14:
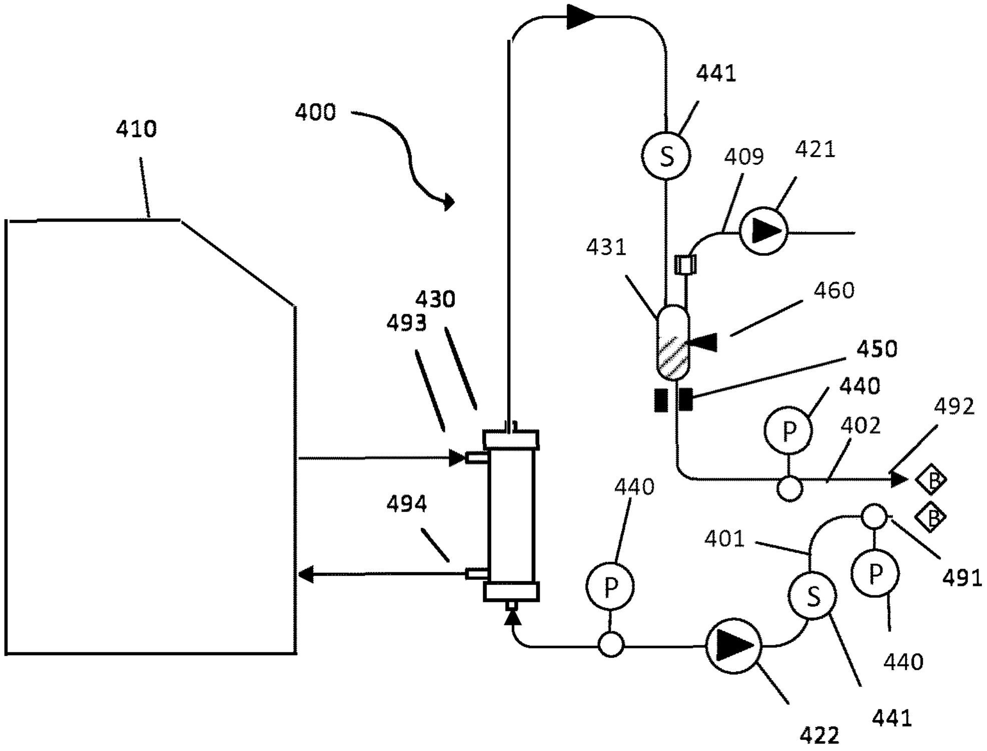
FIG. 14 schematically illustrates a dialysis system of one embodiment in a second state.

Referring to FIG. 14, the arterial line 401 is emptied of fluid immediately after treatment termination. Immediately after treatment termination said arterial line 401 may be substantially filled with blood. Thus, a pushback flow of blood in the direction of the arterial line 401 for emptying of said arterial line 401 may be generated. This pushback flow of blood may be generated by activation of the peristaltic blood pump 422.

Also, rinse-back fluid may be introduced during this state. Thus, rinse-back fluid is introduced into the extracorporeal fluid circuit 400 for filling the fluid circuit 400 prior to the draining of remaining fluid through the dialyzer 430. The rinse-back fluid may be dialysis fluid provided with the pump arrangement.

This may be performed through controlling of the pump arrangement so as to generate a flow of the rinse-back fluid in the direction of the venous line 402 through the dialyzer 430. Hence, the pump arrangement is controlled to generate the flow of rinse-back fluid through the dialyzer blood line of the dialyzer in the direction of the venous line 402. The flow of rinse-back fluid may hence be generated through the dialyzer blood line to the venous line.

Figure 15:
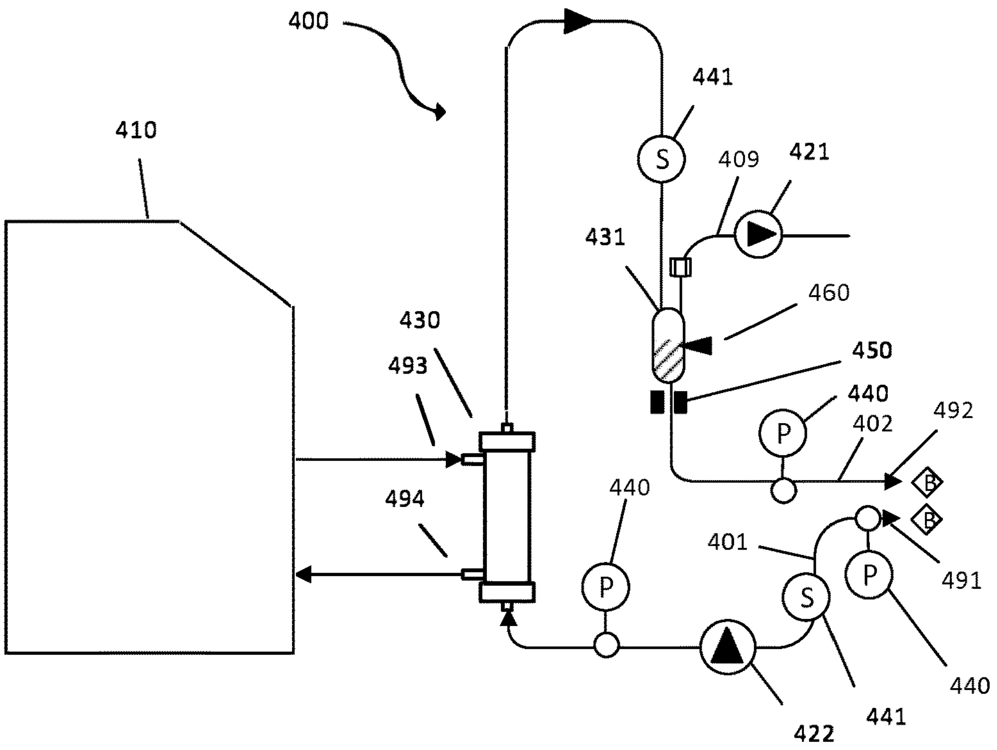
FIG. 15 schematically illustrates a dialysis system of one embodiment in a third state.

As shown in FIG. 15, said peristaltic blood pump 422 may be stopped so as to stop said generating of pushback flow when the arterial line 401 is substantially emptied of blood and instead filled with rinse-back fluid. Due to the design of a conventional peristaltic blood pump 422 this disallows, or at least substantially prevents, fluid communication with the arterial line 401. Instead it is allowed for the rinse-back fluid to flow in the direction of the dialyzer 430 and the venous line 402 and thereby fill the entire fluid circuit 400.

Figure 16:
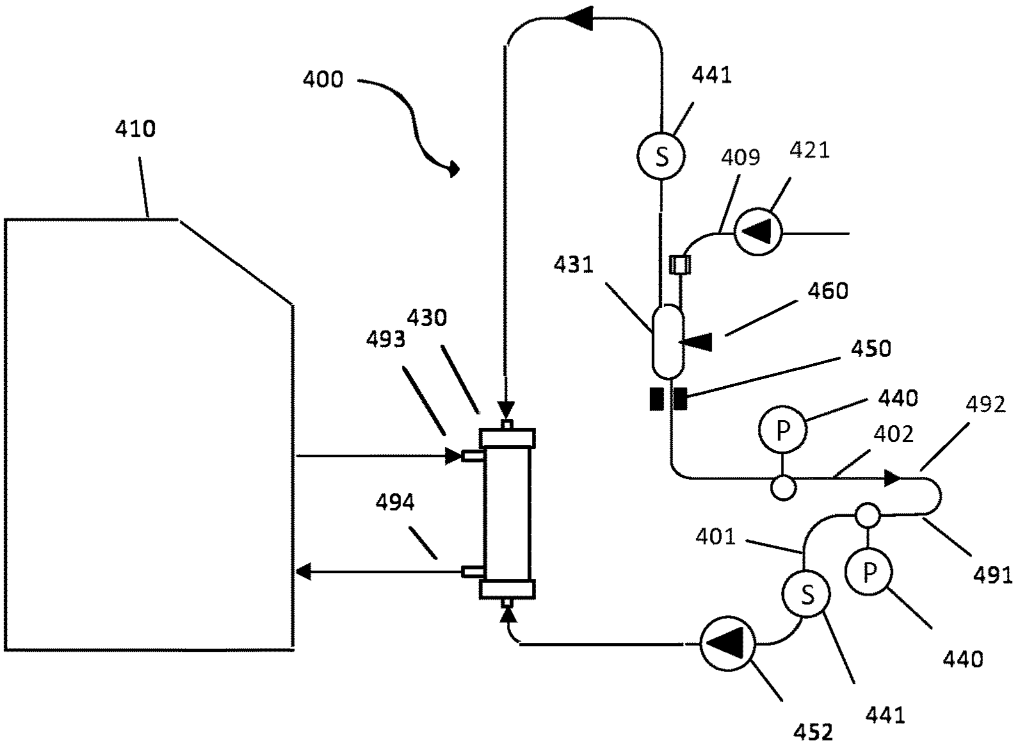
FIG. 16 schematically illustrates a dialysis system of one embodiment in a fourth state.
Figure 17:
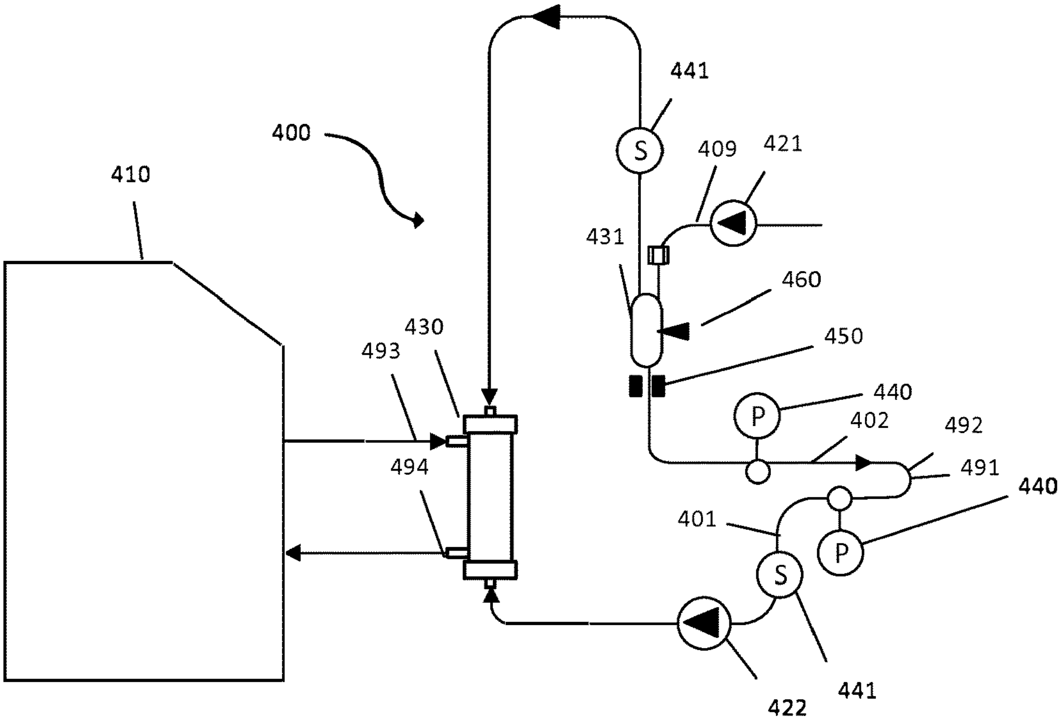
FIG. 17 schematically illustrates a dialysis system of one embodiment in a fifth state.

Referring to FIG. 16, the dialysis machine 410 is connected to the peristaltic blood pump 422, said blood pump being connected to the arterial line 401. The introduction of rinse-back fluid is thus achieved by activation of the peristaltic blood pump 422. This process may be performed until the rinse-back fluid substantially fills the extracorporeal fluid circuit 400. During this process, the pump arrangement may continuously provide dialysis fluid through the extracorporeal fluid circuit assisted by the peristaltic blood pump 422. Notably, the process may be stopped before the extracorporeal fluid circuit is filled with rinse-back fluid, i.e. when the extracorporeal fluid circuit is only partially filled with rinse-back fluid.

When the extracorporeal fluid circuit 400 is substantially filled with rinse-back fluid the first port 491 and the second port 492 may be connected. Thus, the extracorporeal fluid circuit becomes a closed-off circuit, allowing for initiation of the removal of the remaining fluid, which at this point may be a mixture of blood from the patient and rinse-back fluid. Notably, at this point there may still be a certain concentration of blood inside the fluid of the extracorporeal fluid circuit 400.

The extracorporeal fluid circuit is thereafter emptied of remaining fluid, which is schematically depicted in FIG. 16. The draining is initiated by applying a negative pressure on a dialyzer fluid circuit 493, 494 for distribution to and from the dialyzer 430 relative the extracorporeal fluid circuit 400, the dialysis machine 410 being connected to the dialyzer 430 via said dialyzer fluid circuit 493, 494. Said negative pressure forces the rinse-back fluid towards the dialyzer 430 from the venous line 402.

The negative pressure applied on the dialyzer fluid circuit relative the extracorporeal fluid circuit may in other words be considered as inducing a pressure difference between the extracorporeal fluid circuit 400 and the dialyzer fluid circuit 493, 494 to create suction, e.g. flow, of fluid into the dialyzer fluid circuit 493, 494 from the extracorporeal fluid circuit.

The suction and consequential flow of rinse-back flow may be achieved in a number of ways. For example, by selective clamping of the fluid circuit 400 with clamps and flow and suction control or control of the pressure through valve arrangements.

Alternatively, the negative pressure may be applied on the dialyzer fluid circuit relative the extracorporeal fluid circuit through introducing of a gas into the extracorporeal fluid circuit 400 via the inlet 409, whereby the remaining fluid is pushed towards the dialyzer 430 for draining through said dialyzer 430.

According to present embodiment, this may be performed with a pumping device 421, such as the air pump 421, connected to the extracorporeal fluid circuit 400 via the inlet 409.

To remove the remaining fluid, i.e. the rinse-back fluid filling the extracorporeal fluid circuit 400 together with potential residues from the treatment, a net removal of said remaining fluid has to be achieved. This may for example be achieved with the pump arrangement, which may be integrated into the dialysis machine, whereby the pump arrangement is controlled so as to achieve said net removal of remaining fluid from the dialyzer 430 and the extracorporeal fluid circuit 400 during the applying of negative pressure. Said pump arrangement will be further described with reference to FIG. 20.

As is conventional for dialyzers, or dialyzers with wet dialyzer membranes, the membrane of the dialyzer is impermeable for air unless subjected to a very high pressure over the membrane of said dialyzer. Such a high pressure is not achievable with the components commonly used in this field, accordingly there is no risk for the air to enter through the dialyzer 430 and enter the dialysis machine 410.

Furthermore, there is no possibility for the gas flowing through the extracorporeal fluid circuit 400 on each side of the dialyzer 430 to pass through the dialyzer 430 and thereby hinder the pushing of the remaining fluid towards the dialyzer 430 on the opposite side of said dialyzer 430.

If air is present in the dialyzer and there is no fluid (only a wet membrane), the passage through the dialyzer may be closed. That means that if there is any fluid elsewhere in the extracorporeal circuit that fluid cannot be removed. However, as long as there is fluid in the dialyzer that fluid can be removed. Detection of when the dialyzer is "closed" can be done by means of pressure sensors on either side of the dialyzer depending on which side the pressure gradient is created. For example, if the suction is achieved by means of the air pump 421 the pressure may be measured on the extracorporeal side.

Due to the peristaltic blood pump preferably not allowing for flow through it when not activated, said pump 422 may be activated so as to generate a flow of gas i.e. air in the direction of the dialyzer 430. If the blood pump is positioned between the dialyzer 430 and the arterial line 401, said peristaltic blood pump may accordingly generate a flow from the arterial line 401 of the now closed extracorporeal fluid circuit 400 into the dialyzer 430. Thus, the air pump 421 introduces the gas into the closed extracorporeal fluid circuit 400 towards the dialyzer 430 both via the venous line 402 and the arterial line 401, whereby the pumping of the peristaltic blood pump 422 enables the gas i.e. air passing through the arterial line towards the dialyzer 430. The flow of air thus pushes the fluid inside the circuit into the dialyzer 430 according to a similar flow pattern.

The speed of the filling of gas, i.e. the speed of emptying of the extracorporeal fluid circuit 400, may thus be controlled through controlling of the pump arrangement connected to the dialyzer fluid circuit 493, 494, the peristaltic blood pump 422 and the air pump 421.

Accordingly, when the emptying phase has been concluded the entire fluid circuit 400 is filled with gas. Thus the circuit is emptied of fluid due to the net removal of fluid taking place in the dialyzer 430, for example air, whereby the extracorporeal fluid circuit 400 may be disposed of without significant spillage or the circuit still containing fluid causing an increased waste disposal cost for the clinic.

The above described dialysis system shares all of the features with the system disclosed in FIG. 5-9 with the potential exception of the dialysis fluid pump. Further, the dialysis fluid system with reference to FIG. 13-17 is drained with the method disclosed with reference to FIG. 27.

Accordingly, the dialysis machine 410 is connected to the dialyzer 430 and said extracorporeal fluid circuit 400, said extracorporeal fluid circuit 400 comprising an arterial line 401 connectable to a patient, for drawing blood from the patient and a venous line 402 connectable to the patient for returning blood to the patient. The method comprising the step of:

after treatment termination from said extracorporeal fluid circuit 410 draining 2000 remaining fluid from said extracorporeal fluid circuit through the dialyzer 430.

The draining through the dialyzer allows for the dialysis machine, i.e. the drain and pump arrangement, to handle the remaining fluid in the extracorporeal fluid circuit.

Thereby the operator is not subjected to contaminated fluid in the process of emptying the extracorporeal fluid circuit, since said fluid circuit does not have to be emptied by hand into a sink or a bucket. Thus, a safer and more user-friendly draining process is achieved.

To avoid subjection to contaminated fluid for the operator the entire fluid circuit may also be sealed by clamps and disposed of. However this increases the weight of the disposed material considerably leading to higher costs for the clinic. Accordingly, the draining through the dialyzer thus enables draining without subjecting the operator to contaminated fluid in a cost-efficient manner since the fluid circuit can be substantially drained of fluid before disposal.

Treatment termination refers to a state where the dialysis treatment has been interrupted or completed. In other words, the method of draining is performed after said dialysis treatment has been interrupted or completed.

The method may comprise to after treatment termination from said extracorporeal fluid circuit 410 draining 2000 remaining fluid from said extracorporeal fluid circuit through the dialyzer fluid circuit 493, 494 of the dialyzer 430.

To drain the remaining fluid through the dialyzer a pressure difference between the dialyzer fluid circuit 493, 494 and the extracorporeal fluid circuit 400 may be applied. The dialyzer 430 is connected to the dialysis machine 410 via a dialyzer fluid circuit 493, 494 for distribution of dialysis fluid to and from the dialyzer 430, whereby the extracorporeal fluid circuit 410 is drained through the dialyzer 430 by applying a negative pressure on the dialyzer fluid circuit 493, 494 relative the extracorporeal fluid circuit. Thereby, the remaining fluid is forced towards and through the dialyzer in a stable and robust manner.

The negative pressure may be applied when the patient is disconnected. Accordingly, substantially no blood is drawn from the patient when the remaining fluid is drained through the dialyzer.

The negative pressure may be applied by introducing of gas into the extracorporeal fluid circuit 200. the introducing of the gas is performed by pumping of gas into the extracorporeal fluid circuit 400 via the inlet 409, wherein the remaining fluid is pushed towards the dialyzer 430 for draining through the dialysis machine.

The gas may be pumped into the extracorporeal fluid circuit 400 with a pumping device 421 connected to the extracorporeal fluid circuit 400 via the inlet 409. Hence, the method can be performed by an existing conventional dialysis system with an air pump without requiring additional components increasing the complexity of the dialysis system.

The method may further comprise introducing a rinse-back fluid 2010 into the extracorporeal fluid circuit 400 prior to the draining 2000 for filling the extracorporeal fluid circuit 400.

The introduction of the rinse-back fluid enables blood still in the extracorporeal fluid circuit to be returned. Thereby, the draining method may be performed without blood still in the circuit going to waste.

This may be performed by the dialysis fluid pump 424. The dialysis machine 410 is thus connected to a dialysis fluid pump 424 connected to the extracorporeal fluid circuit 400, wherein introducing of the rinse-back fluid into the extracorporeal fluid circuit 400 to fill said extracorporeal fluid circuit 400 is performed by activating a dialysis fluid pump 424 so as to generate a flow of the rinse-back fluid in the direction of the venous line 402 through the dialyzer 430. Accordingly, the rinse-back fluid is led via the dialyzer blood line of the dialyzer towards the venous line. The flow of rinse-back fluid may hence be generated through the dialyzer blood line to the venous line.

Thereby, a method for draining with the aforementioned advantages which may be executed by a dialysis system provided with a dialysis fluid pump is achieved. Furthermore, a method for draining which enables draining of the fluid line connecting the dialysis fluid pump 424 and the extracorporeal fluid circuit 400 is achieved, which may increase the efficiency of the draining.

The dialyzer 430 is connected to the pump arrangement 63, 64 for distribution of dialysis fluid to and from the dialyzer 430. The method may thus further comprise controlling 2030 the pump arrangement 63, 64 to achieve a net removal of remaining fluid from the dialyzer 430 and the extracorporeal fluid circuit 400 during the applying of negative pressure. Said net removal consequently causes the extracorporeal fluid circuit to gradually empty so as to enable the disposal of said extracorporeal fluid circuit 400 at a later stage.

To generate a flow of the rinse-back fluid in the direction of the dialyzer 430, the method may further comprise activating 2005 the peristaltic blood pump 422 to generate a flow of the rinse-back fluid in the direction of the dialyzer 430 after the rinse-back fluid has been introduced 2010.

Before removal of the remaining fluid through the dialyzer 430, the extracorporeal fluid circuit 400 is closed. Accordingly, the method may further comprise connecting 2015 the first port 491 to the second port 492 prior to introducing the gas into the extracorporeal fluid circuit 400.

The closing of the fluid circuit effectively reduces the risk for spillage of fluid from the fluid circuit during draining, whereby the risk for infection due to contamination is reduced greatly. Further, the mitigated risk for spillage allows for a more user-friendly draining process.

After draining 2000 the remaining fluid through the dialyzer 430, the remaining fluid may be led out through a drain 68 (which will be further described with reference to FIG. 20). Accordingly, the method may further comprise conveying 2060 the remaining fluid removed from the extracorporeal fluid circuit 400 to a drain 68 of the dialysis machine 410. The drain 68 may be connected to the dialyzer fluid circuit 493, 494.

The method may further comprise conveying 2060 the remaining fluid removed from the extracorporeal fluid circuit to the drain 68 of the dialysis machine 410 via the dialyzer fluid circuit 493, 494.

This may be performed immediately after the controlling 2030 of the pump arrangement 63, 64 to achieve the net removal of remaining fluid from the dialyzer 430.

As partly previously described, the method may further comprise generating 2003 the pushback flow of blood in the direction of the arterial line 401 for emptying of the arterial line 401 of blood prior to the generating the flow of the rinse-back fluid in the direction of the dialyzer 430. The arterial line is thus emptied of blood leading to less blood going to waste in the draining process. Furthermore, it allows for an efficient filling of the arterial line 401 with rinse-back fluid.

Hence, the method may further comprise activating the peristaltic blood pump 422 so as to generate the pushback flow and stopping 2004 said peristaltic blood pump 422 so as to stop said generating of pushback flow when the arterial line 401 is substantially emptied of blood. The method may thus be performed by a conventional dialysis system without requiring additional components.

Additionally, the aforementioned method may further comprise introducing rinse-back fluid into the extracorporeal fluid circuit 400 through controlling of the pump arrangement 63, 64. Thereby, the method may be performed by a system without a dialysis fluid pump directly connected to the extracorporeal fluid circuit, i.e. not via the dialyzer.

Figure 19:
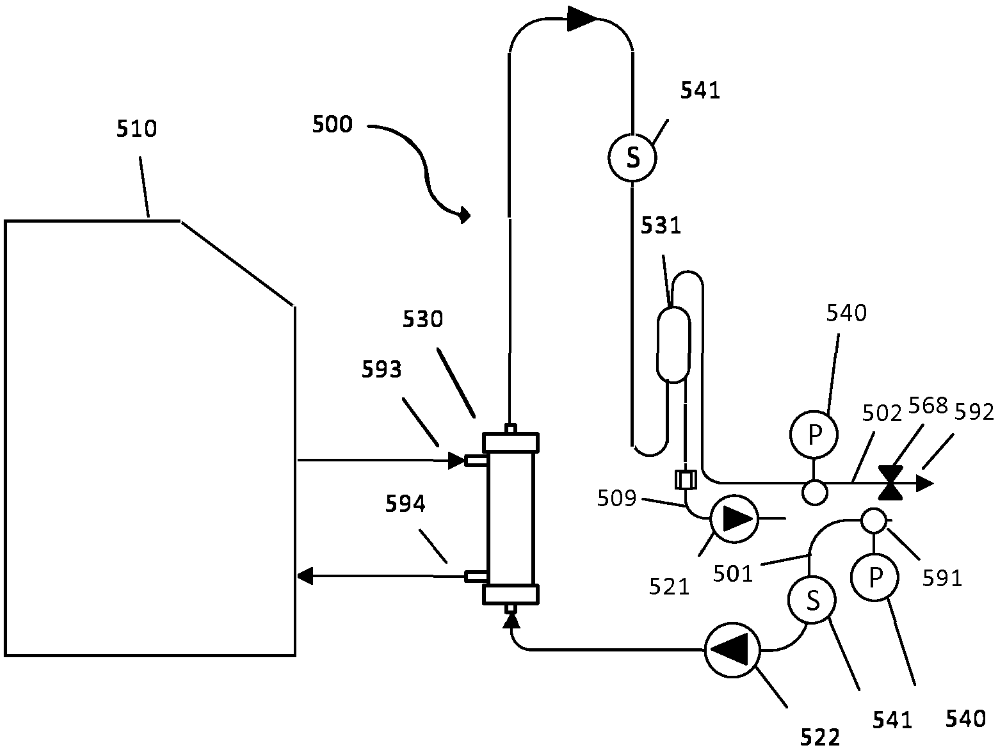
FIG. 19 schematically illustrates a dialysis system of one embodiment in a second state.

FIG. 18-19 discloses a dialysis system which utilizes an open end draining identical to the system disclosed in FIG. 11-12, however similar to the dialysis system depicted in FIG. 13-17 the rinse-back fluid is provided by controlling of the pump arrangement.

With reference to FIG. 18, the dialysis system comprises a dialysis machine 510 connected to an extracorporeal fluid circuit 500 and a dialyzer 530, wherein said extracorporeal fluid circuit 500 comprises an arterial line 501 connectable to a patient for drawing blood form the patient and a venous line 502 connectable to the patient for returning blood to the patient, said dialysis machine of the dialysis system being configured to perform the method for draining.

Connected to the extracorporeal fluid circuit is a peristaltic blood pump 522. The blood pump may be arranged to generate a flow both in the direction of the first port 591 i.e. the arterial line 501 as well as the second port 592 i.e. the venous line 502. Further, the peristaltic pump disallows flow or at least substantially prevent flow when the pump is not activated.

The dialysis machine 510 is connected to the dialyzer 530 via a first dialyzer line 593 and a second dialyzer line 594 forming a dialyzer fluid circuit. The dialyzer in turn is connected to the extracorporeal fluid circuit 500.

In order to provide the distribution of dialysis fluid to and from the dialyzer required for HDF-dialysis the dialyzer may be connected to a pump arrangement, which is more closely described with reference to FIG. 28.

In this embodiment, the rinse-back fluid is introduced through controlling of the pump arrangement 63, 64. Accordingly, the rinse-back fluid may be dialysis fluid.

The fluid circuit 500 is connected to an air pump 521 via an inlet 509 connected to the fluid circuit 500, for example via a venous drip chamber 531 situated between the dialyzer 530 and the second port 592. Hence, the air pump 521 may be connected to the venous line 502.

As is well-known for the skilled person, the extracorporeal fluid circuit 500 may comprise a pressure sensor 540 for monitoring the pressure inside the extracorporeal fluid circuit.

Further, the extracorporeal fluid circuit may comprise a sample port 541 for extracting blood samples or dialysis fluid samples.

Referring to FIG. 19, the dialysis system is depicted in a state where the patient is disconnected and the first port 591 and the second port 592, whereby said ports are free ends of the extracorporeal fluid circuit. At this point the method for draining differs from the previously described with reference to FIG. 14-17 in that the ports are not connected in order to empty the extracorporeal fluid circuit.

The draining is initiated by applying a negative pressure on a dialyzer fluid circuit 593, 594 for distribution to and from the dialyzer 530 relative the extracorporeal fluid circuit 500, the dialysis machine 510 being connected to the dialyzer 530 via said dialyzer fluid circuit 593, 594. Said negative pressure forces the rinse-back fluid towards the dialyzer 530 from the venous line 502.

The negative pressure applied on the dialyzer fluid circuit relative the extracorporeal fluid circuit may in other words be considered as inducing a pressure difference between the extracorporeal fluid circuit 500 and the dialyzer fluid circuit 593, 594 to create suction, e.g. flow, of fluid into the dialyzer fluid circuit 593, 594 from the extracorporeal fluid circuit.

The suction and consequential flow of rinse-back flow may be achieved in a number of ways. For example, by selective clamping of the fluid circuit 500 with clamps and suction and flow control or control of the pressure through valve arrangements.

Alternatively, the negative pressure applied on the dialyzer fluid circuit relative the extracorporeal fluid circuit may be applied through introducing of a gas into the extracorporeal fluid circuit 500 via an inlet, whereby the remaining fluid is pushed towards the dialyzer 530 for draining through said dialyzer 530.

According to this embodiment, the inlet for the gas may be any or both of the free ends of the fluid circuit 500 i.e. the first port 591 or the second port 592.

To allow for the remaining fluid to be drained through the dialyzer 530 and flow towards said dialyzer, the venous drip chamber 531 is turned around, i.e. turned upside down. for emptying of said venous drip chamber of remaining fluid and thereby introduce gas into the extracorporeal fluid circuit 500.

In order to introduce the gas into the extracorporeal fluid circuit 500 the peristaltic blood pump 522 may be activated. By activating said blood pump 522 to create a flow the direction of the dialyzer 530 gas is sucked through the first port 591. The gas may comprise air from the surrounding room.

As is conventional for dialyzers, or dialyzers with wet dialyzer membranes, the membrane of the dialyzer is impermeable for air unless subjected to a very high pressure over the membrane of said dialyzer. Such a high pressure is not achievable with the components commonly used in this field, accordingly there is no risk for the air to enter through the dialyzer 530 and enter the dialysis machine 510.

Furthermore, there is no possibility for the gas flowing through the extracorporeal fluid circuit 500 on each side of the dialyzer 530 to pass through the dialyzer 530 and thereby hinder the pushing of the remaining fluid towards the dialyzer 530 on the opposite side of said dialyzer 530.

If air is present in the dialyzer and there is no fluid (only a wet membrane), the passage through the dialyzer may be closed. That means that if there is any fluid elsewhere in the extracorporeal circuit that fluid cannot be removed. However, as long as there is fluid in the dialyzer that fluid can be removed. Detection of when the dialyzer is "closed" can be done by means of pressure sensors on either side of the dialyzer depending on which side the pressure gradient is created. For example, if the suction is achieved by means of the air pump 521 the pressure may be measured on the extracorporeal side.

The risk for spillage of the remaining fluid may be greatly reduced by locking of a clamp 558 to the second port 592 after the rinse-back fluid has been introduced into extracorporeal fluid circuit 500. However, said clamp 558 has to be released prior to sucking in the gas via the first port 591.

After the turning around of the venous drip chamber 531, all of the remaining fluid in the venous line 502 is forced to flow towards the dialyzer 530 and exit through a drain 68 (not shown) of the dialysis machine 510. This in conjunction with the pumping of air through the arterial line 501 fills the entire fluid circuit with air, thereby draining all of the remaining fluid through the dialyzer 530, this state is shown in FIG. 12 where the venous drip chamber 531 is substantially filled with air. Thereafter, the now empty extracorporeal fluid circuit may be disposed of.

The above described dialysis system shares all of the features with the system disclosed in FIG. 11-12 with the potential exception of the dialysis fluid pump. Further, the dialysis fluid system with reference to FIG. 18-19 is drained with the method disclosed with reference to FIG. 28.

FIG. 28 shows a schematic view of a method of draining the extracorporeal fluid circuit 500 utilizing a dialysis machine 510. The dialysis machine 510 is connected to the dialyzer 530 and said extracorporeal fluid circuit 500, said extracorporeal fluid circuit 500 comprising an arterial line 501 connectable to a patient, for drawing blood from the patient and a venous line 502 connectable to the patient for returning blood to the patient. The method comprising the step of:

after treatment termination from said extracorporeal fluid circuit 510 draining 3000 remaining fluid from said extracorporeal fluid circuit through the dialyzer 530.

This enables for all of the fluid to be drained to be pushed through the dialyzer 530 thus filtering said fluid, resulting in a significantly reduced risk for contamination or cross-contamination.

The draining through the dialyzer allows for the dialysis machine, i.e. the drain and pump arrangement, to handle the remaining fluid in the extracorporeal fluid circuit.

Thereby the operator does not have to be subjected to contaminated fluid in the process of emptying the extracorporeal fluid circuit, since said fluid circuit does not have to be emptied by hand into a sink or a bucket. Thus, a safer and more user-friendly draining process is achieved.

To avoid subjection to contaminated fluid for the operator the entire fluid circuit may also be sealed by clamps and disposed of. However this increases the weight of the disposed material considerably leading to higher costs for the clinic. Accordingly, the draining through the dialyzer thus enables draining without subjecting the operator to contaminated fluid in a cost-efficient manner since the fluid circuit can be substantially drained of fluid before disposal.

Treatment termination refers to a state where the dialysis treatment has been interrupted or completed. In other words, the method of draining is performed after said dialysis treatment has been interrupted or completed.

The method may comprise to after treatment termination from said extracorporeal fluid circuit 510 draining 3000 remaining fluid from said extracorporeal fluid circuit through the dialyzer fluid circuit 593, 594 of the dialyzer 530.

To drain the remaining fluid through the dialyzer 530 a pressure difference between the dialyzer fluid circuit 593, 594 and the extracorporeal fluid circuit 500 may be applied. The dialyzer 530 is connected to the dialysis machine 510 via a dialyzer fluid circuit 593, 594 for distribution of dialysis fluid to and from the dialyzer 530, whereby the extracorporeal fluid circuit 510 is drained through the dialyzer 530 by applying a negative pressure on the dialyzer fluid circuit 593, 594 relative the extracorporeal fluid circuit. Thereby, the remaining fluid is forced towards and through the dialyzer in a stable and robust manner.

The negative pressure may be applied when the patient is disconnected. Accordingly, substantially no blood is drawn from the patient when the remaining fluid is drained through the dialyzer.

The negative pressure may be applied by introducing of gas into the extracorporeal fluid circuit 500. The introducing of the gas is performed by pumping of gas into the extracorporeal fluid circuit 500 via the inlet 509, wherein the remaining fluid is pushed towards the dialyzer 530 for draining through the dialysis machine.

The gas may be pumped into the extracorporeal fluid circuit 500 with a pumping device 521 connected to the extracorporeal fluid circuit 500 via the inlet 509 or the first port forming the inlet 591.

The method may further comprise introducing a rinse-back fluid 3010 into the extracorporeal fluid circuit 500 prior to the draining 3000 for filling the extracorporeal fluid circuit 500. Hence, the method can be performed by an existing conventional dialysis system with an air pump without requiring additional components increasing the complexity of the dialysis system.

The introduction of the rinse-back fluid enables blood still in the extracorporeal fluid circuit to be returned. Thereby, the draining method may be performed without blood still in the circuit going to waste by not being returned to the patient.

The dialyzer 530 is connected to the pump arrangement 63, 64 for distribution of dialysis fluid to and from the dialyzer 530. The method may thus further comprise controlling 3030 the pump arrangement 63, 64 to achieve a net removal of remaining fluid from the dialyzer 530 and the extracorporeal fluid circuit 300 during the applying of negative pressure. Said net removal consequently causes the extracorporeal fluid circuit to gradually empty so as to enable the disposal of said extracorporeal fluid circuit 500 at a later stage.

To generate a flow of the rinse-back fluid in the direction the dialyzer 530, the method may further comprise activating 3005 the peristaltic blood pump 522 to generate a flow of the rinse-back fluid in the direction of the dialyzer 530 after the rinse-back fluid has been introduced 3010. The dialysis machine 510 being connected to the peristaltic blood pump 522.

After draining 3000 the remaining fluid through the dialyzer 530, the remaining fluid may be led out through a drain 68 (which will be further described with reference to FIG. 20). Accordingly, the method may further comprise conveying 3060 the remaining fluid removed from the extracorporeal fluid circuit 500 to a drain 68 of the dialysis machine 510. The drain 68 may be connected to the dialyzer fluid circuit 593, 594.

The method may further comprise conveying 2060 the remaining fluid removed from the extracorporeal fluid circuit to the drain 68 of the dialysis machine 510 via the dialyzer fluid circuit 593, 594.

This may be performed immediately after the controlling 3030 of the pump arrangement 63, 64 to achieve the net removal of remaining fluid from the dialyzer 530.

To empty the extracorporeal fluid circuit 500, the method may further comprise turning 3013 the venous drip chamber 531531 connected to the venous line 502 for emptying said venous drip chamber 531531 of remaining fluid so as to introduce gas into the extracorporeal fluid circuit 500.

The gas may also be introduced into the extracorporeal fluid circuit 500 by activation of the peristaltic blood pump 522 to suck gas into the extracorporeal fluid circuit 500 via the first port 591.

Thereby both the venous line 502 and the arterial line 501 may be filled with gas effectively forcing all of the remaining fluid into the dialyzer 530. In comparison to the connecting of the ports required in the previously described embodiments for filling the extracorporeal fluid circuit with gas this does not pose any demanding requirements on the design of the ports. With some ports additional components such as adapters may be required in order to achieve the connection in a proper manner. Instead, the gas may be introduced directly into the fluid circuit without the additional step of connecting the ports, whereby a more user-friendly draining method is achieved. Furthermore it may be performed using almost any type of conventional dialysis system since it does not require specific ports suitable for connecting.

The risk for spillage may be reduced by the method further comprising locking 3011 a clamp 368 to the second port 592 after introducing 3010 the extracorporeal fluid circuit 500 with said rinse-back fluid and releasing 3012 said clamp 568 prior to sucking the gas into the fluid circuit via the first port 591.

The method may further comprise generating 3003 the pushback flow of blood in the direction of the arterial line 501 for emptying of the arterial line 501 of blood prior to the generating the flow of the rinse-back fluid in the direction of the dialyzer 530. The arterial line is thus emptied of blood leading to less blood going to waste in the draining process. Furthermore, it allows for an efficient filling of the arterial line 501 with rinse-back fluid.

Hence, the method may further comprise activating the peristaltic blood pump 522 so as to generate the pushback flow and stopping 3004 said peristaltic blood pump 522 so as to stop said generating of pushback flow when the arterial line 501 is substantially emptied of blood.

Additionally, the aforementioned method may further comprise introducing rinse-back fluid into the extracorporeal fluid circuit 500 through controlling of the pump arrangement 63, 64. Thereby, the method may be performed by a system without a dialysis fluid pump directly connected to the extracorporeal fluid circuit, i.e. not via the dialyzer.

Figure 20:
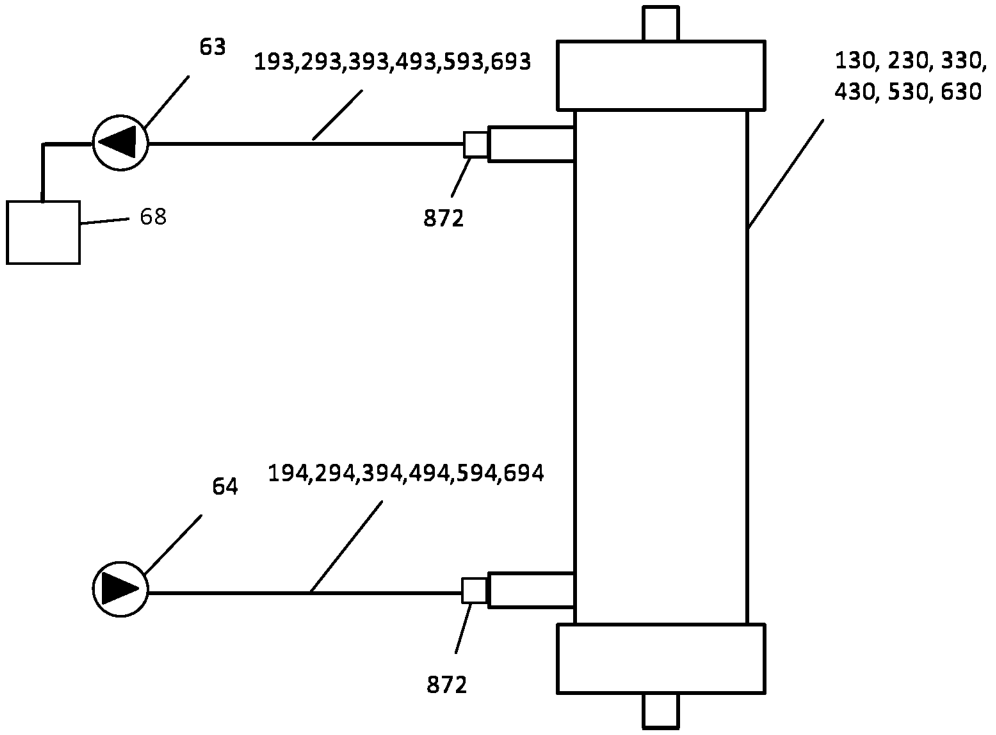
FIG. 20 schematically illustrates a dialyzer of a dialysis system of one embodiment.

FIG. 20 schematically depicts the pump arrangement 63, 64. The pump arrangement may be disposed inside the dialysis machine of the systems disclosed with reference to FIG. 1-19. The pump arrangement 63, 64 is arranged to distribute dialysis fluid to and from the dialyzer and may accordingly be connected to a dialysis fluid supply of the dialysis machine.

To enable the draining of the remaining fluid of the extracorporeal fluid circuit the pump arrangement 63, 64 are connected to the drain 68, i.e. in fluid communication with the drain 68. Thereby, the remaining fluid can be disposed of in a simple manner which is both cheaper for the clinic and allows for a cleaner process which does not require any manual draining or at least minimizes the manual input required in order to perform the draining.

The pump arrangement comprises a first dialyzer pump 63 and a second dialyzer pump 64 both being connected to the dialyzer fluid circuit referenced in FIG. 1-19. Accordingly, the distribution of dialysis fluid to and from the extracorporeal fluid circuit may be controlled by controlling of the first dialyzer pump 63 and the second dialyzer pump 64. The induced pressure difference between the first 63 and second 64 dialyzer pumps may either force the fluid inside the dialyzer to flow from the arterial line to the venous line without entering the dialyzer fluid circuit as well as remove and add fluid from the dialyzer via the dialyzer fluid circuit 193, 293, 393, 493, 593, 693, 194, 294, 394, 494, 594, 694.

Thus, the dialyzer fluid passing through the dialyzer may be forced to pass right through the dialyzer simply by controlling the pumps 63, 64 so as to create a flow towards the dialyzer disallowing or at least substantially preventing the fluid passing through the dialyzer to flow into the dialyzer fluid circuit.

The first dialyzer pump 63 may be directly connected to the drain 68, accordingly the drain 68 may be connected to an outlet of the first dialyzer pump 63. The second dialyzer pump may thus be directly connected to the supply of dialysis fluid, accordingly an inlet of the second dialyzer pump 64 may be directly connected to the supply of dialysis fluid. In other words, the second dialyzer pump 64 is arranged to provide a flow of dialysis fluid into the dialyzer.

The controlling of the pump arrangement 63, 64 to achieve a net removal of the remaining fluid from the dialyzer and the extracorporeal fluid circuit during the applying of negative pressure may thus be achieved by controlling of the first dialyzer pump 63 and the second dialyzer pump 64. The net removal may be provided by controlling of the first dialyzer pump 63 to pump the fluid in the dialyzer towards the drain at a faster speed than the second dialyzer pump 64 provides dialysis fluid into said dialyzer.

Said pump arrangement 63, 64 may be manually controlled via an operator, or automatically controlled by a controller configured to communicate with said pump arrangement. Accordingly, the controller may be operatively connected to said pump arrangement.

To monitor the pressure in the dialyzer fluid circuit said circuit may be provided with one or a plurality of pressure sensors 872, said pressure sensors being configured to monitor the pressure in said dialyzer fluid circuit. Thus, the pump arrangement 63, 64 may be configured to be controlled in response to the sensor signals from the at least one pressure sensor 872. Thereby, the pumping may be terminated if the pressure is very high. Furthermore, the pressure difference generated from the dialyzer pumps may be maintained and ensured by said pumps being controlled in response to the sensor signals generated by the pressure sensors.

The dialyzer fluid circuit may comprise a first pressure sensor in fluid communication with the first dialyzer pump 63 and a second pressure sensor in fluid communication with the second dialyzer pump 64. The dialyzer fluid circuit may accordingly comprise a first dialyzer fluid line 193, 293, 393, 493, 593, 693 for connecting the drain 68, the first dialyzer pump 63 and the dialyzer and a second dialyzer fluid line 194, 294, 394, 494, 594, 694 for connecting the supply of dialysis fluid sensor and the dialyzer.

As described with reference to FIG. 1-20, the dialyzer 130, 230, 330, 430, 530, 630 comprises the dialyzer blood line and the membrane for filtering the fluid, e.g. liquid, passing through the dialyzer blood line. The dialyzer blood line connects the arterial line and the venous line. The membrane may be connected to the dialyzer blood line, e.g. said membrane may extend through said dialyzer blood line, whereby said dialyzer blood line may be configured to provide fluid passage (e.g. liquid passage), through the membrane of the dialyzer between said arterial line and venous line.

The dialyzer fluid circuit 193, 194, 293, 294, 393, 394, 492, 493, 593, 594 is connected to the dialyzer blood line after and before the membrane, e.g. upstream and downstream of the membrane of the dialyzer. Accordingly, the first dialyzer fluid line 193, 293, 393, 493, 593, 693 is connected to the dialyzer blood line downstream of the membrane, whereby the second dialyzer fluid line 194, 294, 394, 494, 594, 694 is connected to the dialyzer blood line upstream of the membrane. Downstream and upstream are herein defined by the direction from the arterial line towards the venous line, e.g. the direction the blood flows during the dialysis treatment.

Figure 21:
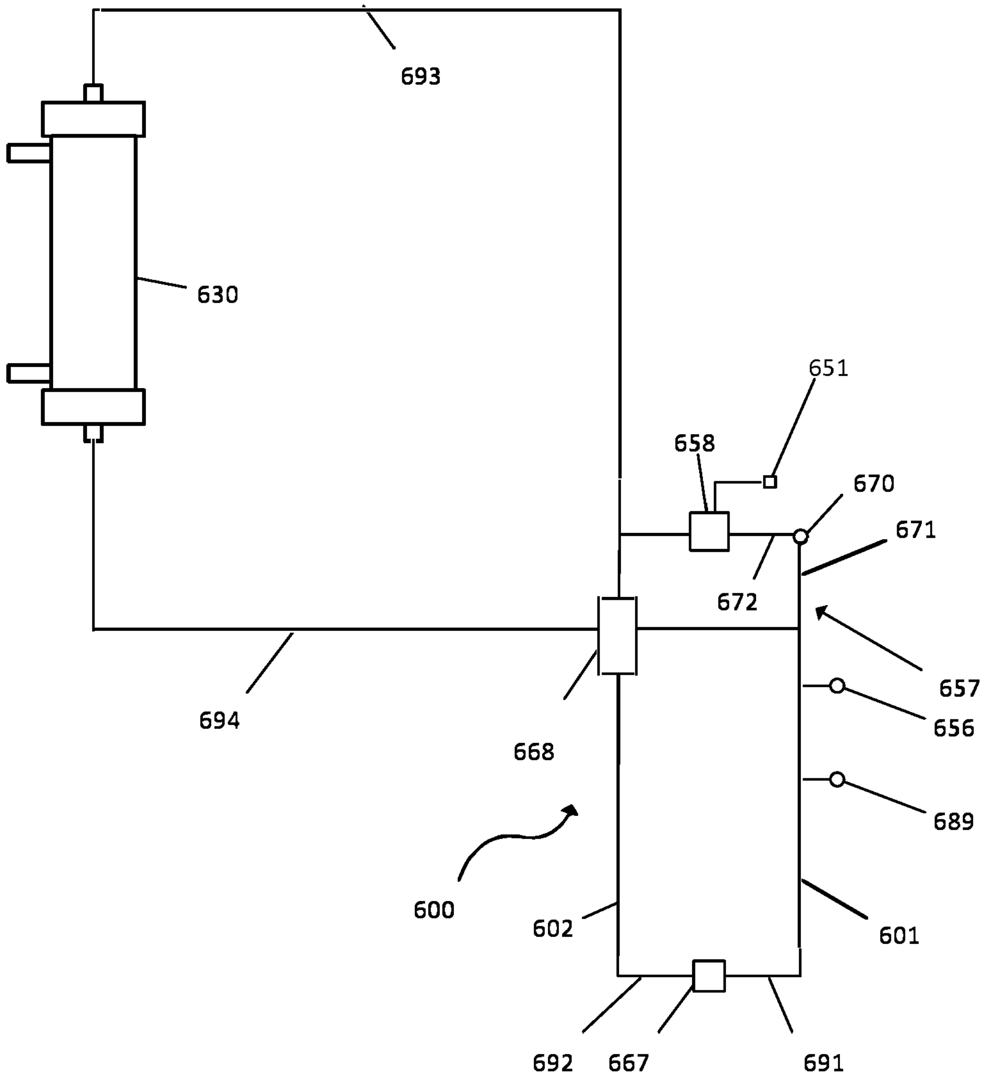
FIG. 21 schematically illustrates an extracorporeal circuit of a dialysis system of one embodiment.

FIG. 21 depicts an extracorporeal fluid circuit 600 for connecting to a dialysis machine according to the embodiments disclosed in FIG. 1-19 connected to a dialyzer 630 (as indicated by the arrows in said figure). Said fluid circuit 600 may be included in any one of the previously described dialysis systems as referenced in FIG. 1-19, furthermore it may be drained according to the aforementioned methods of draining 1000, 2000, 3000.

Accordingly, the dialysis machine 610 (not shown in FIG. 21) is connected to the dialyzer 630 and the extracorporeal fluid circuit 600, said extracorporeal fluid circuit 600 comprising an arterial line 601 connectable to a patient, for drawing blood from the patient and a venous line 602 connectable to the patient for returning blood to the patient.

The arterial line 601 extends into the first port 691 while the venous line 602 extends into the second port 692. Further, the extracorporeal fluid circuit 600 may be provided with a pre-infusion clamp 658 arranged to control the fluid flow from and to the dialyzer 630.

As seen in FIG. 21 the extracorporeal fluid circuit may comprise a arterial dialyzer line 697 and a venous dialyzer line 696, the arterial dialyzer line being connected with the inlet port of the dialyzer 630 as well as the arterial line 691 and the venous dialyzer line being connected with the outlet port of the dialyzer 630 as well as the venous line 692. The connection between said arterial lines respective said venous lines may be achieved by an adapter 668 arranged to connect said lines.

The extracorporeal fluid circuit may further comprise an anticoagulation inlet 656 arranged to receive an anticoagulation syringe. Said syringe may for example contain Heparin or a similar anticoagulant.

The extracorporeal fluid circuit 600 may additionally comprise a pre/post-dialyzer connection 657 being connected to the venous dialyzer line 696 and the arterial line 691. Said pre/post-dialyzer connection 657 may further be arranged to be connected to a source of rinse-back fluid. Accordingly, said connection 657 may comprise a connection inlet 670 arranged to be connected to a rinse-back fluid source and a first connection outlet 671 connected to the arterial line 691 and a second connection outlet 672 connected to the dialyzer venous line 693. Thus, the operator may select between introducing the rinse-back fluid pre- or post-dialyzer in the fluid circuit by applying said pre-infusion clamp 658 to said pre/post-dialyzer connection 657. By applying said clamp 658 to both of said outlets the flow of rinse-back fluid from the rinse-back fluid source is prevented or at least substantially prevented.

Correspondingly, by applying the pre-infusion clamp to first inlet 671 the rinse-back fluid is led into the fluid circuit post-dialyzer and by applying the pre-infusion clamp to the second inlet 672 the rinse-back is led into the fluid circuit pre-dialyzer.

The extracorporeal fluid circuit 600 may further comprise a service line 651 arranged to receive any of the following: the first port 691, the second port 692 and an port adapter 667 for connecting said first and second port.

In the process of draining said fluid circuit 600, the arterial line 601 may be attached to the service line 651 after treatment termination. Hence, the first port and the second port are connected in accordance with the method for draining through the dialyzer depicted in FIG. 28.

To enable the rinse-back to enter the fluid circuit, the method of draining may further comprise opening the pre-infusion clamp prior to the draining 1000, 2000, 3000 through the dialyzer after the rinse-back fluid has been introduced into the extracorporeal circuit 600.

The flow of rinse-back fluid may be controlled by the clamp 658 or a pump so as to be approximately 100 ml/min.

The dialysis machine 610 is connected to a peristaltic blood pump connected to the arterial line 601. In one embodiment, a flow of rinse-back fluid may be generated by activating said blood pump to generate a flow of the rinse-back fluid in the direction of the dialyzer (in accordance with the previously described method steps 1005, 2005, 3005) through the arterial line 691. Said blood pump may be pumping at approximately 100 ml/min. Notably, this requires the blood pump to pump in a direction opposite to the direction while said blood pump operates with during treatment.

After the arterial line 691 has been emptied after being filled with rinse-back fluid it is disconnected from the service line 651. Instead, the venous line 692 is connected with said service line 651, whereby a flow of rinse-back fluid is generated by activating said blood pump to generate a flow of the rinse-back fluid in the direction of the dialyzer (in accordance with the previously described method steps 1005, 2005, 3005) through the venous line 691.

The arterial line 601 may also be connected with the rinse-back container via an arterial infusion line 689, the arterial infusion line forming an inlet to the arterial line 601.

Thereafter, the rinse-back fluid may be introduced into the extracorporeal circuit 600 through said infusion line 689, whereby the introduction may be achieved by the operator directly or by elevating of the rinse-back container so as to allow for gravity to force the rinse-back fluid from said container to the extracorporeal fluid circuit 600.

To allow for the draining through the dialyzer, the blood pump may be activated so as to generate a rinse-back fluid flow in the direction of the dialyzer. The blood pump may be operated at 100 ml/min. Notably, this requires the blood pump to pump in the same direction in which it operates with during dialysis treatment of a patient.

After the rinse-back fluid has filled the entire extracorporeal fluid circuit 600, the dialyzer 660 and venous line 602 may be drained through usage of gravity, i.e. by the operator simply lifting the extracorporeal fluid circuit 600 or more specifically the venous line 602 so as to allow for all of the rinse-back fluid to enter through the dialyzer 630 and to the drain of the dialysis machine. As described with reference to FIG. 20, the fluid may be conveyed to the drain via the dialyzer fluid circuit.

The draining of the extracorporeal fluid circuit may also be performed identical to the embodiment described with reference to FIG. 1-4. Hence, the arterial line 601 may be directly connected to a rinse-back container through the first port 691 after said first port has been disconnected from the patient.

Figure 22:
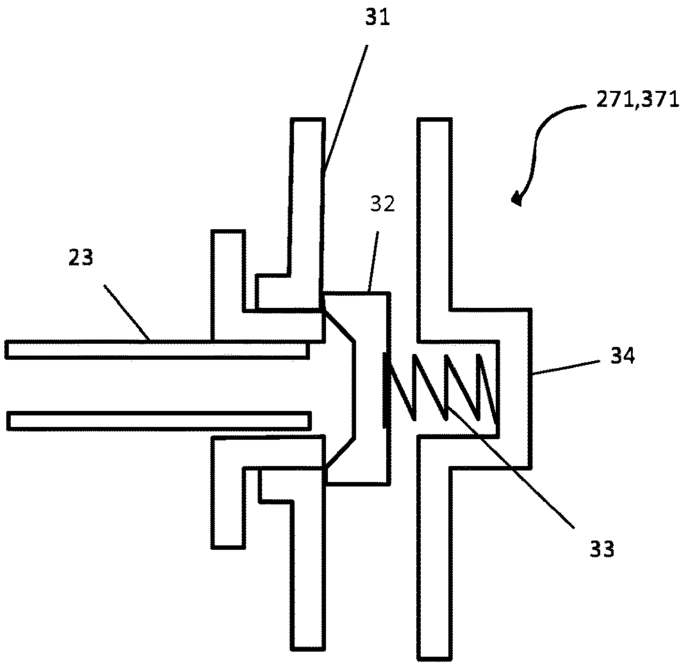
FIG. 22 schematically illustrates a check valve of a dialysis system of one embodiment.

FIG. 22 discloses a cross-section view of the check valve 271, 371 previously described with reference to for example FIG. 10. The check valve 271, 371 may comprise of a casing 31 formed by a section of the fluid line connectable to the extracorporeal fluid circuits disclosed in any one of the aforementioned embodiments. The check valve 271, 371 further comprises a first connection 23 arranged to be connected to the dialysis fluid pump. The check valve 271, 371 further comprises a valve member 32 arranged to abut to a wall of the casing 31 in a fluid tight manner so as to seal said first connection 23. To provide the check valve functionality, i.e. enabling the provision of fluid from the dialysis fluid pump via the first connection 23 while fluid flow is prevented in the other direction, the valve member 32 is connected to a wall of the casing 31 via a spring 33. The spring 33 may be connected to a cavity 34 of the casing 31 so as to not interfere with the flow through the casing.

The check valve 271, 371 greatly reduces the risk for contamination of the dialysis fluid pump since potential backwards flow of possibly contaminated fluid is prevented. This risk may be further mitigated by the casing 31 of the check valve 271, 371 being disposable, whereby it may be replaced after each usage.

To provide a check valve integrated into a fluid line in this manner mitigates the risk for leakage associated with a connection between a separate check valve component and the fluid line. Furthermore, it does not require the mounting of the fluid line and the check valve to be performed in two separate steps. Instead, the arrangement may be mounted to the dialysis machine in one step, making the mounting easier for the operator.

Figure 29:
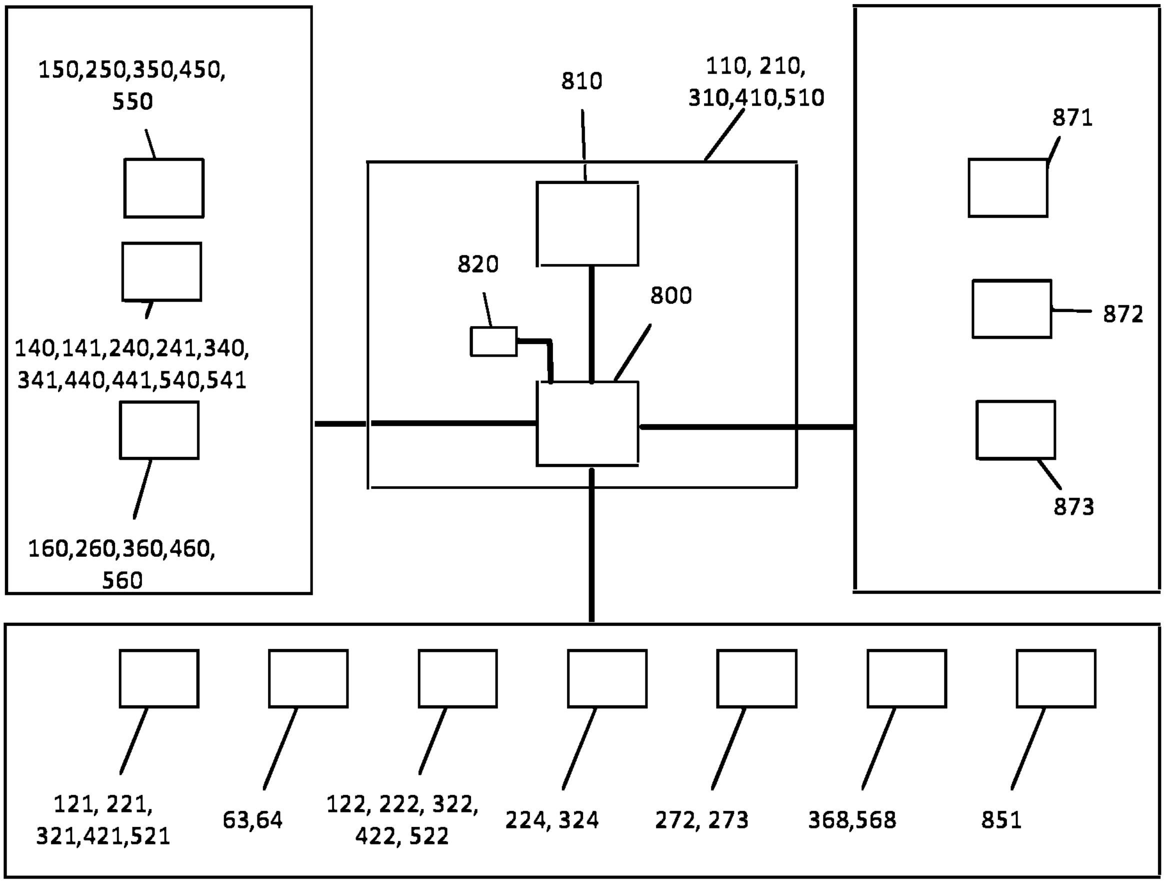
FIG. 29 schematically illustrates a controller arrangement for a dialysis system of one embodiment.

Referring to FIG. 29, the dialysis machine 110, 210, 310, 410, 510 may comprise a controller 800 which may be configured to control the operation of the dialysis machine, including the components of the dialysis machine and the components connected to said dialysis machine. The controller 800 may comprise a processor (one or more CPUs), a general purpose computer, special purpose computer, or other programmable data processing apparatus of the dialysis machine. Said controller 800 may further comprise a memory 820 for storing parameters and prompts.

Further, said controller is operatively connected to and may be configured to communicate with and receive signals from any one of the components of the dialysis machine and the components connected to said dialysis machine. The components include, but is not limited to the previously described sensors and pumping devices.

To allow for automatic control of the draining as well as the filling of the extracorporeal fluid circuit with rinse-back, the controller 800 may be configured to receive sensor signals from the sensors in the dialysis machine as well as the extracorporeal fluid circuit.

Thus, the controller 800 may be configured to receive sensor signals from any one of the following sensors provided in the dialysis machine and the extracorporeal fluid circuit. Said sensors may include the previously described level sensor 160, 260, 360, 460, 560, air sensor 150, 250, 350, 450, 550 and pressure sensors 140, 240, 340, 440, 540, 872, at least one blood sensor 871 and at least one flow sensor 873.

In one embodiment, the dialysis machine 110, 210, 310, 410, 510 may further comprise an operator alerting device 810 configured to present information to the operator based on signals provided by the controller 800. The controller 800 may thus be operatively connected to and configured to communicate with said operator alerting device 810. Said operator alerting device 810 may for example be a speaker configured to present the information via sound messages or a display for visually presenting the information. Alternatively, the operator alerting device 810 may comprise both a display and a speaker.

The controller may accordingly be configured to control the pumping device 121, 221, 321, 421, 521 and control said pumping device so as to pump the gas into the extracorporeal fluid circuit. This may be performed in response to input from the operator or automatically in response to a signal from the at least one blood sensor 871 indicative of that the concentration of blood is at a sufficiently low level. Alternatively, said signal from the blood sensor 871 may prompt the controller 800 to provide a signal to the operator alerting device 810. A message urging the operator to initiate the pumping of gas may then be presented to the operator via said operator alerting device.

Similarly, the controller 800 may be configured to control the pump arrangement 63, 64 for distribution of dialysis fluid to and from the dialyzer to achieve a net removal of remaining fluid from the dialyzer during the applying of negative pressure. This may be performed in response to operator input or as an automatic consequence of the pumping of the gas into the extracorporeal fluid circuit having been initiated. Alternatively, said initiation of the pumping of the gas may trigger the controller 800 to prompt the operator alerting device 810 to generate a message to the operator, urging the operator to initiate the controlling of the pump arrangement 63, 64. Thereby, the conveying of the remaining fluid removed from the extracorporeal fluid circuit to the drain of the dialysis machine is enabled.

Further, as described with reference to FIG. 13-19, said pump arrangement 63, 64 may be further controlled so as to introduce rinse-back fluid into the extracorporeal fluid circuit. Hence, the controller 800 may be further configured to control said pump arrangement 63, 36 so as to introduce rinse-back fluid into the extracorporeal fluid circuit. This may be performed in response to a sensor signal or the operators input.

The controller 800 may also be configured to control the peristaltic blood pump 122, 222, 322, 422, 522 so as to generate a flow of the rinse-back fluid in the direction of the dialyzer. This may be performed after the rinse-back fluid has been introduced by for example the dialysis fluid pump 224, 324 or the pump arrangement 63, 64 or in response to an input of the operator.

Further, said controller 800 may be configured to control the blood pump 222, 322, 422 so as to generate the pushback flow of blood in the direction of the arterial line for emptying of the arterial line of blood. This may be performed prior to the generating of the flow of the rinse-back fluid in the direction of the dialyzer. Said controller 800 may be further configured to stopping said generating of pushback flow when the arterial line is substantially emptied of blood. The stopping may be performed automatically in response to the at least one blood sensor detects a blood concentration below a maximum allowed threshold value in the arterial line or in response the operators input. At that point, the controller 800 may stop the blood pump.

With reference to a free-end draining method, said controller 800 may be further configured to activate the peristaltic blood 322,522 pump to suck gas into the extracorporeal fluid circuit, this may be performed with the turning around of the venous drip chamber 331,531. This may be performed in response to the operators input. However it may also be performed automatically by the controller activating the blood pump 322,522 in response to the at least one blood sensor 871 detecting a blood concentration below a maximum allowed threshold value in the extracorporeal fluid circuit. Said threshold value may be indicative of when it is suitable to enable the introduction of the gas. The input from the at least one blood sensor may also trigger the controller 800 to prompt the operator alerting device 810 to present information indicating that the introduction of gas should be performed.

Further referring to said free-end draining method, the clamp 368,568 may be an actuatable pinching type clamp configured to be controlled by the controller 800. The locking of the clamp 368,568 to the second port of the extracorporeal fluid circuit may be performed through the provision of said controller 800. The locking may be performed in response to the initiation of the sucking of gas via the blood pump after introducing the extracorporeal fluid circuit with the rinse-back fluid prior to the sucking of gas into the fluid circuit via the first port of said fluid circuit.

Again referring to FIG. 29, the controller 800 is configured to control the dialysis fluid pump 224,324 described with reference to the draining variants utilizing said dialysis fluid pump presented with reference to FIG. 5-12. Hence, said controller may be configured to activate said dialysis fluid pump 202,302 so as to generate a flow of the rinse-back fluid in the direction of the venous line through the dialyzer. This may be performed in response to an operators input.

Also, the clamp arrangement 272,273 may be actuatable pinch type clamps, whereby the dialysis fluid pump 224 is connected to the extracorporeal fluid circuit via the actuatable clamp arrangement 272,273. The controller is configured to control the actuatable clamp arrangement 272, 273. Hence, the method of draining may further comprise releasing said clamp arrangement 272,273 forming fluid communication between the dialysis fluid pump 224 and the extracorporeal fluid circuit prior to the introduction of the rinse-back fluid into said extracorporeal fluid circuit by controlling the said clamp arrangement through the controller 800.

Further, the method of draining of the extracorporeal fluid circuit may comprise additional security measures in order to substantially mitigate the risk for air embolism of potentially connected patient or damage as well as contamination of essential components of the dialysis machine or the components connected to said dialysis machine.

For example, the method of draining may further comprise terminating the draining in response to an exceeding of a predetermined drained fluid volume. This is possible due to the extracorporeal fluid circuit having a fixed volume, thus the predetermined volume drained is indicative of whether remaining fluid is left in the extracorporeal fluid circuit. Accordingly a simple and efficient manner to detect whether remaining fluid is left in the extracorporeal fluid circuit is achieved.

The extracorporeal fluid circuit may thus be provided with the at least one flow sensor 873 configured to measure the flow of fluid through said extracorporeal fluid circuit. Alternatively, this may be performed by measuring of the rate of net removal from the dialyzer in comparison to the flow of rinse-back fluid provided into the extracorporeal fluid circuit.

The method of draining of the extracorporeal fluid circuit may further comprise terminating the draining in response to a predetermined pressure in the extracorporeal fluid circuit. This may be achieved by the provision of the at least one pressure sensor 140, 240, 340, 440, 540 configured to measure or monitor the pressure inside said extracorporeal fluid circuit. Alternatively, said sensors may be configured to both measure and monitor said pressure. A rapid change of pressure may thus indicate that little or no remaining fluid is left in the extracorporeal fluid circuit. Hence, a fully automated method for terminating the draining if little or no remaining fluid is left in the extracorporeal fluid circuit is enabled, for example by the controller 800 being configured to terminate the draining in response to a detected pressure change in the extracorporeal fluid circuit.

Preventing the draining in response to a predetermined pressure may also include the pressure exceeding a certain threshold value associated with for example an increased risk for damaging to the components connected to the extracorporeal fluid circuit or a risk for a potentially connected patient.

Further, said terminating of the draining in response to a predetermined pressure may be achieved by the provision of the pressure sensor(s) 872 of the dialyzer fluid circuit. Accordingly, the pressure sensor(s) are configured to measure or monitor the pressure inside the dialyzer fluid circuit. Alternatively, said sensors may be configured to both measure and monitor said pressure. A rapid change of pressure may thus indicate that little or no remaining fluid is left in the extracorporeal fluid circuit. Hence, a fully automated method for terminating the draining if little or no remaining fluid is left in the extracorporeal fluid circuit is enabled, for example by the controller 800 being configured to terminate the draining in response to a detected pressure change in the dialyzer fluid circuit. Additionally, the monitoring of the pressure in the dialyzer fluid circuit allows for an automatic response if the pump arrangement 63,64 malfunctions or provides an insufficient flow of dialysis fluid, Preventing the draining in response to a predetermined pressure may also include the pressure exceeding a certain threshold value associated with for example an increased risk for damaging to the components connected to the extracorporeal fluid circuit.

The applying of negative pressure on the dialyzer fluid circuit may also be terminated or prevented in response to if blood is detected in the extracorporeal fluid circuit. Accordingly, the at least one blood sensor 871 may detect blood in the fluid flowing through said fluid circuit which in turn prompts the controller 800 to terminate the applying of negative pressure. For example, the terminating of the applying of the negative pressure may be performed by preventing or terminating the pumping performed by the pumping device 121, 221, 321, 421, 521. By terminating or preventing the draining when blood is detected all of the blood may be returned to the patient before the extracorporeal fluid circuit is emptied.

In one embodiment, the controller 800 may be configured to execute the controlling of any one of the pump arrangement 63,64 the dialysis fluid pump 224,324, the pumping device 121, 221, 321, 421, 521 i.e. the air pump based on a set of predefined parameters. The predefined parameters may include the flow speed set by the pumps as well as a timing sequence for the sequence and timing of each operation of each pump involved in the method.

Due to the volume of the extracorporeal fluid circuit being known beforehand and predefined, at least a part of the draining may be fully automated simply by controlling of the pump speed and activation timings. This allows for at least a partly automation of the draining method without significant reliance on sensors and operator input, whereby a more robust and reliable draining method may be achieved due to a lower susceptibility for sensor errors or human errors performed by the operator.

Embodiments of the present technology have been described herein with reference to a method for draining an extracorporeal fluid circuit. It will be understood that the method may be implemented in the form of an entirely hardware embodiment, or an embodiment combining software and hardware aspects including computer program instructions to control the operation of the dialysis machine, including the components of the dialysis machine and the components connected to said dialysis machine, i.e the sensors and pumps.

A computer program product may comprise a computer-readable medium, having thereon: computer program code means including said computer program instructions. The computer program instructions may be provided to the controller 800, which may comprise circuitry or a program-controller configured to run said program instructions, such that the instructions when loaded and executed create means for implementing the specified functions of the programs to operate the dialysis machine accordingly. Alternatively, controller may comprise both circuitry and a program-controller configured to run said program instructions.

For clarification an example dialysis machine comprising the controller 810 for performing the method of draining will be described briefly below, reference is made to the embodiments described with reference to FIG. 1-28.

The dialysis machine 110, 210, 310, 410, 510 is connected to an extracorporeal fluid circuit 100, 200, 300, 400, 500 and a dialyzer 130, 230, 330, 430, 530 via a dialyzer fluid circuit 193, 194, 293, 294, 393, 394, 493, 494, 593, 594 and a pump arrangement 63, 64 for distribution of dialysis fluid to and from the dialyzer 130, 230, 330, 430, 530, 630.

The extracorporeal fluid circuit 100, 200, 300, 400, 500 comprises an arterial line 101, 201, 301, 401, 501 connectable to a patient for drawing blood from the patient and a venous line 102, 202, 302, 402, 502 connectable to the patient for returning blood to the patient.

The dialysis machine comprises the controller 800 and a pumping device 121, 221, 321, 421, 521 connected to the extracorporeal fluid circuit 100, 200, 300, 400, 500, 600 for pumping of gas intro said extracorporeal fluid circuit.

The controller 800 is operatively connected to said pumping device and the pump arrangement 63, 64. The controller 800 is hence configured to control said pumping device and pump arrangement so as to after treatment termination drain 1000, 2000, 3000 remaining fluid from said extracorporeal fluid circuit through the dialyzer 130, 230, 330, 430, 530, 630.

As previously described, the remaining fluid may be drained through the dialyzer fluid circuit of the dialyzer.

The pumping device 121, 221, 321, 421, 521 may be configured to pump gas into the extracorporeal fluid circuit 100, 200, 300, 400, 500, 600 via an inlet 109, 209, 309, 391, 409, 509, 591, 691 to push the remaining fluid towards the dialyzer 130, 230, 330, 430, 530, 630 for draining through the dialysis machine 110, 210, 310, 410, 510, 610.

The pumping device 121, 221, 321, 421, 521 may be an air pump.

The controller 800 may further be configured to initiate an introducing of a rinse-back fluid 1010, 2010, 3010 into the extracorporeal fluid circuit 100, 200, 300, 400, 500, 600 prior to the draining 1000, 2000, 3000 for filling the extracorporeal fluid circuit 100, 200, 300, 400, 500, 600.

The controller 800 may also be configured to control 1030, 2030, 3030 said pump arrangement so as to achieve a net removal of remaining fluid from the dialyzer 130, 230, 330, 430, 530, 630 and the extracorporeal fluid circuit 100, 200, 300, 400, 500 during the pumping of gas.

The dialysis machine 110, 210, 310, 410, 510, 610 may further be connected to a peristaltic blood pump 122, 222, 322, 422, 522 connected to the arterial line 101, 201, 301, 401, 501, 601. Said peristaltic blood pump being operatively connected to the controller 800 whereby the controller 800 is configured to activate 1005, 2005, 3005 said peristaltic blood pump 122, 222, 322, 422, 522 so as to generate a flow of the rinse-back fluid in the direction of the dialyzer 130, 230, 330, 430, 530, 630.

To enable closed-circuit draining, the arterial line 101, 201, 401 may comprise a first port 191, 291, 491 connectable to the patient and the venous line 102, 202, 402 comprises a second port 192, 292, 492 connectable to the patient, said ports being arranged to be connectable to each other prior to the pumping of gas into the extracorporeal fluid circuit 100, 200, 400.

Said first port 191, 691 may further arranged to be connectable to a rinse-back fluid container 170 prior to introducing the rinse-back fluid into the fluid circuit 100, 600.

Further, the controller 800 may be configured to control the pump arrangement 63,64 so as to drain the remaining rinse-back fluid in the rinse-back fluid container 170 through the dialyzer 130, 630 after treatment termination.

In accordance with the embodiments described with reference to FIGS. 5-17 and FIG. 21, the controller 800 may be configured to activate the peristaltic blood pump 222, 322, 422 so as to generate 2003, 3003 a pushback flow of blood in the direction of the arterial line 201, 301, 401, 601 for emptying of the arterial line 201, 301, 401, 601 of blood prior to the generating of the flow of the rinse-back fluid in the direction of the dialyzer 230, 330, 430, 630.

Furthermore, the controller 800 may be configured to stop 2004, 3004 said peristaltic blood pump 222, 322, 422 so as to stop said generating of pushback flow when the arterial line 201, 301, 401 is substantially emptied of blood.

Referring to the embodiments described with reference to FIG. 5-12, the dialysis machine 210, 310 may also be connected to a dialysis fluid pump 224, 324 connected to the extracorporeal fluid circuit 200, 300, 600, whereby the controller 800 is operatively connected to said dialysis fluid pump and said controller is configured to activate the dialysis fluid pump 224, 324 so as to generate a flow of the rinse-back fluid in the direction of the venous line (202, 302, 602) through the dialyzer 230, 330, 630. Accordingly, the flow of rinse-back fluid may flow through the dialyzer blood line by flowing through the dialyzer.

The dialysis fluid pump 224 may further connected to the extracorporeal fluid circuit 200 both downstream and upstream of the dialyzer 230 via a clamp arrangement 272, 273. The clamp arrangement 272, 273 is arranged to be released 2002 so as to form fluid communication between the dialysis fluid pump 224 and the extracorporeal fluid circuit 200 prior to the introduction of the rinse-back fluid into said extracorporeal fluid circuit 200.

Said dialysis fluid pump 224 may be connected to the fluid circuit via a check valve 271, the check valve 271 being configured to prevent fluid flow back to the dialysis fluid pump 224. The check valve may be a disposable valve.

To enable more efficient draining in a dialysis machine not connected to such a dialysis fluid pump, the controller 800 may be configured to control the pump arrangement 63, 64 so as to introduce rinse-back fluid into the extracorporeal fluid circuit 400, 500.

In order to achieve the draining without connection of the arterial line and the venous line, a venous drip chamber 331, 531531 connected to the venous line 302, 502, 602 may be arranged to be turned around 3013 for emptying said venous drip chamber 331, 531531 of remaining fluid so as and thereby introduce gas into the extracorporeal fluid circuit 300, 500, 600.

Accordingly, the controller 800 may be configured to activate the peristaltic blood pump 322, 522 to suck gas into the extracorporeal fluid circuit 300, 500, 600 via the first port 391, 591, 691.

Furthermore, a clamp 368, 568 may be arranged to be locked 3011 to the second port 392, 592 after introducing 3010 of the extracorporeal fluid circuit 300, 500 with said rinse-back fluid and be released 3012 prior to sucking of the gas into the fluid circuit via the first port 391, 591.

To achieve a more safe handling of the drained fluid the controller 800 may be configured to control the pumping arrangement 63, 64 so as to convey 1060, 2060, 3060 the remaining fluid removed from the extracorporeal fluid circuit to a drain 68 of the dialysis machine 110, 210, 310, 410, 510.

To achieve a dialysis machine allowing for a safer draining, the controller 800 may be configured to terminate the draining (1000, 2000, 3000) in response to an exceeding of a predetermined drained fluid volume.

The controller may be configured to terminate the draining 1000, 2000, 3000 in response to reaching of a predetermined pressure in the dialyzer fluid circuit 193, 194, 293, 294, 393, 394, 493, 494, 593, 594, 693, 694 or the extracorporeal fluid circuit 100, 200, 300, 400, 500, 600.

The controller 800 may also be configured to prevent pumping of gas by the pumping device 121, 221, 321, 421, 521 in response to if blood is detected in the extracorporeal fluid circuit 100, 200, 300, 400, 500, 600.

Similarly, the controller 800 may be configured to terminate pumping of gas by the pumping device 121, 221, 321, 421, 521 in response to if blood is detected in the extracorporeal circuit 100, 200, 300, 400, 500, 600.

Referring to the embodiment described with reference to FIG. 21, a pre-reinfusion clamp 851 may be arranged to be opened prior to the draining 1000, 2000, 3000 and closed after the rinse-back fluid has been introduced into the extracorporeal circuit 600.

The arterial line 601 may be arranged to be attached to a service line 651 prior to the draining 1000, 2000, 3000.

To further exemplify, an example of a dialysis machine comprising the controller 810 for performing the method of filling will be described briefly below, reference is made to the embodiments described with reference to FIG. 1-28.

The dialysis machine 210, 310 is connected to a dialyzer 230, 330, an extracorporeal fluid circuit 200, 300 and a pumping device 224, 324 connected to the extracorporeal fluid circuit 200, 300.

Said extracorporeal fluid circuit 200, 300 comprises an arterial line 201, 301 connectable to a patient for drawing blood from the patient and a venous line 202, 302 connectable to the patient for returning blood to the patient, the dialysis machine comprising a controller 800 operatively connected to said pumping device.

Accordingly, the controller is configured to control the pumping device 224, 324 to generate a flow of rinse-back fluid in the direction of the second port 292, 392 through the dialyzer 230, 330, thereby generating pumping of rinse-back fluid 2002 into the extracorporeal fluid circuit 200, 300 thus filling said extracorporeal fluid circuit. Accordingly, the flow of rinse-back fluid is generated through the dialyzer blood line of the dialyzer in the direction of the second port. The flow of rinse-back fluid may hence be generated through the dialyzer blood line to the venous line.

The controller 800 may be further configured to control the pumping device 224, 324 so as to pump 2001 to generate a pushback flow of blood in the direction of the first port 291, 391 so as to empty the arterial line 201, 301 of blood.

Accordingly, the controller 800 may be configured to activate 2003 a peristaltic blood pump 222, 322 connected to the extracorporeal fluid circuit 200, 300 and operatively connected to the controller 800 so as to generate flow of rinse-back fluid in the direction of the second port 292, 392.

Furthermore, the controller 800 may be configured to stop 2004 said peristaltic blood pump 222, 322 so as to stop said pumping of pushback flow when the arterial line 201, 301 is substantially emptied of blood.

The pumping device 224 may be connected to the extracorporeal fluid circuit 200 via a clamp arrangement 272, 273 both downstream and upstream of the dialyzer 230, whereby said clamp arrangement is arranged to be released 2002 so as to form fluid communication between the pumping device 224 and the extracorporeal fluid circuit 200 prior to the pumping of the rinse-back fluid into said extracorporeal fluid circuit 200.

Said pumping device 224, 324 may be a dialysis fluid pump, the dialysis fluid pump being arranged to provide dialysis fluid to the extracorporeal fluid circuit 200, 300.

In one embodiment, lysating fluid may be introduced after the rinse-back fluid into the fluid circuit to break down any remaining red blood cells in the extracorporeal fluid circuit. Due to the remaining red blood cells effectively being broken down a more complete rinsing of the extracorporeal fluid circuit may be achieved as a result of the internal fluid of the red blood cells becoming easier to rinse away together with the fluid. The introduction and filling with the lysating fluid may be performed in a similar manner to the introduction of the rinse-back fluid in any of the above described embodiments and will be explained in more detail below.

Figure 30:
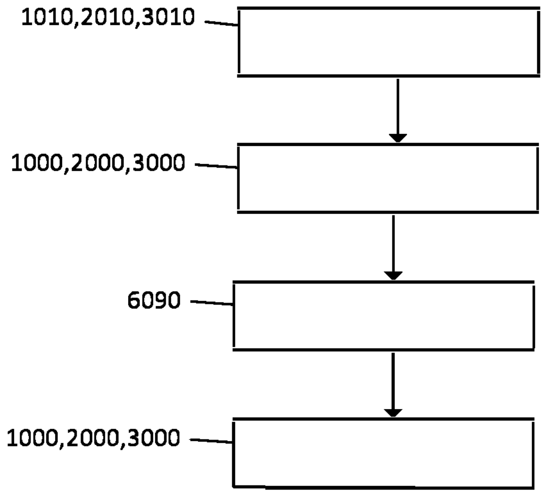
FIG. 30 shows a method for draining an extracorporeal fluid circuit of one embodiment.

Referring to FIG. 30, the method for draining the extracorporeal fluid circuit 100, 200, 300, 400, 500, 600 utilizing the dialysis machine 110, 210, 310, 410, 510, 610 is schematically depicted. The dialysis machine is as depicted in FIG. 1-21 connected to the dialyzer 130, 230, 330, 430, 530, 630 and said extracorporeal fluid circuit. Said extracorporeal fluid circuit comprises the arterial line connectable to a patient, for drawing blood from the patient and the venous line connectable to the patient for returning blood to the patient.

According to this embodiment, the method comprises, after treatment termination, draining 1000, 2000, 3000 remaining fluid from said extracorporeal fluid circuit through the dialyzer. As described with reference to FIG. 1-20, the method comprises draining through the dialyzer fluid circuit of the dialyzer. Expressed differently, the draining through the dialyzer is performed by means of draining through the dialyzer fluid circuit.

The method further comprises introducing the rinse-back fluid 1010, 2010, 3010 into the extracorporeal fluid circuit prior to the draining 1000, 2000, 3000 for filling the extracorporeal fluid circuit 100, 200, 300, 400, 500, 600, in accordance with the draining described with reference to FIG. 22-28.

As depicted in FIG. 30 the method further comprises introducing a lysating fluid 6090 into the extracorporeal fluid circuit 100, 200, 300, 400, 500, 600 after the introduction of the rinse-back fluid 1010, 2010, 3010 for filling the extracorporeal fluid circuit 100, 200, 300, 400, 500, 600 prior to the draining 1000, 2000, 3000.

The lysating fluid is adapted to break down the structure of the red blood cells. Thereby, the additional flushing of the extracorporeal fluid circuit may result in a cleaner extracorporeal fluid circuit after draining. Depending on the efficiency of the lysating fluid the extracorporeal fluid circuit may not be classified as hazardous waste or at least a lower classified waste, which may result in substantial savings for the clinic with regards to disposal handling costs. Further, the risk for red blood cells sticking to the extracorporeal fluid circuit after draining may be reduced, which may allow for a cleaner disposal process associated with a lower risk for contamination.

The lysating fluid may for example comprise citric acid, whereby the lysating fluid may be a solution comprising citric acid.

Also or alternatively, the lysating fluid may comprise RO-water (RO=Reverse Osmosis), whereby the lysating fluid may be a solution comprising RO-water, i.e. water subjected to reverse osmosis to remove ions, molecules and larger particles. Thereby the water is able to break down the structure of red blood cells.

In one embodiment, the lysating fluid comprises both RO-water and citric acid.

The lysating fluid may be a liquid. Similarly, the rinse-back fluid may be a liquid as well.

The extracorporeal fluid circuit is drained through the dialyzer by applying a negative pressure on the dialyzer fluid circuit relative the extracorporeal fluid circuit, as described with reference to FIG. 1-28.

The negative pressure applied on the dialyzer fluid circuit relative the extracorporeal fluid circuit may in other words be considered as inducing a pressure difference between the extracorporeal fluid circuit and the dialyzer fluid circuit to create suction, e.g. flow, of fluid into the dialyzer fluid circuit from the extracorporeal fluid circuit.

Expressed differently, the dialysis fluid circuit pressure, relative to the extracorporeal fluid circuit pressure, may be such that a suction of fluid into the dialysis fluid circuit from the extracorporeal fluid circuit is created.

Accordingly, the fluid which remains in the extracorporeal fluid circuit after introduction of the lysating fluid is drained through the dialyzer in a similar manner to the remaining fluid after the introduction of the rinse-back fluid as previously described with reference to FIG. 1-28. Said remaining fluid may be drained through the dialyzer fluid circuit of the dialyzer.

In one embodiment, the method comprises draining 1000, 2000, 3000 remaining fluid from the extracorporeal fluid circuit 100, 200, 300, 400, 500, 600 through the dialyzer 130, 230, 330, 430, 530, 630 after introduction of the rinse-back fluid 1010, 2010, 3010 and prior to the introduction of lysating fluid 6090 into said extracorporeal fluid circuit.

Hence, the extracorporeal fluid circuit 100, 200, 300, 400, 500, 600 may be filled with gas to empty the said circuit from rinse-back fluid and remaining fluid from the dialysis before being filled with lysating fluid. After the extracorporeal fluid circuit is substantially filled with lysating fluid, the remaining fluid in the form of lysating fluid and remaining rinse-back fluid and remaining fluid from the dialysis, said extracorporeal fluid circuit is emptied of fluid through the dialyzer in a similar manner, i.e. by filling the extracorporeal fluid circuit with gas. Accordingly, the extracorporeal fluid circuit is drained to be substantially filled with gas both after the introduction of the rinse-back fluid and the lysating fluid.

As previously described with reference to filling the extracorporeal fluid circuit with gas after the introduction of rinse-back fluid the gas may be introduced by means of an air pump into a closed circuit or by means of introducing air via free ports of the circuit.

In one embodiment, the method comprises draining 1000, 2000, 3000 remaining fluid from the extracorporeal fluid circuit 100, 200, 300, 400, 500, 600 through the dialyzer 130, 230, 330, 430, 530, 630 after introduction of the rinse-back fluid 1010, 2010, 3010 and prior to the introduction of lysating fluid 6090 into said extracorporeal fluid circuit. Hence, the extracorporeal fluid circuit is not filled with gas after the introduction of the rinse-back fluid, instead the lysating fluid is introduced so as to push the rinse-back fluid towards and through the dialyzer, e.g. to the drain of the dialysis machine via the dialyzer fluid circuit.

The intermediate step of draining by means of filling the extracorporeal fluid circuit with gas after the introduction of rinse-back fluid is thereby not required, which enables a faster draining process.

In accordance with the draining described with reference to FIG. 1-28, the draining of lysating fluid may be achieved by the negative pressure applied on the dialyzer fluid circuit 193, 194, 293, 294, 393, 394, 493, 494, 593, 594 relative the extracorporeal fluid circuit 100, 200, 300, 400, 500, 600 being applied by introducing of gas into the extracorporeal fluid circuit 100, 200, 300, 400, 500, 600.

The negative pressure applied on the dialyzer fluid circuit relative the extracorporeal fluid circuit may in other words be considered as inducing a pressure difference between the extracorporeal fluid circuit 100 and the dialyzer fluid circuit 193, 194, 293, 294, 393, 394, 493, 494, 593, 594 to create suction, e.g. flow, of fluid into the dialyzer fluid circuit 193, 194, 293, 294, 393, 394, 493, 494, 593, 594 from the extracorporeal fluid circuit.

The introducing of the gas is performed by pumping of gas into the extracorporeal fluid circuit 100, 200, 300, 400,

500, 600 via the inlet 109, 209, 309, 391, 409, 509, 591, 691. The remaining fluid is pushed towards the dialyzer 130, 230, 330, 430, 530, 630 for draining through the dialysis machine 110, 210, 310, 410, 510, 610.

The gas is pumped into the extracorporeal fluid circuit 100, 200, 300, 400, 500, 600 with the pumping device 121, 221, 321, 421, 521 connected to the extracorporeal fluid circuit 100, 200, 300, 400, 500, 600 via the inlet 109, 209, 309, 391, 409, 509, 609. The pumping device 121, 221, 321, 421, 521 may be an air pump.

As is evident from FIG. 1-21 the dialysis machine 110, 210, 310, 410, 510, 610 is connected to the peristaltic blood pump 122, 222, 322, 422, 522 connected to the arterial line 101, 201, 301, 401, 501, 601. To enable the fluid in the extracorporeal fluid circuit, which may be for example rinse-back fluid or lysating fluid, to be forced towards the dialyzer, the peristaltic blood pump may be utilized. The method may thus further comprise activating 1005, 2005, 3005 said peristaltic blood pump 122, 222, 322, 422, 522 to generate a flow of the rinse-back fluid and/or lysating fluid in the direction of the dialyzer 130, 230, 330, 430, 530, 630 during the introduction of rinse-back fluid and lysating fluid, respectively.

Referring to the embodiments of the dialysis system depicted in for example FIGS. 1-10 and 13-17 the arterial line 101, 201, 401 comprises the first port 191, 291, 491 connectable to the patient and the venous line 102, 202, 402 comprises the second port 192, 292, 492 connectable to the patient. The method comprises connecting 1015, 2015 the first port 191, 291, 491 to the second port 192, 292, 492 prior to introducing the gas into the extracorporeal fluid circuit 100, 200, 400.

Hence, the lysating fluid is introduced in a closed circuit after the rinse-back fluid has been introduced. This allows for a more clean draining process. If the ports are connected to each other, the remaining draining process may be performed by the dialysis machine automatically. Furthermore the connecting of the ports is a relatively simple measure to perform for the operator compared to the actions necessary to perform a conventional draining.

In one embodiment, the first and second port are connected prior to the introduction of the gas and the consequent filling of the extracorporeal fluid circuit with gas is performed prior to the introducing of the lysating fluid into said extracorporeal fluid circuit.

Referring to the embodiment of the dialysis system depicted in for example FIG. 5-12 or FIG. 21, the dialysis machine 210, 310 is connected to the dialysis fluid pump 224, 324 in turn connected to the extracorporeal fluid circuit 200, 300. The introducing of the rinse-back fluid into the extracorporeal fluid circuit 200, 300 to fill said extracorporeal fluid circuit 200, 300 is performed by activating the dialysis fluid pump 224, 324 so as to generate a flow of the rinse-back fluid in the direction of the venous line 202, 302 through the dialyzer 230, 330, e.g. through the dialyzer blood line of the dialyzer.

Figure 31:
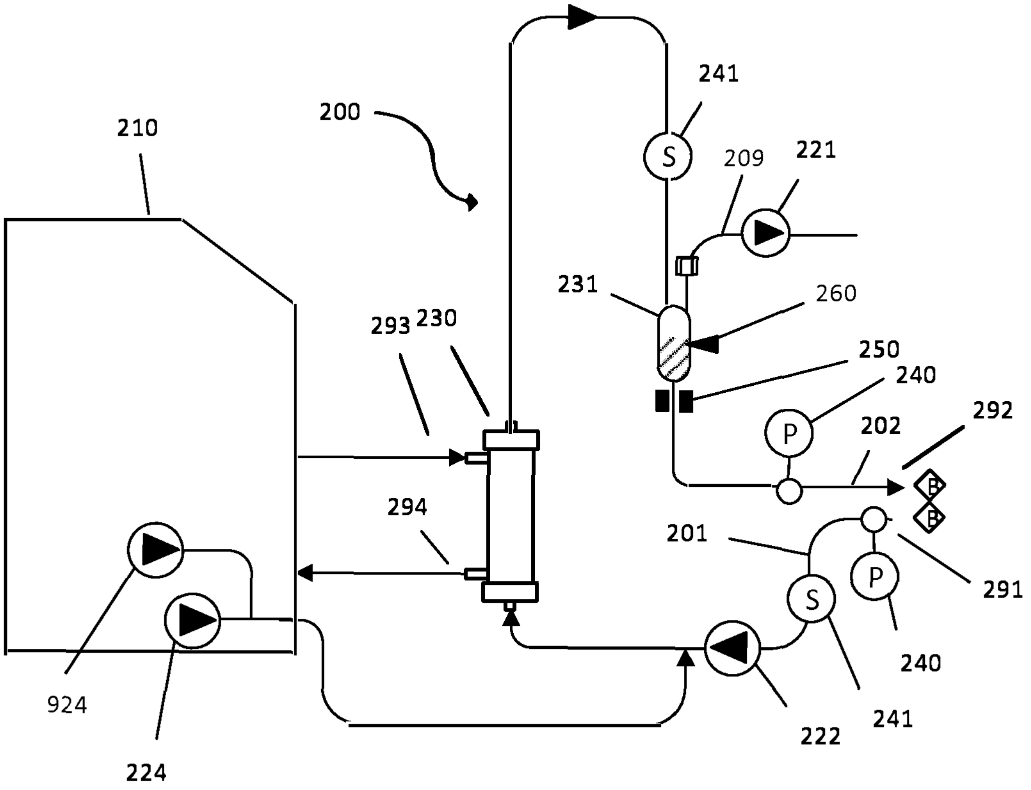
FIG. 31 schematically illustrates a dialysis system of one embodiment.

With reference to FIG. 31, a lysating fluid pump 924 may be utilized for filling the extracorporeal fluid circuit with lysating fluid. The dialysis machine 210 is connected to the lysating fluid pump 924 connected to the extracorporeal fluid circuit 200. Introducing of the lysating fluid into the extracorporeal fluid circuit 200 to fill said extracorporeal fluid circuit is performed by activating the lysating fluid pump 924 to generate a flow of the lysating fluid in the direction of the venous line 202 through the dialyzer 230, e.g. through the dialyzer blood line of the dialyzer 230.

As depicted in for example FIGS. 11-12 and 18-19, the venous drip chamber 331, 531 may be turned around, i.e. turned upside-down to allow for emptying of fluid and thereby introduce gas into the extracorporeal fluid circuit. This may be performed both in conjunction with a draining of rinse-back fluid and lysating fluid in the extracorporeal fluid circuit. The method may accordingly further comprise turning 3013 the venous drip chamber 331, 531 connected to the venous line 302, 502 around for emptying said venous drip chamber 331, 531 of remaining fluid to introduce gas into the extracorporeal fluid circuit 300, 500.

The gas may be introduced into the extracorporeal fluid circuit 300, 500 by activation of the peristaltic blood pump 322, 522 to, i.e. in order to, suck gas into the extracorporeal fluid circuit 300, 500 via the first port 391, 591. Thereby, the rinse-back fluid or the lysating fluid present in the extracorporeal fluid circuit is pushed towards the dialyzer. This may be performed after the introduction of the rinse-back fluid or the lysating fluid, respectively depending on whether it is performed after introduction of rinse-back fluid or lysating fluid into the extracorporeal fluid circuit.

To avoid spillage, the method may further comprise locking 3011 the clamp 368, 568 to the second port 392, 592 after introducing 3010 the extracorporeal fluid circuit 300, 500 with said rinse-back fluid and releasing 3012 said clamp 368, 568 prior to sucking the gas into the fluid circuit via the first port 391, 591.

In one embodiment, the pump arrangement 63, 64 is controlled to achieve a net removal of fluid from the extracorporeal fluid circuit, by controlling the pump arrangement 63, 64 at a higher flow rate than the peristaltic blood pump 322, 522. Hence, the risk for fluid exiting through the port 392, 592 may be mitigated.

The locking and releasing of the clamp may be performed both during the draining of the rinse-back fluid and the lysating fluid to allow for the draining through the dialyzer.

Turning to the embodiments of FIGS. 1-19 and the pump arrangement of FIG. 20, in which the rinse-back fluid is provided by means of controlling the pump arrangement 63, 64, are depicted. Hence, the rinse-back fluid is introduced into the extracorporeal fluid circuit 400, 500 through control of the pump arrangement 63, 64.

In one embodiment, the pump arrangement 63, 64 further comprises a lysating fluid pump for distribution of lysating fluid to and from the dialyzer 130, 230, 330, 430, 530. Accordingly, the pump arrangement 63,64 may further comprise a lysating fluid pump adapted to distribute lysating fluid to the extracorporeal fluid circuit via the dialyzer fluid circuit 193, 194, 293, 294, 393, 394, 493, 494, 593, 594, 693, 694. The lysating fluid pump may thus be integrated into the pump arrangement 63, 64.

The lysating fluid pump, which may be a part of the pump arrangement 63, 64 or the independently controlled lysate pump 924, may be operatively connected to the controller 800. Said controller may be configured to control said lysating fluid pump to selectively distribute lysating fluid into the extracorporeal fluid circuit.

The method may thus further comprise controlling said pump arrangement 63, 64 to distribute lysating fluid into the extracorporeal fluid circuit 100, 200, 300, 400, 500 after the rinse-back fluid has been introduced into said extracorporeal fluid circuit 100, 200, 300, 400, 500.

The pump arrangement 63, 64 may be controlled to distribute lysating fluid into the extracorporeal fluid circuit 100, 200, 300, 400, 500 maintaining a removal of fluid from the dialyzer 130, 230, 330, 430, 530, 630 via the dialyzer fluid circuit and the extracorporeal fluid circuit 100, 200, 300, 400, 500.

Referring to the embodiment of the dialysis system depicted in for example FIGS. 1-4 and the embodiment of FIG. 21, the draining method further comprises connecting 1004 the arterial line 101, 601 to the rinse-back fluid container 170 prior to introducing the rinse-back fluid into the fluid circuit 100, 600. The remaining rinse-back fluid may be drained through the dialyzer 130, 630 after treatment termination. As previously described, the remaining rinse-back fluid may be drained through the dialyzer fluid circuit of the dialyzer.

Figure 32:
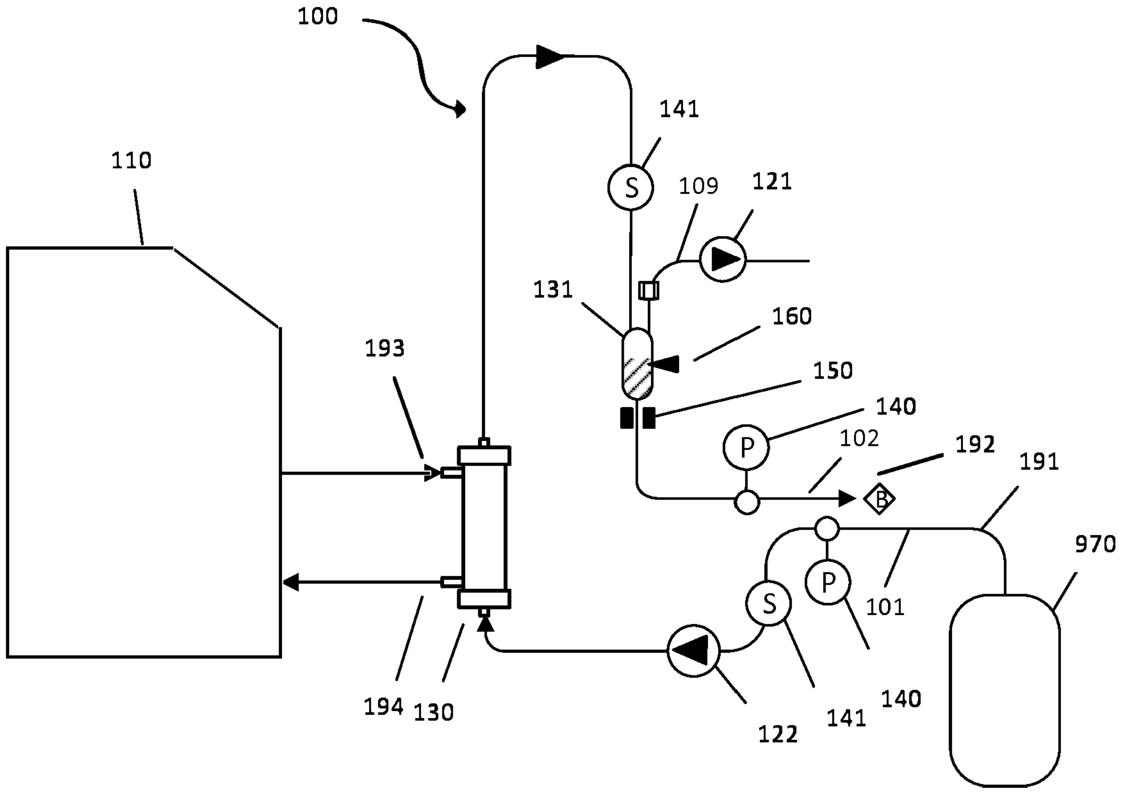
FIG. 32 schematically illustrates a dialysis system of one embodiment.

Similarly to rinse-back fluid, the lysating fluid may be introduced by means of a lysating fluid container 970, as depicted in FIG. 32. The method may consequently further comprise connecting 6004 the arterial line 101, 601 to the lysating fluid container 970 prior to introducing the lysating fluid into the fluid circuit 100, 600. The remaining lysating fluid may be drained through the dialyzer 130, 630 after treatment termination.

The lysating fluid may be provided by means of disconnecting the rinse-back fluid container 170 from the arterial line and instead connect the lysating fluid container 970. Alternatively, the lysating fluid container 970 may be connected to the arterial line via a separate inlet.

In one embodiment, the draining further comprises conveying 1060, 2060, 3060 the remaining fluid removed from the extracorporeal fluid circuit to the drain 68 of the dialysis machine 110, 210, 310, 410, 510, as depicted in FIG. 20. The remaining fluid may be moved to the drain 68 both after the introduction of the rinse-back fluid and after the introduction of the lysating fluid, respectively.

The draining may further be controlled by means of terminating the draining 1000, 2000, 3000 in response to an exceeding of a predetermined drained fluid volume, i.e. when sufficient draining has been achieved. Further the draining 1000, 2000, 3000 may be terminated in response to a predetermined pressure in the dialyzer fluid circuit 193, 194, 293, 294, 393, 394, 493, 494, 593, 594, 693, 694.

As a safety measure the applying of negative pressure may be prevented in response to if blood is detected in the extracorporeal fluid circuit 100, 200, 300, 400, 500, 600. Additionally, the applying of negative pressure may be terminated in response to if blood is detected in the extracorporeal circuit 100, 200, 300, 400, 500, 600.

According to an aspect, the dialysis machine 110, 210, 310, 410, 510 is provided. The dialysis machine is connected to the extracorporeal fluid circuit 100, 200, 300, 400, 500 and the dialyzer 130, 230, 330, 430, 530, wherein said extracorporeal fluid circuit 100, 200, 300, 400, 500 comprises the arterial line 101, 201, 301, 401, 501 connectable to a patient for drawing blood from the patient and the venous line 102, 202, 302, 402, 502 connectable to the patient for returning blood to the patient. The dialysis machine is configured to perform the method for draining according to any of the above described embodiments.

Aspects of the present technology will be descried below with reference to the following section disclosing methods for draining an extracorporeal fluid circuit and dialysis machines for executing the methods.

Further, another aspect of present technology will be descried below with reference to the following section disclosing a method for filling an extracorporeal fluid circuit with rinse-back fluid and a dialysis machine for executing said filling method.

According to an aspect a method for draining an extracorporeal fluid circuit 100, 200, 300, 400, 500, 600 utilizing a dialysis machine 110, 210, 310, 410, 510 is provided. The dialysis machine 110, 210, 310, 410, 510, 610 is connected to a dialyzer 130, 230, 330, 430, 530, 630 and said extracorporeal fluid circuit 100, 200, 300, 400, 500, 600. Said extracorporeal fluid circuit 100, 200, 300, 400, 500, 600 comprises an arterial line 101, 201, 301, 401, 501, 601 connectable to a patient, for drawing blood from the patient and a venous line 102, 202, 302, 402, 502, 602 connectable to the patient for returning blood to the patient. The method comprises after treatment termination from said extracorporeal fluid circuit 110, 210, 310, 410, 510, 610 draining 1000, 2000, 3000 remaining fluid from said extracorporeal fluid circuit through the dialyzer 130, 230, 330, 430, 530, 630.

Remaining fluid may be the remaining liquid present in the extracorporeal fluid circuit after treatment termination.

The dialyzer 130, 230, 330, 430, 530, 630 may be connected to the dialysis machine 110, 210, 310, 410, 510, 610 via a dialyzer fluid circuit 193, 194, 293, 294, 393, 394, 493, 494, 593, 594 for distribution of dialysis fluid to and from the dialyzer 130, 230, 330, 430, 530, 630.

The method may comprise draining 1000, 2000, 3000 remaining fluid from said extracorporeal fluid circuit through the dialyzer 130, 230, 330, 430, 530, 630, e.g. through the dialyzer fluid circuit 193, 194, 293, 294, 393, 394, 493, 494, 593, 594 of the dialyzer 130, 230, 330, 430, 530, 630.

The extracorporeal fluid circuit 110, 210, 310, 410, 510, 610 is drained through the dialyzer 130, 230, 330, 430, 530, 630 by applying a negative pressure on the dialyzer fluid circuit 193, 194, 293, 294, 393, 394, 493, 494, 593, 594 relative the extracorporeal fluid circuit 100, 200, 300, 400, 500, 600.

Expressed differently, a negative pressure gradient is applied on the dialyzer fluid circuit relative the extracorporeal fluid circuit. The negative pressure gradient is applied for achieving a lower pressure in the dialyzer fluid circuit compared to the extracorporeal fluid circuit. Hence, a flow of fluid, e.g. liquid, from the extracorporeal fluid circuit towards the dialyzer fluid circuit is achieved.

In one embodiment, the negative pressure applied on the dialyzer fluid circuit 193, 194, 293, 294, 393, 394, 493, 494, 593, 594 relative the extracorporeal fluid circuit 100, 200, 300, 400, 500, 600 is applied by introducing of gas into the extracorporeal fluid circuit 100, 200, 300, 400, 500, 600.

In one embodiment, the introducing of the gas is performed by pumping of gas into the extracorporeal fluid circuit 100, 200, 300, 400, 500, 600 via an inlet 109, 209, 309, 391, 409, 509, 591, 691. The remaining fluid is pushed towards the dialyzer 130, 230, 330, 430, 530, 630 for draining through the dialysis machine 110, 210, 310, 410, 510, 610. The gas may be air.

In one embodiment, the gas is pumped into the extracorporeal fluid circuit 100, 200, 300, 400, 500, 600 with a pumping device 121, 221, 321, 421, 521 connected to the extracorporeal fluid circuit 100, 200, 300, 400, 500, 600 via the inlet 109, 209, 309, 391, 409, 509, 609.

In one embodiment, the method further comprises introducing a rinse-back fluid 1010, 2010, 3010 into the extracorporeal fluid circuit 100, 200, 300, 400, 500, 600 prior to the draining 1000, 2000, 3000 for filling the extracorporeal fluid circuit 100, 200, 300, 400, 500, 600.

The rinse-back fluid may be a liquid, i.e. a rinse-back liquid.

In one embodiment, the dialyzer 130, 230, 330, 430, 530, 630 is connected to a pump arrangement 63, 64 for distribution of dialysis fluid to and from the dialyzer 130, 230, 330, 430, 530. The method may further comprise controlling 1030, 2030, 3030 said pump arrangement 63, 64 to achieve a net removal of remaining fluid from the dialyzer 130, 230, 330, 430, 530, 630 and the extracorporeal fluid circuit 100, 200, 300, 400, 500 during the applying of negative pressure.

In one embodiment, the dialysis machine 110, 210, 310, 410, 510, 610 is connected to a peristaltic blood pump 122, 222, 322, 422, 522 connected to the arterial line 101, 201, 301, 401, 501, 601. The method may further comprise activating 1005, 2005, 3005 said peristaltic blood pump 122, 222, 322, 422, 522 to generate a flow of the rinse-back fluid in the direction of the dialyzer 130, 230, 330, 430, 530, 630.

In one embodiment, the arterial line 101, 201, 401 comprises a first port 191, 291, 491 connectable to the patient and the venous line 102, 202, 402 comprises a second port 192, 292, 492 connectable to the patient. The method may further comprise connecting 1015, 2015 the first port 191, 291, 491 to the second port 192, 292, 492 prior to introducing the gas into the extracorporeal fluid circuit 100, 200, 400.

In one embodiment, the method further comprises connecting 1004 the arterial line 101, 601 to a rinse-back fluid container 170 prior to introducing the rinse-back fluid into the fluid circuit 100, 600.

The remaining rinse-back fluid in the rinse-back fluid container 170 may be drained through the dialyzer 130, 630 after treatment termination.

The rinse-back fluid in the rinse-back fluid container 170 may hence be drained through the dialyzer fluid circuit 193, 194, 693, 694 of the dialyzer 130, 630 after treatment termination.

In one embodiment, the method may further comprise generating 2003, 3003 a pushback flow of blood in the direction of the arterial line 201, 301, 401, 601 for emptying of the arterial line 201, 301, 401, 601 of blood prior to the generating of the flow of the rinse-back fluid in the direction of the dialyzer 230, 330, 430, 630.

The method may further comprise activating the peristaltic blood pump 222, 322, 422 to generate, e.g. so as to generate, the pushback flow and stopping 2004, 3004 said peristaltic blood pump 222, 322, 422 to stop, e.g. so as to stop, said generating of pushback flow when the arterial line 201, 301, 401 is substantially emptied of blood.

In one embodiment, the dialysis machine 210, 310 is connected to a dialysis fluid pump 224, 324 connected to the extracorporeal fluid circuit 200, 300, 600. The introducing of the rinse-back fluid into the extracorporeal fluid circuit 200, 300, 600 to fill said extracorporeal fluid circuit 200, 300 is performed by activating a dialysis fluid pump 224, 324 so as to generate a flow of the rinse-back fluid in the direction of the venous line 202, 302, 602 through the dialyzer 230, 330, 630.

The flow may be generated in the direction of the venous line 202, 302, 602 through dialyzer blood line of the dialyzer 230, 330, 630. The flow of rinse-back fluid may hence be generated through the dialyzer blood line to the venous line.

The dialysis fluid pump 224 may be connected to the extracorporeal fluid circuit 200 both downstream and upstream of the dialyzer 230 via a clamp arrangement 272, 273. The method may further comprise releasing 2002 said clamp arrangement 272, 273 forming fluid communication between the dialysis fluid pump 224 and the extracorporeal fluid circuit 200 prior to the introduction of the rinse-back fluid into said extracorporeal fluid circuit 200. The releasing 2002 of the clamp arrangement hence establishes fluid communication between the dialysis fluid pump 224 and the extracorporeal fluid circuit 200.

The dialysis fluid pump 224 may be connected to the fluid circuit via a check valve 271. The method may further comprise preventing fluid flow back to the dialysis fluid pump 224 with said check valve 271.

The method may further comprise disposing 2050 said check valve 271 after the extracorporeal fluid circuit 200 is filled with gas.

In one embodiment, the method may further comprise introducing rinse-back fluid into the extracorporeal fluid circuit 400, 500 through controlling of the pump arrangement 63, 64.

In one embodiment, the method may comprise turning 3013 a venous drip chamber 331, 531 connected to the venous line 302, 502, 602.

The venous drip chamber 331, 531 may be turned around for emptying said venous drip chamber 331, 531 of remaining fluid and thereby introduce gas into the extracorporeal fluid circuit 300, 500, 600. The venous drip chamber 331, 531 may be turned substantially upside-down.

The gas may be introduced into the extracorporeal fluid circuit 300, 500, 600 by activation of the peristaltic blood pump 322, 522 to suck gas into the extracorporeal fluid circuit 300, 500, 600 via the first port 391, 591, 691.

The method may further comprise locking 3011 a clamp 368, 568 to the second port 392, 592 after introducing 3010 the extracorporeal fluid circuit 300, 500 with said rinse-back fluid and releasing 3012 said clamp 368, 568 prior to sucking the gas into the fluid circuit via the first port 391, 591.

In one embodiment, the method further comprises conveying 1060, 2060, 3060 the remaining fluid removed from the extracorporeal fluid circuit to a drain 68 of the dialysis machine 110, 210, 310, 410, 510.

The remaining fluid removed from the extracorporeal fluid circuit may be conveyed to the drain 68 of the dialysis machine 110, 210, 310, 410, 510 via the dialyzer fluid circuit 193, 194, 293, 294, 393, 394, 493, 494, 593, 594.

In one embodiment, the pumping device 121, 221, 321, 421, 521 is an air pump.

In one embodiment, the method comprises terminating the draining 1000, 2000, 3000 in response to an exceeding of a predetermined drained fluid volume.

In one embodiment, the method comprises terminating the draining 1000, 2000, 3000 in response to a predetermined pressure in the dialyzer fluid circuit 193, 194, 293, 294, 393, 394, 493, 494, 593, 594, 693, 694.

In one embodiment, the method comprises preventing the applying of negative pressure in response to if blood is detected in the extracorporeal fluid circuit 100, 200, 300, 400, 500, 600.

In one embodiment, the method comprises terminating the applying of negative pressure in response to if blood is detected in the extracorporeal fluid circuit 100, 200, 300, 400, 500, 600. Hence, the applying of negative pressure is terminated in response to blood being detected in said circuit.

In one embodiment, a pre-reinfusion clamp 851 is opened prior to the draining 1000, 2000, 3000 and closed after the rinse-back fluid has been introduced into the extracorporeal circuit 600.

In one embodiment, wherein the arterial line 601 is attached to a service line 651 prior to the draining 1000, 2000, 3000.

According to an aspect a dialysis machine is provided. The dialysis machine 110, 210, 310, 410, 510 connected to an extracorporeal fluid circuit 100, 200, 300, 400, 500 and a dialyzer 130, 230, 330, 430, 530. Said extracorporeal fluid circuit 100, 200, 300, 400, 500 comprises an arterial line 101, 201, 301, 401, 501 connectable to a patient for drawing blood from the patient and a venous line 102, 202, 302, 402, 502 connectable to the patient for returning blood to the patient. The dialysis machine may be configured to perform the method for draining according to the above described embodiments.

According to an aspect a dialysis machine is provided. The dialysis machine 110, 210, 310, 410, 510 connected to an extracorporeal fluid circuit 100, 200, 300, 400, 500 and a dialyzer 130, 230, 330, 430, 530 via a dialyzer fluid circuit 193, 194, 293, 294, 393, 394, 493, 494, 593, 594 and a pump arrangement 63, 64 for distribution of dialysis fluid to and from the dialyzer 130, 230, 330, 430, 530, 630. Said extracorporeal fluid circuit 100, 200, 300, 400, 500 comprises an arterial line 101, 201, 301, 401, 501 connectable to a patient for drawing blood from the patient and a venous line 102, 202, 302, 402, 502 connectable to the patient for returning blood to the patient.

The dialysis machine may comprise a controller 800 and a pumping device 121, 221, 321, 421, 521 connected to the extracorporeal fluid circuit 100, 200, 300, 400, 500, 600 for pumping of gas intro said extracorporeal fluid circuit.

The controller 800 may be operatively connected to said pumping device and the pump arrangement 63, 64. The controller 800 may be configured to control said pumping device and pump arrangement so as to after treatment termination drain 1000, 2000, 3000 remaining fluid from said extracorporeal fluid circuit through the dialyzer 130, 230, 330, 430, 530, 630.

The controller may be configured to control the pump arrangement 63, 64 and the pumping device 121, 122, 321, 421, 521 to after treatment termination drain remaining fluid from said extracorporeal fluid circuit through the dialyzer 130, 230, 330, 430, 530, 630, e.g. through the dialyzer fluid circuit 193, 194, 293, 294, 393, 394, 493, 494, 593, 594 of the dialyzer 130, 230, 330, 430, 530, 630.

The remaining fluid may be liquid present in the extracorporeal fluid circuit after treatment termination.

The pumping device 121, 221, 321, 421, 521 may be configured to pump gas into the extracorporeal fluid circuit 100, 200, 300, 400, 500, 600 via an inlet 109, 209, 309, 391, 409, 509, 591, 691 to push the remaining fluid towards the dialyzer 130, 230, 330, 430, 530, 630 for draining through the dialysis machine 110, 210, 310, 410, 510, 610.

In one embodiment, the controller 800 may be configured to initiate introducing of a rinse-back fluid 1010, 2010, 3010 into the extracorporeal fluid circuit 100, 200, 300, 400, 500, 600 prior to the draining 1000, 2000, 3000 for filling the extracorporeal fluid circuit 100, 200, 300, 400, 500, 600.

The rinse-back fluid may be a liquid, i.e. a rinse-back liquid.

In one embodiment, the controller 800 is configured to control 1030, 2030, 3030 said pump arrangement to achieve a net removal of remaining fluid from the dialyzer 130, 230, 330, 430, 530, 630 and the extracorporeal fluid circuit 100, 200, 300, 400, 500 during the pumping of gas.

The dialysis machine 110, 210, 310, 410, 510 may be connected to a peristaltic blood pump 122, 222, 322, 422, 522 connected to the arterial line 101, 201, 301, 401, 501, 601. Said peristaltic blood pump may be operatively connected to the controller 800 whereby the controller 800 is configured to activate 1005, 2005, 3005 said peristaltic blood pump 122, 222, 322, 422, 522 so as to generate a flow of the rinse-back fluid in the direction of the dialyzer 130, 230, 330, 430, 530, 630. Hence, the controller is configured to activate the peristaltic blood pump to generate said flow.

In one embodiment, the arterial line 101, 201, 401 comprises a first port 191, 291, 491 connectable to the patient and the venous line 102, 202, 402 comprises a second port 192, 292, 492 connectable to the patient. Said ports are arranged to be connectable to each other prior to the pumping of gas into the extracorporeal fluid circuit 100, 200, 400.

The first port 191, 691 may be arranged to be connectable to a rinse-back fluid container 170 prior to introducing the rinse-back fluid into the fluid circuit 100, 600.

The controller 800 may be configured to control the pump arrangement 63,64 so as to drain the remaining rinse-back fluid in the rinse-back fluid container 170 through the dialyzer 130, 630 after treatment termination. Hence, the controller is configured to control the pump arrangement to drain the remaining rinse-back fluid in said container.

The controller 800 may be configured to control the pump arrangement 63, 64 to drain the remaining rinse-back fluid in the rinse-back fluid container 170 through the dialyzer fluid circuit 193, 194, 693, 694 of the dialyzer 130, 630 after treatment termination.

The controller 800 may be further configured to activate the peristaltic blood pump 222, 322, 422 so as to generate 2003, 3003 a pushback flow of blood in the direction of the arterial line 201, 301, 401, 601 for emptying of the arterial line 201, 301, 401, 601 of blood prior to the generating of the flow of the rinse-back fluid in the direction of the dialyzer 230, 330, 430, 630. Hence, the controller is configured to activate the peristaltic blood pump to generate said pushback flow of blood.

The controller 800 may be configured to stop 2004, 3004 said peristaltic blood pump 222, 322, 422 so as to stop said generating of pushback flow when the arterial line 201, 301, 401 is substantially emptied of blood. The controller 800 may thus be configured to stop said peristaltic blood pump to stop said generating of pushback flow.

In one embodiment, the dialysis machine 210, 310 is connected to a dialysis fluid pump 224, 324 connected to the extracorporeal fluid circuit 200, 300, 600. The controller 800 is operatively connected to said dialysis fluid pump and said controller is configured to activate the dialysis fluid pump 224, 324 so as to generate a flow of the rinse-back fluid in the direction of the venous line 202, 302, 602 through the dialyzer 230, 330, 630. The controller is thus configured to activate said dialysis fluid pump to generate said flow of rinse-back fluid.

The controller 800 may be configured to activate the dialysis fluid pump 224, 324 to generate the flow in the direction of the venous line 202, 302, 602 through the dialyzer blood line of the dialyzer 230, 330, 630. The flow of rinse-back fluid may hence be generated through the dialyzer blood line to the venous line.

The dialysis fluid pump 224 may be connected to the extracorporeal fluid circuit 200 both downstream and upstream of the dialyzer 230 via a clamp arrangement 272, 273. The clamp arrangement 272, 273 may be arranged to be released 2002 so as to form fluid communication between the dialysis fluid pump 224 and the extracorporeal fluid circuit 200 prior to the introduction of the rinse-back fluid into said extracorporeal fluid circuit 200.

The dialysis fluid pump 224 may be connected to the fluid circuit via a check valve 271. The check valve 271 is configured to prevent fluid flow back to the dialysis fluid pump 224. The check valve 271 may be a disposable valve.

In one embodiment, the controller 800 may be configured to control the pump arrangement 63, 64 so as to introduce rinse-back fluid into the extracorporeal fluid circuit 400, 500. Hence the controller is configured to control said pump arrangement to introduce the rinse-back fluid.

In one embodiment, a venous drip chamber 331, 531 connected to the venous line 302, 502, 602 is arranged to be turned (3013). The venous drip chamber 331 may be turned around in order to empty said venous drip chamber 331, 531 of remaining fluid and thereby introduce gas into the extracorporeal fluid circuit 300, 500, 600.

The controller 800 may be configured to activate the peristaltic blood pump 322, 522 to suck gas into the extracorporeal fluid circuit 300, 500, 600 via the first port 391, 591, 691.

A clamp 368, 568 may be arranged to be locked 3011 to the second port 392, 592 after introducing 3010 of the extracorporeal fluid circuit 300, 500 with said rinse-back fluid and be released 3012 prior to sucking of the gas into the fluid circuit via the first port 391, 591.

In one embodiment, the controller 800 is configured to control the pumping arrangement 63, 64 so as to convey 1060, 2060, 3060 the remaining fluid removed from the extracorporeal fluid circuit to a drain 68 of the dialysis machine 110, 210, 310, 410, 510.

In one embodiment, the pumping device 121, 221, 321, 421, 521 is an air pump.

In one embodiment, the controller 800 is configured to terminate the draining 1000, 2000, 3000 in response to an exceeding of a predetermined drained fluid volume.

In one embodiment, the controller 800 is configured to terminate the draining 1000, 2000, 3000 in response to reaching of a predetermined pressure in the dialyzer fluid circuit 193, 194, 293, 294, 393, 394, 493, 494, 593, 594, 693, 694.

In one embodiment, the controller 800 is configured to prevent pumping of gas by the pumping device 121, 221, 321, 421, 521 in response to if blood is detected in the extracorporeal fluid circuit 100, 200, 300, 400, 500, 600. Hence the controller may be configured to prevent said pumping in response to detection of blood in said fluid circuit.

In one embodiment, the controller 800 is configured to terminate pumping of gas by the pumping device 121, 221, 321, 421, 521 in response to if blood is detected in the extracorporeal circuit 100, 200, 300, 400, 500, 600. Hence, the controller may be configured to terminate said pumping of gas in response to detection of blood in said fluid circuit.

In one embodiment, a pre-reinfusion clamp 851 is arranged to be opened prior to the draining 1000, 2000, 3000 and closed after the rinse-back fluid has been introduced into the extracorporeal circuit 600.

In one embodiment, the arterial line 601 is arranged to be attached to a service line 651 prior to the draining 1000, 2000, 3000.

According to one aspect a method for filling an extracorporeal fluid circuit is provided. The method is for filling an extracorporeal fluid circuit 200, 300 with rinse-back fluid after treatment termination using a dialysis machine 210, 310. The dialysis machine 210, 310 is connected to a dialyzer 230, 330. Said extracorporeal fluid circuit 200, 300 and a pumping device 224, 324 are connected to the extracorporeal fluid circuit 200, 300. Said extracorporeal fluid circuit 200, 300 comprises an arterial line 201, 301 having a first port 291, 391 connectable to a patient, for drawing blood form the patient and a venous line 202, 302 having a second port 292, 392, connectable to the patient, for returning blood to the patient.

The method comprises pumping rinse-back fluid 2002 into the extracorporeal fluid circuit 200, 300, thereby filling the extracorporeal fluid circuit 200, 300 by activating the pumping device 224, 324 to generate a flow of rinse-back fluid in the direction of the second port 292, 392 through the dialyzer 230, 330.

The flow may be generated in the direction of the venous line 202, 302 through dialyzer blood line of the dialyzer 230, 330.

The rinse-back fluid may be a liquid, i.e. a rinse-back liquid.

The method may further comprise pumping 2001 so as to, e.g. to, generate a pushback flow of blood in the direction of the first port 291, 391 so as to empty the arterial line 201, 301 of blood. Hence, the pushback flow is for emptying the arterial line of blood.

The dialysis machine 210, 310 may be connected to a peristaltic blood pump 222, 322 via the extracorporeal fluid circuit 200, 300. The method may further comprise activating 2003 a peristaltic blood pump 222, 322 connected to the extracorporeal fluid circuit 200, 300 to generate flow of rinse-back fluid in the direction of the second port 292, 392.

Generating 2003 the pushback flow may comprise activating the peristaltic blood pump 222, 322 so as to generate the pushback flow and stopping 2004 said peristaltic blood pump 222, 322 so as to stop said pumping of pushback flow when the arterial line 201, 301 is substantially emptied of blood. Hence the peristaltic blood pump is activated to generate the pushback flow and stopped for terminating said pushback flow.

In one embodiment, the pumping device 224 is connected to the extracorporeal fluid circuit 200 via a clamp arrangement 272, 273 both downstream and upstream of the dialyzer 230. The method may further comprise releasing 2002 said clamp arrangement 272, 273 forming fluid communication between the pumping device 224 and the extracorporeal fluid circuit 200 prior to the pumping of the rinse-back fluid into said extracorporeal fluid circuit 200.

In one embodiment, the pumping device 224 is connected to the fluid circuit via a check valve 271. The method may further comprise preventing fluid flow back to the dialysis fluid pump 224 with the check valve 271.

In one embodiment, the pumping device 224, 324 is a dialysis fluid pump. The dialysis fluid pump is arranged to provide dialysis fluid to the extracorporeal fluid circuit 200, 300.

According to one aspect a dialysis machine is provided. The dialysis machine 210, 310 is connected to a dialyzer 230, 330, an extracorporeal fluid circuit 200, 300 and a pumping device 224, 324 connected to the extracorporeal fluid circuit 200, 300. Said extracorporeal fluid circuit 200, 300 comprises an arterial line 201, 301 connectable to a patient for drawing blood from the patient and a venous line 202, 302 connectable to the patient for returning blood to the patient. Said dialysis machine is configured to perform the method for filling according to any of the embodiments described above.

According to one aspect a dialysis machine is provided. The dialysis machine 210, 310 is connected to a dialyzer 230, 330, an extracorporeal fluid circuit 200, 300 and a pumping device 224, 324 connected to the extracorporeal fluid circuit 200, 300. Said extracorporeal fluid circuit 200, 300 comprises an arterial line 201, 301 connectable to a patient for drawing blood from the patient and a venous line 202, 302 connectable to the patient for returning blood to the patient. The dialysis machine comprises a controller 800 operatively connected to said pumping device.

Said controller is configured to control the pumping device 224, 324 to generate a flow of rinse-back fluid in the direction of the second port 292, 392 through the dialyzer 230, 330, thereby generating pumping of rinse-back fluid 2002 into the extracorporeal fluid circuit 200, 300 thus filling said extracorporeal fluid circuit.

The controller may be configured to control the pumping device 224, 324 to generate the flow rinse-back fluid in the direction of the second port 292, 392 through the dialyzer blood line of the dialyzer 230, 330. The flow of rinse-back fluid may hence be generated through the dialyzer blood line to the venous line.

The rinse-back fluid may be a liquid, i.e. a rinse-back liquid.

The controller 800 may be configured to control the pumping device 224, 324 so as to pump 2001 to generate a pushback flow of blood in the direction of the first port 291, 391 so as to empty the arterial line 201, 301 of blood. Hence the pushback flow is generated for emptying said arterial line.

The controller 800 may be configured to activate 2003 a peristaltic blood pump 222, 322 connected to the extracorporeal fluid circuit 200, 300 and operatively connected to the controller 800 so as to generate flow of rinse-back fluid in the direction of the second port 292, 392. Hence, the controller is configured to activate said peristaltic blood pump for generating said flow of rinse-back fluid.

The controller 800 may be further configured to stop 2004 said peristaltic blood pump 222, 322 so as to stop said pumping of pushback flow when the arterial line 201, 301 is substantially emptied of blood. Hence, the controller is configured to stop said peristaltic blood pump when the arterial line is substantially emptied of blood.

In one embodiment, the pumping device 224 is connected to the extracorporeal fluid circuit 200 via a clamp arrangement 272, 273 both downstream and upstream of the dialyzer 230. Said clamp arrangement is arranged to be released 2002 so as to form fluid communication between the pumping device 224 and the extracorporeal fluid circuit 200 prior to the pumping of the rinse-back fluid into said extracorporeal fluid circuit 200. Hence said clamp arrangement is arranged to be released in order to form said fluid communication.

In one embodiment, the pumping device 224, 324 is a dialysis fluid pump, the dialysis fluid pump being arranged to provide dialysis fluid to the extracorporeal fluid circuit 200, 300.

According to an aspect a method for draining an extracorporeal fluid circuit 100, 200, 300, 400, 500, 600 utilizing a dialysis machine 110, 210, 310, 410, 510 is provided. The dialysis machine 110, 210, 310, 410, 510, 610 is connected to a dialyzer 130, 230, 330, 430, 530, 630 and said extracorporeal fluid circuit 100, 200, 300, 400, 500, 600. The extracorporeal fluid circuit 100, 200, 300, 400, 500, 600 comprises an arterial line 101, 201, 301, 401, 501, 601 connectable to a patient, for drawing blood from the patient and a venous line 102, 202, 302, 402, 502, 602 connectable to the patient for returning blood to the patient.

The method comprises after treatment termination from said extracorporeal fluid circuit 110, 210, 310, 410, 510, 610 draining 1000, 2000, 3000 remaining fluid from said extracorporeal fluid circuit through the dialyzer 130, 230, 330, 430, 530, 630.

The method may comprise draining 1000, 2000, 3000 remaining fluid from said extracorporeal fluid circuit through the dialyzer 130, 230, 330, 430, 530, 630, e.g. through the dialyzer fluid circuit 193, 194, 293, 294, 393, 394, 493, 494, 593, 594 of the dialyzer 130, 230, 330, 430, 530, 630.

The remaining fluid may be liquid present in the extracorporeal fluid circuit after treatment termination.

The method may further comprise introducing a rinse-back fluid 1010, 2010, 3010 into the extracorporeal fluid circuit 100, 200, 300, 400, 500, 600 prior to the draining 1000, 2000, 3000 for filling the extracorporeal fluid circuit 100, 200, 300, 400, 500, 600.

The rinse-back fluid may be a liquid, i.e. a rinse-back liquid.

The method may further comprise introducing a lysating fluid 6090 into the extracorporeal fluid circuit 100, 200, 300, 400, 500, 600 after the introduction of the rinse-back fluid 1010, 2010, 3010 for filling the extracorporeal fluid circuit 100, 200, 300, 400, 500, 600 prior to the draining 1000, 2000, 3000.

In one embodiment, the dialyzer 130, 230, 330, 430, 530, 630 is connected to the dialysis machine 110, 210, 310, 410, 510, 610 via a dialyzer fluid circuit 193, 194, 293, 294, 393, 394, 493, 494, 593, 594 for distribution of dialysis fluid to and from the dialyzer 130, 230, 330, 430, 530, 630. The extracorporeal fluid circuit 110, 210, 310, 410, 510, 610 is drained through the dialyzer 130, 230, 330, 430, 530, 630 by applying a negative pressure on the dialyzer fluid circuit 193, 194, 293, 294, 393, 394, 493, 494, 593, 594 relative the extracorporeal fluid circuit 100, 200, 300, 400, 500, 600. Accordingly, the negative pressure is applied for draining via the dialyzer fluid circuit 193, 194, 293, 294, 393, 394, 493, 494, 593, 594.

Expressed differently, a negative pressure gradient is applied on the dialyzer fluid circuit relative the extracorporeal fluid circuit. The negative pressure gradient is applied for achieving a lower pressure in the dialyzer fluid circuit compared to the extracorporeal fluid circuit. Hence, a flow of fluid, e.g. liquid, from the extracorporeal fluid circuit towards the dialyzer fluid circuit is achieved.

In one embodiment, the negative pressure applied on the dialyzer fluid circuit 193, 194, 293, 294, 393, 394, 493, 494, 593, 594 relative the extracorporeal fluid circuit 100, 200, 300, 400, 500, 600 is applied by introducing of gas into the extracorporeal fluid circuit 100, 200, 300, 400, 500, 600. The gas may be air.

The introducing of the gas may be performed by pumping of gas into the extracorporeal fluid circuit 100, 200, 300, 400, 500, 600 via an inlet 109, 209, 309, 391, 409, 509, 591, 691, whereby the remaining fluid is pushed towards the dialyzer 130, 230, 330, 430, 530, 630 for draining through the dialysis machine 110, 210, 310, 410, 510, 610.

In one embodiment, the gas is pumped into the extracorporeal fluid circuit 100, 200, 300, 400, 500, 600 with a pumping device 121, 221, 321, 421, 521 connected to the extracorporeal fluid circuit 100, 200, 300, 400, 500, 600 via the inlet 109, 209, 309, 391, 409, 509, 609.

In one embodiment, the dialyzer 130, 230, 330, 430, 530, 630 is connected to a pump arrangement 63, 64 for distribution of dialysis fluid to and from the dialyzer 130, 230, 330, 430, 530. The method may further comprise controlling 1030, 2030, 3030 said pump arrangement 63, 64 to achieve a net removal of remaining fluid from the dialyzer 130, 230, 330, 430, 530, 630 and the extracorporeal fluid circuit 100, 200, 300, 400, 500 during the applying of negative pressure.

In one embodiment, the dialysis machine 110, 210, 310, 410, 510, 610 is connected to a peristaltic blood pump 122, 222, 322, 422, 522 connected to the arterial line 101, 201, 301, 401, 501, 601. The method may further comprise activating 1005, 2005, 3005 said peristaltic blood pump 122, 222, 322, 422, 522 to generate a flow of the rinse-back fluid and/or lysating fluid in the direction of the dialyzer 130, 230, 330, 430, 530, 630 during the introduction of rinse-back fluid and lysating fluid, respectively.

In one embodiment, the arterial line 101, 201, 401 comprises a first port 191, 291, 491 connectable to the patient and the venous line 102, 202, 402 comprises a second port 192, 292, 492 connectable to the patient. The method may further comprise connecting 1015, 2015 the first port 191, 291, 491 to the second port 192, 292, 492 prior to introducing the gas into the extracorporeal fluid circuit 100, 200, 400.

In one embodiment, the method further comprises connecting 1004 the arterial line 101, 601 to a rinse-back fluid container 170 prior to introducing the rinse-back fluid into the fluid circuit 100, 600.

The remaining rinse-back fluid in the rinse-back fluid container 170 may be drained through the dialyzer 130, 630 after treatment termination.

The remaining rinse-back fluid in the rinse-back fluid container 170 may be drained through the dialyzer fluid circuit of the dialyzer after treatment termination.

In one embodiment, the method may further comprise connecting 6004 the arterial line 101, 601 to a lysating fluid container 970 prior to introducing the lysating fluid into the fluid circuit 100, 600.

Remaining lysating fluid in the lysating fluid container 970 may be drained through the dialyzer 130, 630 after treatment termination.

The remaining lysating fluid in the lysating fluid container 970 may be drained through the dialyzer fluid circuit of the dialyzer after treatment termination.

In one embodiment, the method may further comprise generating 2003, 3003 a pushback flow of blood in the direction of the arterial line 201, 301, 401, 601 for emptying of the arterial line 201, 301, 401, 601 of blood prior to the generating of the flow of the rinse-back fluid in the direction of the dialyzer 230, 330, 430, 630.

The method may further comprise activating the peristaltic blood pump 222, 322, 422 so as to generate the pushback flow and stopping 2004, 3004 said peristaltic blood pump 222, 322, 422 so as to stop said generating of pushback flow when the arterial line 201, 301, 401 is substantially emptied of blood. Hence the peristaltic blood pump is activated to generate the pushback flow and stopped to terminate said pushback flow.

In one embodiment, the dialysis machine 210, 310 is connected to a dialysis fluid pump 224, 324 connected to the extracorporeal fluid circuit 200, 300, 600. The introducing of the rinse-back fluid into the extracorporeal fluid circuit 200, 300, 600 to fill said extracorporeal fluid circuit 200, 300 is performed by activating a dialysis fluid pump 224, 324 so as to generate a flow of the rinse-back fluid in the direction of the venous line 202, 302, 602 through the dialyzer 230, 330, 630. Hence, the dialysis fluid pump is activated to generate said flow of rinse-back fluid.

The flow of rinse-back fluid is generated in the direction of the venous line 202, 302, 602 through the dialyzer blood line of the dialyzer 230, 330, 630 to the venous line 202, 302, 602.

In one embodiment, the dialysis machine 210, 310 is connected to a lysating fluid pump 924 connected to the extracorporeal fluid circuit 200, 300, 600. The introducing of the lysating fluid into the extracorporeal fluid circuit 200, 300, 600 to fill said extracorporeal fluid circuit 200, 300 is performed by activating the lysating fluid pump 924 so as to generate a flow of the lysating fluid in the direction of the venous line 202, 302, 602 through the dialyzer 230, 330, 630.

The flow of lysating fluid is generated in the direction of the venous line 202, 302, 602 through the dialyzer blood line of the dialyzer 230, 330, 630 to the venous line 202, 302, 602.

The dialysis fluid pump 224 may be connected to the extracorporeal fluid circuit 200 both downstream and upstream of the dialyzer 230 via a clamp arrangement 272, 273. The method may further comprise releasing 2002 said clamp arrangement 272, 273 forming fluid communication between the dialysis fluid pump 224 and the extracorporeal fluid circuit 200 prior to the introduction of the rinse-back fluid into said extracorporeal fluid circuit 200. The clamp arrangement 272, 273 are thus released in order to achieve fluid communication between said dialysis fluid pump and the extracorporeal fluid circuit.

The dialysis fluid pump 224 may be connected to the fluid circuit via a check valve 271. The method may further comprise preventing fluid flow back to the dialysis fluid pump 224 with said check valve 271.

The method may further comprise disposing 2050 said check valve 271 after the extracorporeal fluid circuit 200 is filled with gas.

In one embodiment, the method further comprises introducing rinse-back fluid into the extracorporeal fluid circuit 400, 500 through controlling of the pump arrangement 63, 64.

In one embodiment, the pump arrangement 63, 64 further comprises a lysating fluid pump for distribution of lysating fluid to and from the dialyzer 130, 230, 330, 430, 530. The method further comprises controlling said pump arrangement 63, 64 to distribute lysating fluid into the extracorporeal fluid circuit 100, 200, 300, 400, 500 after the rinse-back fluid has been introduced into said extracorporeal fluid circuit 100, 200, 300, 400, 500.

The pump arrangement 63, 64 may be controlled to distribute lysating fluid into the extracorporeal fluid circuit 100, 200, 300, 400, 500 maintaining a removal of fluid from the dialyzer 130, 230, 330, 430, 530, 630 and the extracorporeal fluid circuit 100, 200, 300, 400, 500.

In one embodiment, the method further comprises turning 3013 a venous drip chamber 331, 531 connected to the venous line 302, 502, 602.

The venous drip chamber 331, 531 may be turned around for emptying said venous drip chamber 331, 531 of remaining fluid in order to introduce gas into the extracorporeal fluid circuit 300, 500, 600. The venous drip chamber may be turned upside-down.

In one embodiment, gas is introduced into the extracorporeal fluid circuit 300, 500, 600 by activation of the peristaltic blood pump 322, 522 to suck gas into the extracorporeal fluid circuit 300, 500, 600 via the first port 391, 591, 691.

The method may further comprise locking 3011 a clamp 368, 568 to the second port 392, 592 after introducing 3010 the extracorporeal fluid circuit 300, 500 with said rinse-back fluid and releasing 3012 said clamp 368, 568 prior to sucking the gas into the fluid circuit via the first port 391, 591.

In one embodiment, the method further comprises conveying 1060, 2060, 3060 the remaining fluid removed from the extracorporeal fluid circuit to a drain 68 of the dialysis machine 110, 210, 310, 410, 510.

The drain 68 may be connected to the dialyzer fluid circuit, whereby the method may comprise conveying remaining fluid to the drain 68 via the dialyzer fluid circuit of the dialyzer.

In one embodiment, the pumping device 121, 221, 321, 421, 521 is an air pump.

In one embodiment, the method further comprises terminating the draining 1000, 2000, 3000 in response to an exceeding of a predetermined drained fluid volume.

In one embodiment, the method further comprises terminating the draining 1000, 2000, 3000 in response to a predetermined pressure in the dialyzer fluid circuit 193, 194, 293, 294, 393, 394, 493, 494, 593, 594, 693, 694. Accordingly. The draining may be terminated in response to the pressure exceeding a predetermined pressure in the dialyzer fluid circuit.

In one embodiment, the method further comprises preventing the applying of negative pressure in response to if blood is detected in the extracorporeal fluid circuit 100, 200, 300, 400, 500, 600. Hence, the applying of negative pressure is prevented in response to the detection of blood in said extracorporeal fluid circuit.

In one embodiment, the method further comprises terminating the applying of negative pressure in response to if blood is detected in the extracorporeal circuit (100, 200, 300, 400, 500, 600. The applying of negative pressure may thus be terminated in response to the detection of blood in said extracorporeal fluid circuit.

In one embodiment, the method comprises draining 1000, 2000, 3000 remaining fluid from the extracorporeal fluid circuit 100, 200, 300, 400, 500, 600 through the dialyzer 130, 230, 330, 430, 530, 630 after introduction of the rinse-back fluid 1010, 2010, 3010 and prior to the introduction of lysating fluid 6090 into said extracorporeal fluid circuit.

In one embodiment, a pre-reinfusion clamp 851 is opened prior to the draining 1000, 2000, 3000 and closed after the rinse-back fluid has been introduced into the extracorporeal circuit 600.

In one embodiment, the arterial line 601 is attached to a service line 651 prior to the draining 1000, 2000, 3000.

In one embodiment, the lysating fluid is a liquid.

In one embodiment, the lysating fluid comprises citric acid.

In one embodiment, the lysating fluid comprises RO-water.

According to an aspect, a dialysis machine 110, 210, 310, 410, 510 connected to an extracorporeal fluid circuit 100, 200, 300, 400, 500 and a dialyzer 130, 230, 330, 430, 530 is provided. The extracorporeal fluid circuit 100, 200, 300, 400, 500 comprises an arterial line 101, 201, 301, 401, 501 connectable to a patient for drawing blood from the patient and a venous line 102, 202, 302, 402, 502 connectable to the patient for returning blood to the patient. The dialysis machine is configured to perform the method for draining according to any of the above mentioned embodiments.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims and clauses.

The invention claimed is:

1. A method for draining an extracorporeal fluid circuit utilizing a dialysis machine, wherein the dialysis machine is connected to a dialyzer and the extracorporeal fluid circuit, wherein the extracorporeal fluid circuit includes an arterial line connectable to a patient for drawing blood from the patient and a venous line connectable to the patient for returning the blood to the patient, the method comprising:

after treatment termination, draining rinse-back fluid from the extracorporeal fluid circuit through the dialyzer, wherein the dialyzer is connected to the dialysis machine via a dialyzer fluid circuit for distribution of the rinse-back fluid to and from the dialyzer, the dialyzer being further connected to a pump arrangement via the dialyzer fluid circuit, wherein the pump arrangement is arranged to control a distribution of the rinse-back fluid into and from the extracorporeal fluid circuit via the dialyzer, wherein the extracorporeal fluid circuit is drained through the dialyzer by applying a negative pressure on the dialyzer fluid circuit relative to the extracorporeal fluid circuit, thereby draining the extracorporeal fluid circuit through the dialyzer, the negative pressure being applied on the dialyzer fluid circuit relative to the extracorporeal fluid circuit by introducing gas into the extracorporeal fluid circuit; and controlling the pump arrangement to achieve a net removal of the rinse-back fluid from the dialyzer and the extracorporeal fluid circuit during the applying of negative pressure, the net removal consequently causing the extracorporeal fluid circuit to gradually empty, wherein the gas is introduced into the extracorporeal fluid circuit by activation of a peristaltic blood pump to pull the gas into the extracorporeal fluid circuit via a first port; and wherein the pump arrangement is controlled to achieve the net removal of the rinse-back fluid from the extracorporeal circuit by controlling the pump arrangement at a higher flow rate than the peristaltic blood pump.

2. The method according to claim 1, wherein the arterial line includes a first port connectable to the patient and the venous line includes a second port connectable to the patient, the method further comprising connecting the first port to the second port prior to introducing the gas into the extracorporeal fluid circuit.

3. The method according to claim 1, wherein the extracorporeal fluid circuit is for hemodiafiltration (HDF) dialysis treatment and comprises at least one of a pre-dilution line and a post dilution line.

4. The method according to claim 1, wherein a drain is connected to the dialyzer fluid circuit, and wherein the pump arrangement is connected to the drain to enable the draining of the rinse-back fluid from the extracorporeal fluid circuit.

5. The method according to claim 4, wherein the pump arrangement comprises a first dialyzer pump and a second dialyzer pump that are both connected to the dialyzer fluid circuit, wherein the drain is connected to an outlet of the first dialyzer pump, and wherein an inlet of the second dialyzer pump is directly connected to a supply line of dialysis fluid.

6. The method according to claim 5, wherein the controlling of the pump arrangement to achieve the net removal of the rinse-back fluid from the dialyzer and the extracorporeal fluid circuit during the applying of negative pressure is achieved by controlling the first dialyzer pump and the second dialyzer pump, the net removal being provided by controlling the first dialyzer pump to pump the rinse-back fluid in the dialyzer towards the drain of the dialyzer fluid circuit at a faster speed than the second dialyzer pump provides the rinse-back fluid into the dialyzer.

7. The method according to claim 1, wherein the dialyzer fluid circuit includes a pressure sensor configured to monitor a pressure in the dialyzer fluid circuit, wherein the pump arrangement is configured to be controlled in response to sensor signals from the pressure sensor, and wherein a pressure difference is maintained and ensured by the pump arrangement that is controlled in response to the sensor signals generated by the pressure sensor.

8. The method according to claim 1, wherein the method further comprises introducing the rinse-back fluid into the extracorporeal fluid circuit for filling the extracorporeal fluid circuit prior to the draining.

9. The method according to claim 8, wherein the dialysis machine is connected to a peristaltic blood pump that is connected to the arterial line, the method further comprising:

activating the peristaltic blood pump to generate a flow of the rinse-back fluid in a direction of the dialyzer, and generating a pushback flow of blood in a direction of the arterial line such that the arterial line is emptied of the blood prior to generating the flow of the rinse-back fluid in the direction of the dialyzer.

10. The method according to claim 8, wherein the dialysis machine is connected to a dialysis fluid pump that is connected to the extracorporeal fluid circuit, wherein introducing the rinse-back fluid into the extracorporeal fluid circuit to fill the extracorporeal fluid circuit is performed by activating the dialysis fluid pump to generate a flow of the rinse-back fluid in a direction of the venous line through the dialyzer.

11. The method according to claim 1, further comprising:

after treatment termination, introducing the rinse-back fluid into the extracorporeal fluid circuit such that the extracorporeal fluid circuit is filled;

introducing a lysating fluid into the extracorporeal fluid circuit after the introduction of the rinse-back fluid such that the extracorporeal fluid circuit is filled; and after introducing the rinse-back fluid and the lysating fluid, draining the rinse-back fluid and the lysating fluid from the extracorporeal fluid circuit through the dialyzer.

12. The method according to claim 11, wherein the dialysis machine is connected to a peristaltic blood pump that is connected to the arterial line, the method further comprising activating the peristaltic blood pump to generate a flow of the rinse-back fluid and the lysating fluid in a direction of the dialyzer during the respective introductions of the rinse-back fluid and the lysating fluid.

13. The method according to claim 11, wherein the dialysis machine is connected to a lysating fluid pump that is connected to the extracorporeal fluid circuit, wherein introducing the lysating fluid into the extracorporeal fluid circuit to fill the extracorporeal fluid circuit is performed by activating the lysating fluid pump so as to generate a flow of the lysating fluid in a direction of the venous line through the dialyzer, and wherein the lysating fluid includes one or both of citric acid and RO-water.

14. The method according to claim 11, wherein the pump arrangement further comprises a lysating fluid pump for distribution of the lysating fluid to and from the dialyzer, the method further comprising controlling the pump arrangement to distribute the lysating fluid into the extracorporeal fluid circuit after the rinse-back fluid has been introduced into the extracorporeal fluid circuit, wherein the pump arrangement is controlled to distribute the lysating fluid into the extracorporeal fluid circuit such that a removal of the rinse-back fluid from the dialyzer and the extracorporeal fluid circuit is maintained.

15. The method according to claim 1, wherein the introducing of the gas is performed by pumping the gas into the extracorporeal fluid circuit via an inlet, wherein the rinse-back fluid is driven towards the dialyzer by the gas for draining through the dialysis machine, wherein the gas is pumped into the extracorporeal fluid circuit with an air pump connected to the extracorporeal fluid circuit via the inlet, and wherein the gas introduced is air.

16. The method according to claim 15, wherein the air pump is connected to the extracorporeal fluid circuit via an inlet to a venous drip chamber.

17. The method according to claim 1, wherein the extracorporeal fluid circuit includes a venous drip chamber connected to the venous line, the method further comprising turning the venous drip chamber for emptying of the venous drip chamber of the rinse-back fluid and to introduce gas into the extracorporeal fluid circuit.

18. The method according to claim 1, further comprising terminating the draining in response to reaching a predetermined pressure in the dialyzer fluid circuit.

19. A dialysis machine connected to an extracorporeal fluid circuit and a dialyzer, wherein the extracorporeal fluid circuit includes an arterial line connectable to a patient for drawing blood from the patient and a venous line connectable to the patient for returning the blood to the patient, and wherein the dialysis machine is configured to perform the method according to claim 1.

* * * * *